(12) United States Patent
Mitariten

(10) Patent No.: US 10,450,522 B2
(45) Date of Patent: Oct. 22, 2019

(54) INTEGRATED PTSA/MEMBRANE METHOD AND SYSTEM FOR H2S AND CO2 REMOVAL FROM BIOGAS

(71) Applicant: Air Liquide Advanced Technologies U.S. LLC, Houston, TX (US)

(72) Inventor: Michael J. Mitariten, Pittstown, NJ (US)

(73) Assignee: Air Liquide Advanced Technologies U.S. LLC, Houston, TX (US)

(*) Notice: Subject to any disclaimer, the term of this patent is extended or adjusted under 35 U.S.C. 154(b) by 0 days.

(21) Appl. No.: 16/207,853

(22) Filed: Dec. 3, 2018

(65) Prior Publication Data

US 2019/0169517 A1 Jun. 6, 2019

Related U.S. Application Data

(62) Division of application No. 15/887,588, filed on Feb. 2, 2018, now Pat. No. 10,179,883.
(Continued)

(51) Int. Cl.
*B01D 53/047* (2006.01)
*C10L 3/10* (2006.01)
(Continued)

(52) U.S. Cl.
CPC ............ *C10L 3/104* (2013.01); *B01D 53/047* (2013.01); *B01D 53/0462* (2013.01); *B01D 53/229* (2013.01); *C10L 3/101* (2013.01); *C10L 3/103* (2013.01); *C10L 3/106* (2013.01); *C12M 21/04* (2013.01); *B01D 2256/245* (2013.01); *B01D 2257/104* (2013.01); *B01D 2257/304* (2013.01); *B01D 2257/504* (2013.01);
(Continued)

(58) Field of Classification Search
None
See application file for complete search history.

(56) References Cited

U.S. PATENT DOCUMENTS 4,770,676 A 9/1988 Sircar et al.
6,018,060 A * 1/2000 Baker .................. B01D 53/22
549/513
(Continued)

FOREIGN PATENT DOCUMENTS

FR 2 758 475 7/1998
FR 2 836 058 8/2003
FR 3 035 337 10/2016

OTHER PUBLICATIONS

Kumar, et al., "Purification by Adsorptive Separation," Chemical Engineering Progress, Jan. 1989, pp. 34-40.
(Continued)

*Primary Examiner* — Tam M Nguyen
(74) *Attorney, Agent, or Firm* — Christopher J. Cronin

(57) ABSTRACT

Biogas containing $H_2S$ and $CO_2$ is upgraded by removing $H_2S$ using PTSA and $CO_2$ using two stages of gas separation membranes. The first stage permeate may optionally be used a regeneration gas stream. The second stage permeate may optionally be used a cool down gas stream. The PTSA unit includes two or more adsorbent beds each selective for water, VOCs, and $H_2S$ over $CO_2$ and for $H_2S$ over methane.

6 Claims, 48 Drawing Sheets

Related U.S. Application Data

(60) Provisional application No. 62/454,255, filed on Feb. 3, 2017.

(51) Int. Cl.
*C12M 1/107* (2006.01)
*B01D 53/04* (2006.01)
*B01D 53/22* (2006.01)

(52) U.S. Cl.
CPC .... *B01D 2257/708* (2013.01); *B01D 2257/80* (2013.01); *B01D 2258/05* (2013.01); *B01D 2259/40001* (2013.01); *B01D 2259/402* (2013.01); *B01D 2259/403* (2013.01); *B01D 2259/404* (2013.01); *B01D 2259/40013* (2013.01); *C10G 2300/1011* (2013.01); *C10G 2300/207* (2013.01); *C10L 2200/0469* (2013.01); *C10L 2290/02* (2013.01); *C10L 2290/06* (2013.01); *C10L 2290/12* (2013.01); *C10L 2290/46* (2013.01); *C10L 2290/48* (2013.01); *C10L 2290/542* (2013.01); *C10L 2290/548* (2013.01); *Y02C 10/08* (2013.01); *Y02C 10/10* (2013.01); *Y02E 50/343* (2013.01); *Y02P 30/20* (2015.11)

(56) References Cited

U.S. PATENT DOCUMENTS

| | | | |
|---|---|---|---|
| 7,025,803 | B2 | 4/2006 | Wascheck et al. |
| 8,158,378 | B2 | 4/2012 | Mitariten |
| 8,221,524 | B2 | 7/2012 | Mitariten |
| 9,480,944 | B2 | 11/2016 | Ballantyne et al. |
| 2004/0103782 | A1 | 6/2004 | Wascheck et al. |
| 2007/0068386 | A1 | 3/2007 | Mitariten |
| 2010/0242724 | A1* | 9/2010 | Chen ............... B01D 53/0476 95/51 |
| 2012/0012000 | A1* | 1/2012 | Wright ............. B01D 53/047 95/43 |
| 2012/0264197 | A1 | 10/2012 | Mitariten |
| 2013/0108531 | A1 | 5/2013 | Mitariten |
| 2019/0001263 | A1* | 1/2019 | Prince ............... B01D 53/002 |

OTHER PUBLICATIONS

International Search Report and Written Opinion for PCT/US2018/016674, dated Sep. 3, 2018.

* cited by examiner

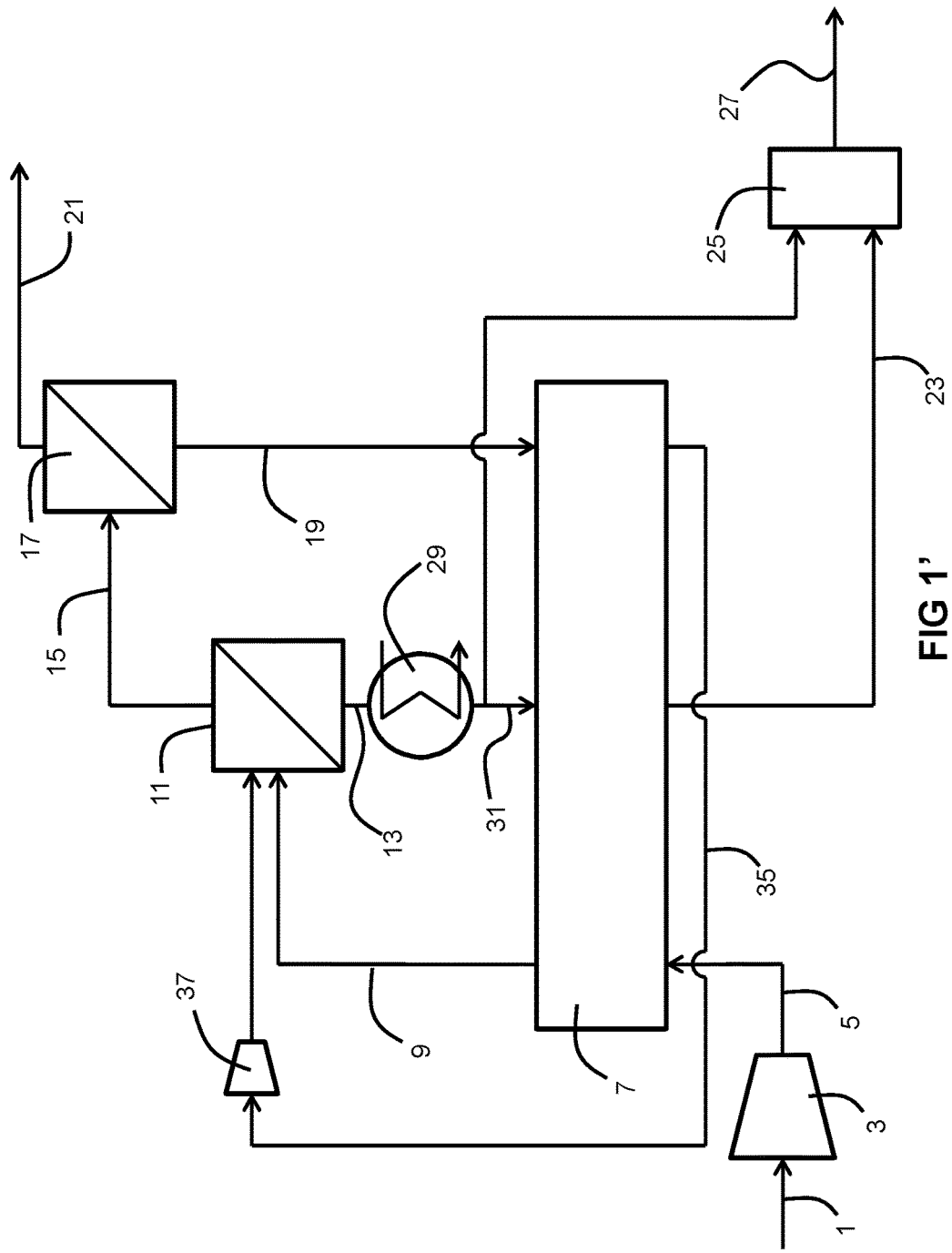

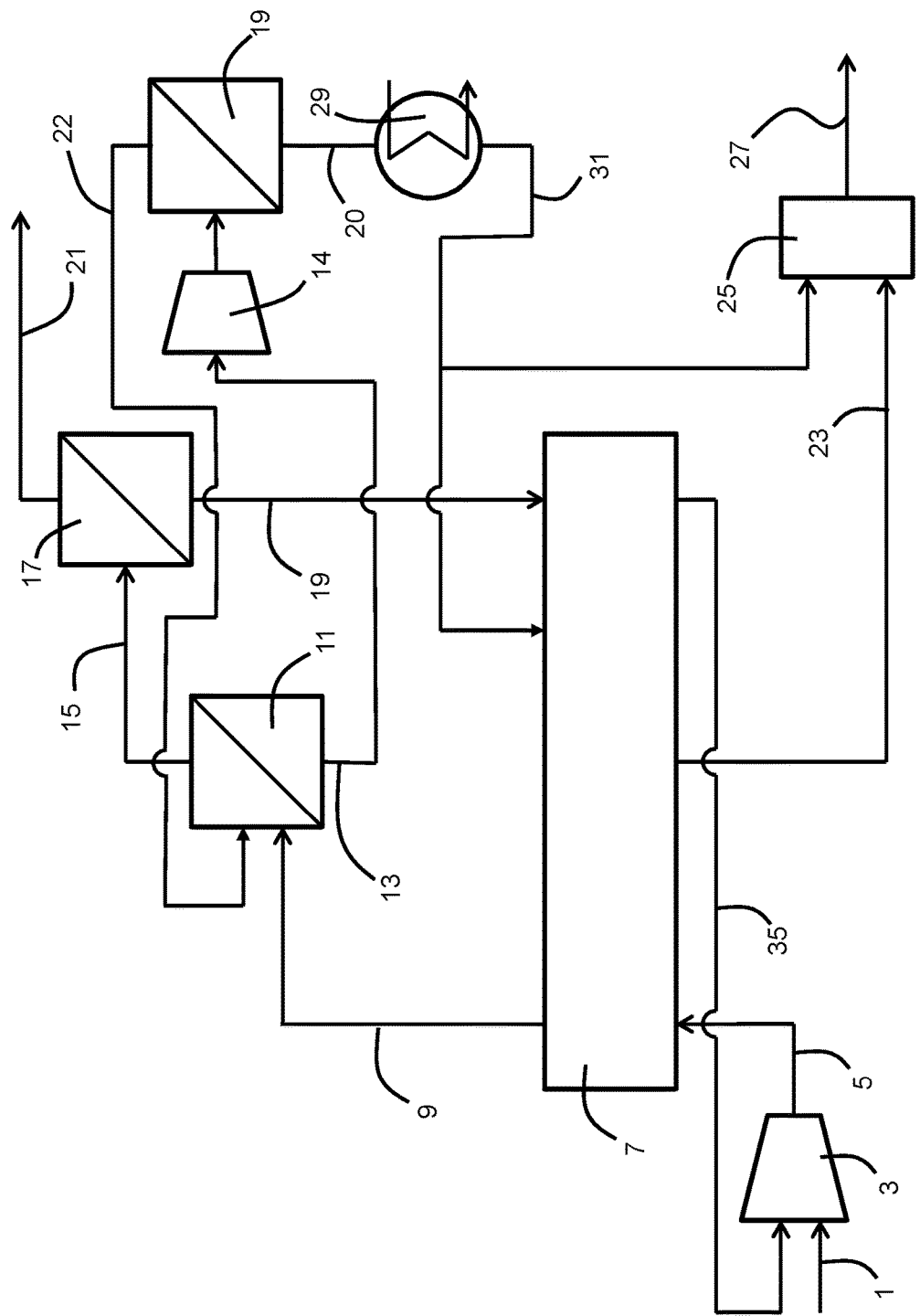
FIG 1"

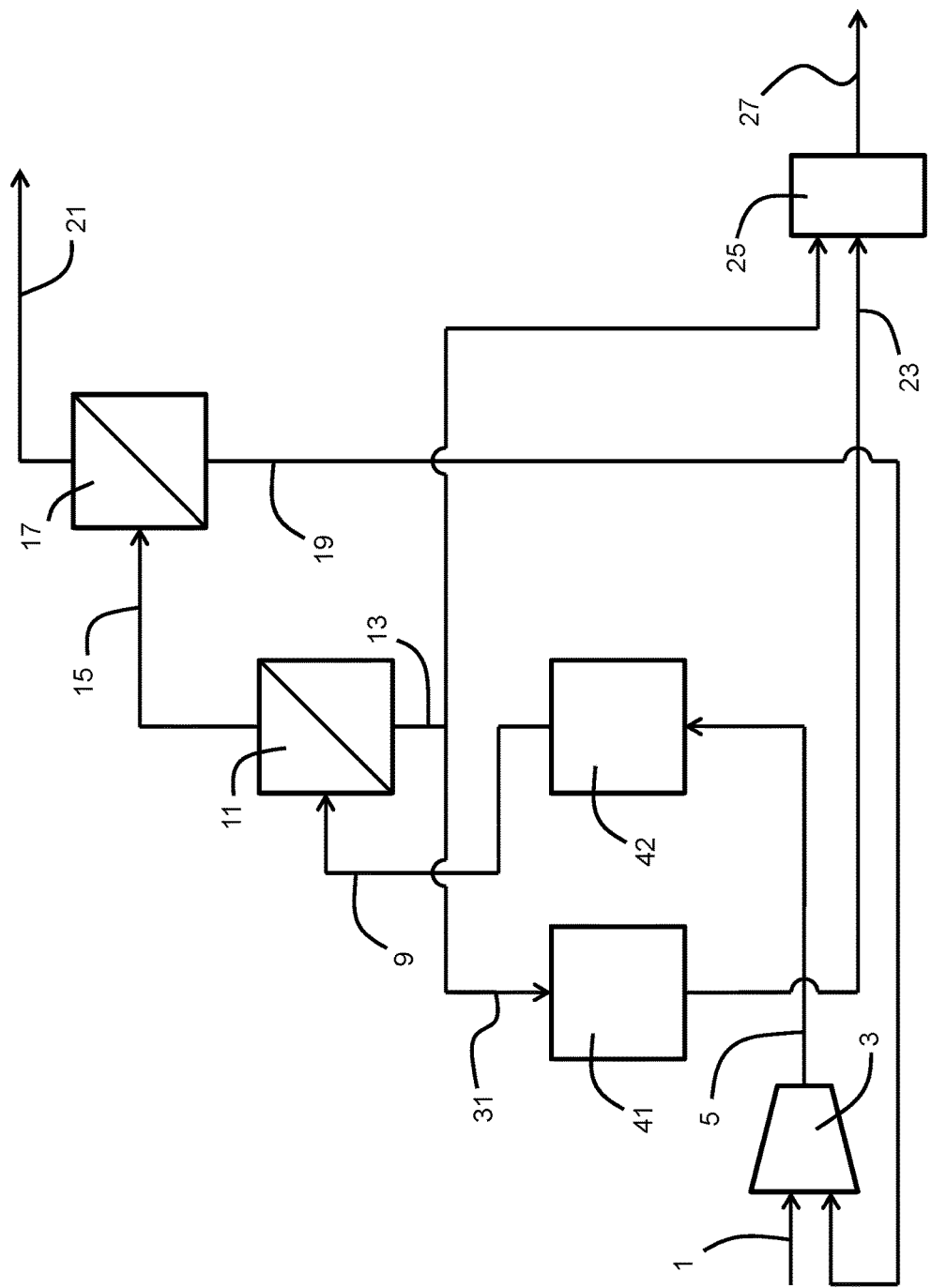

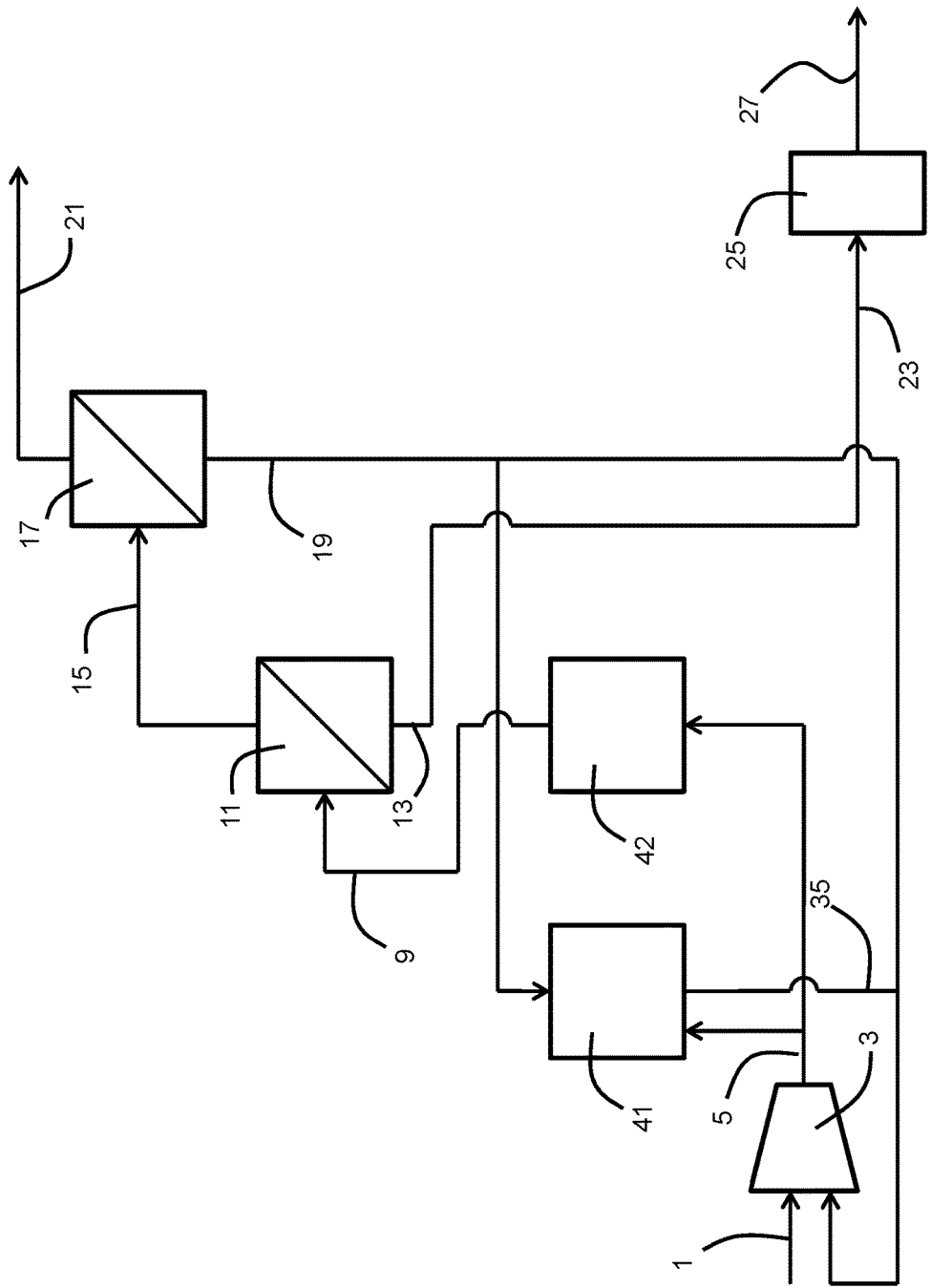

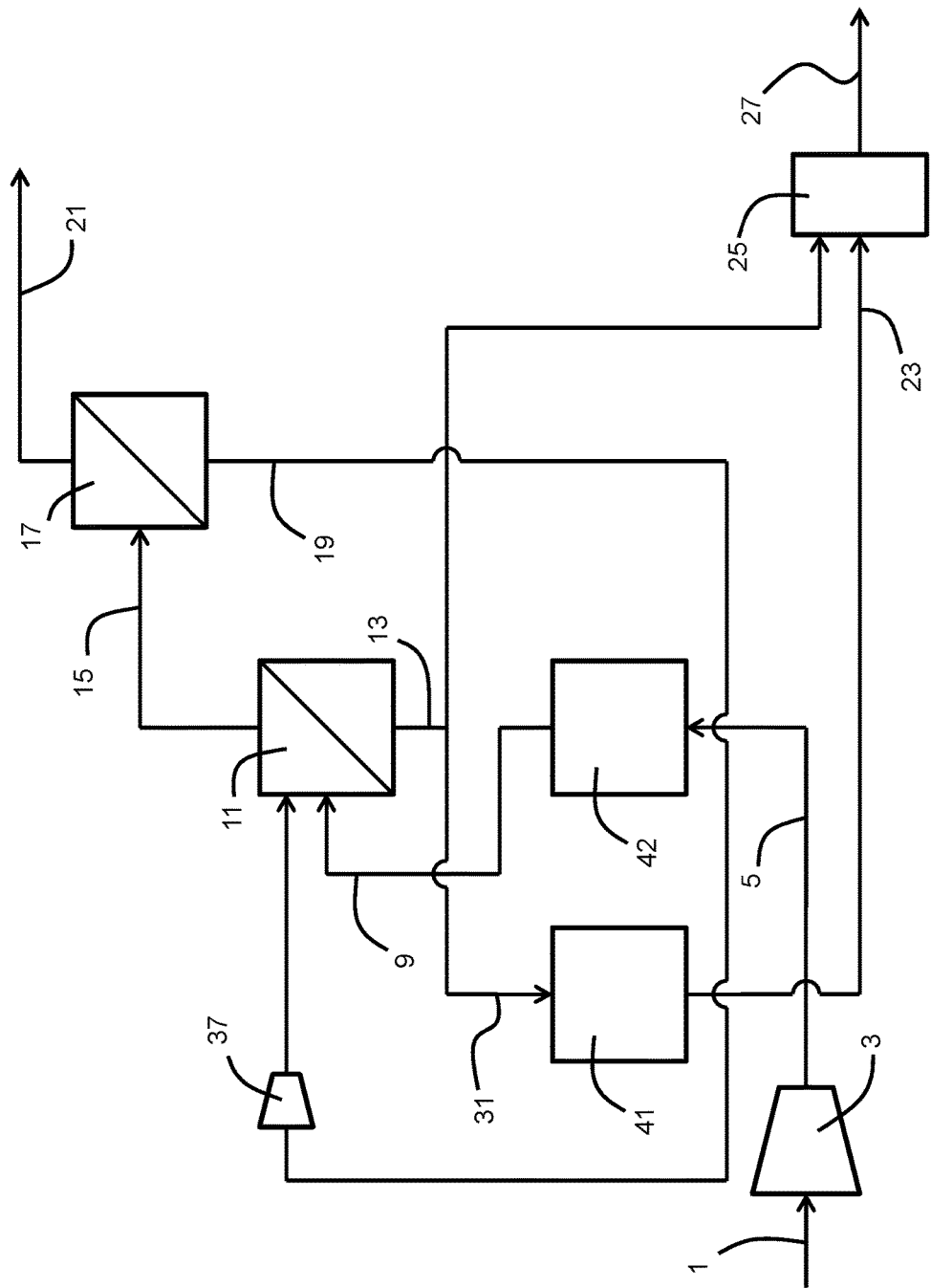

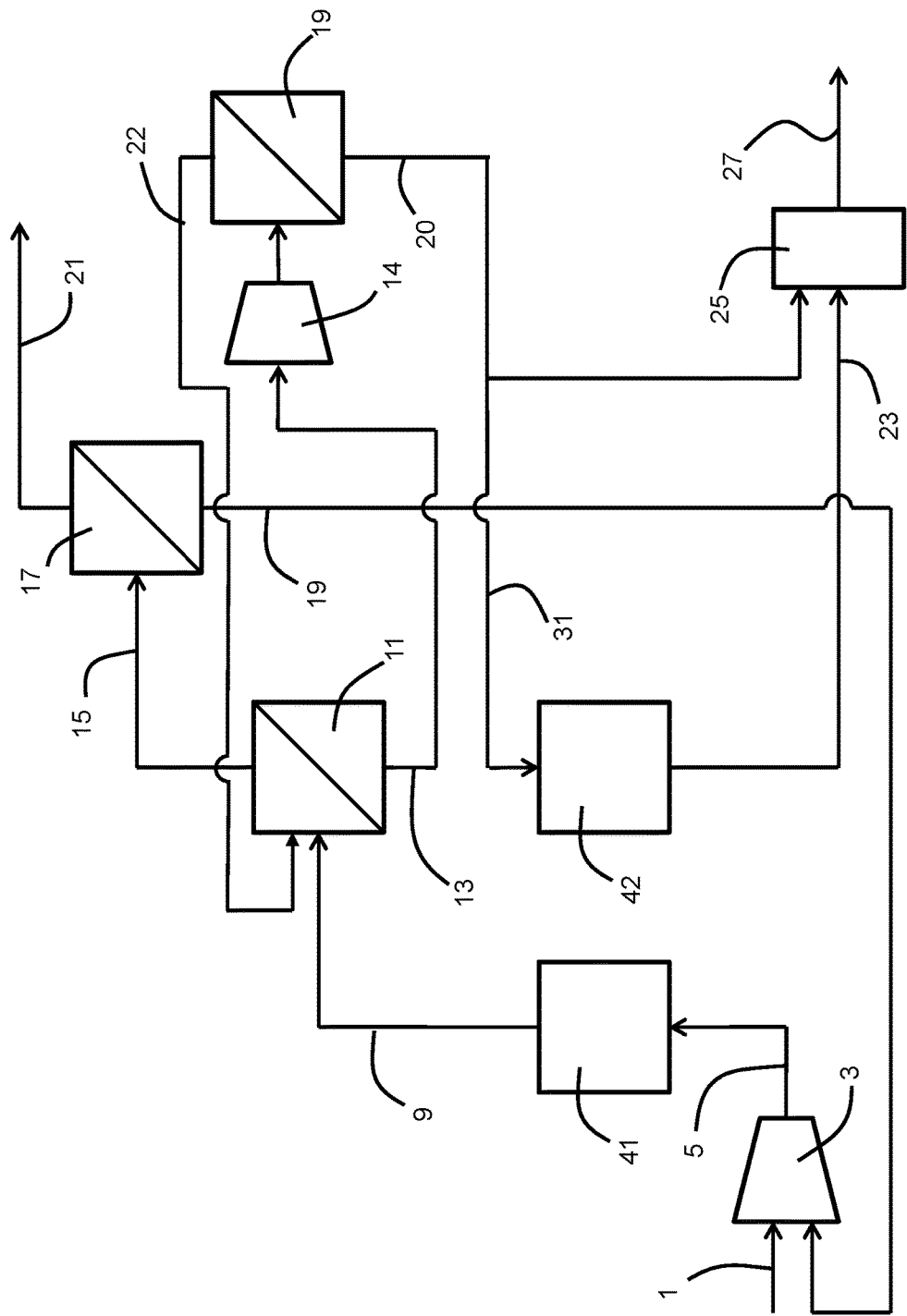

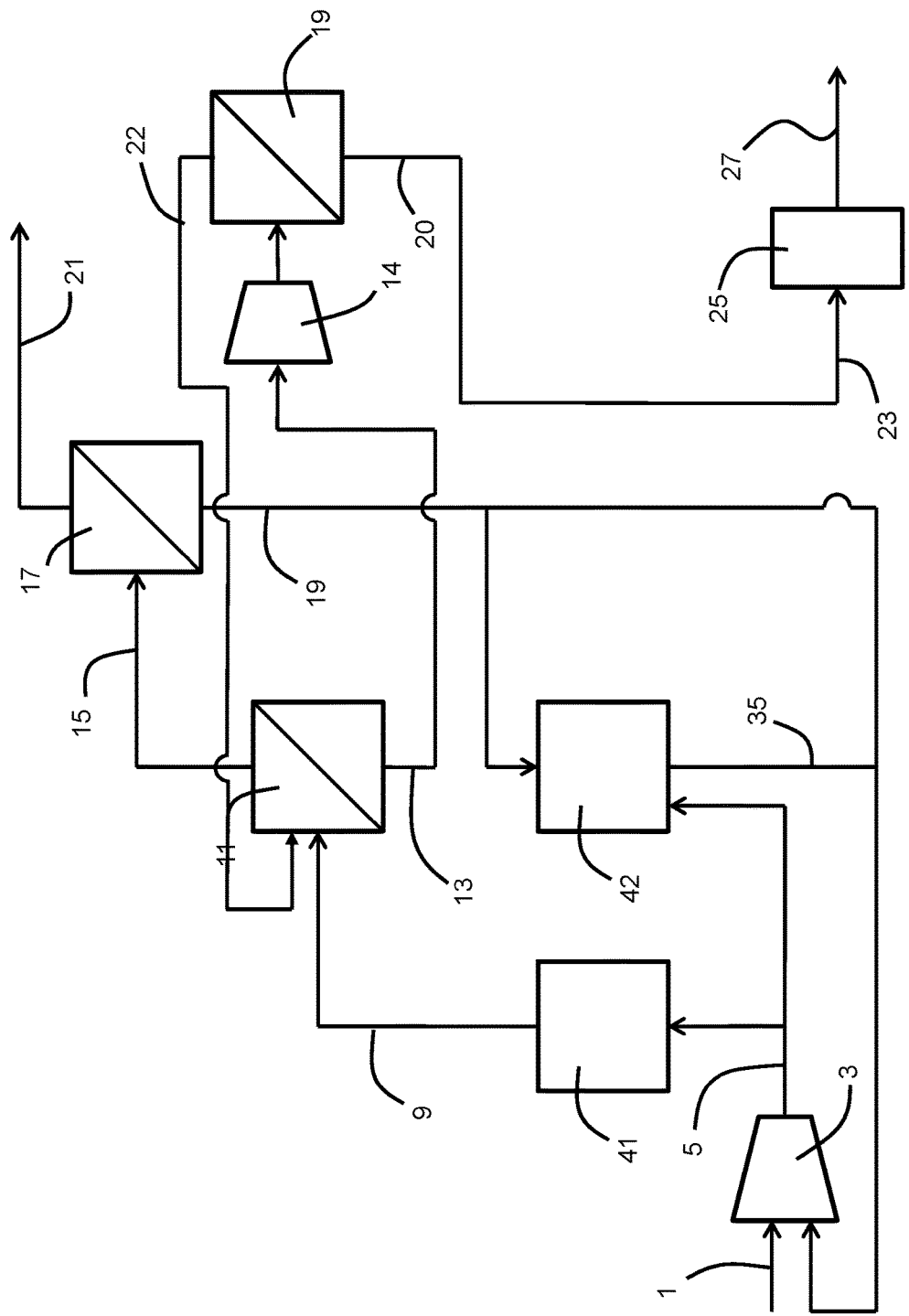

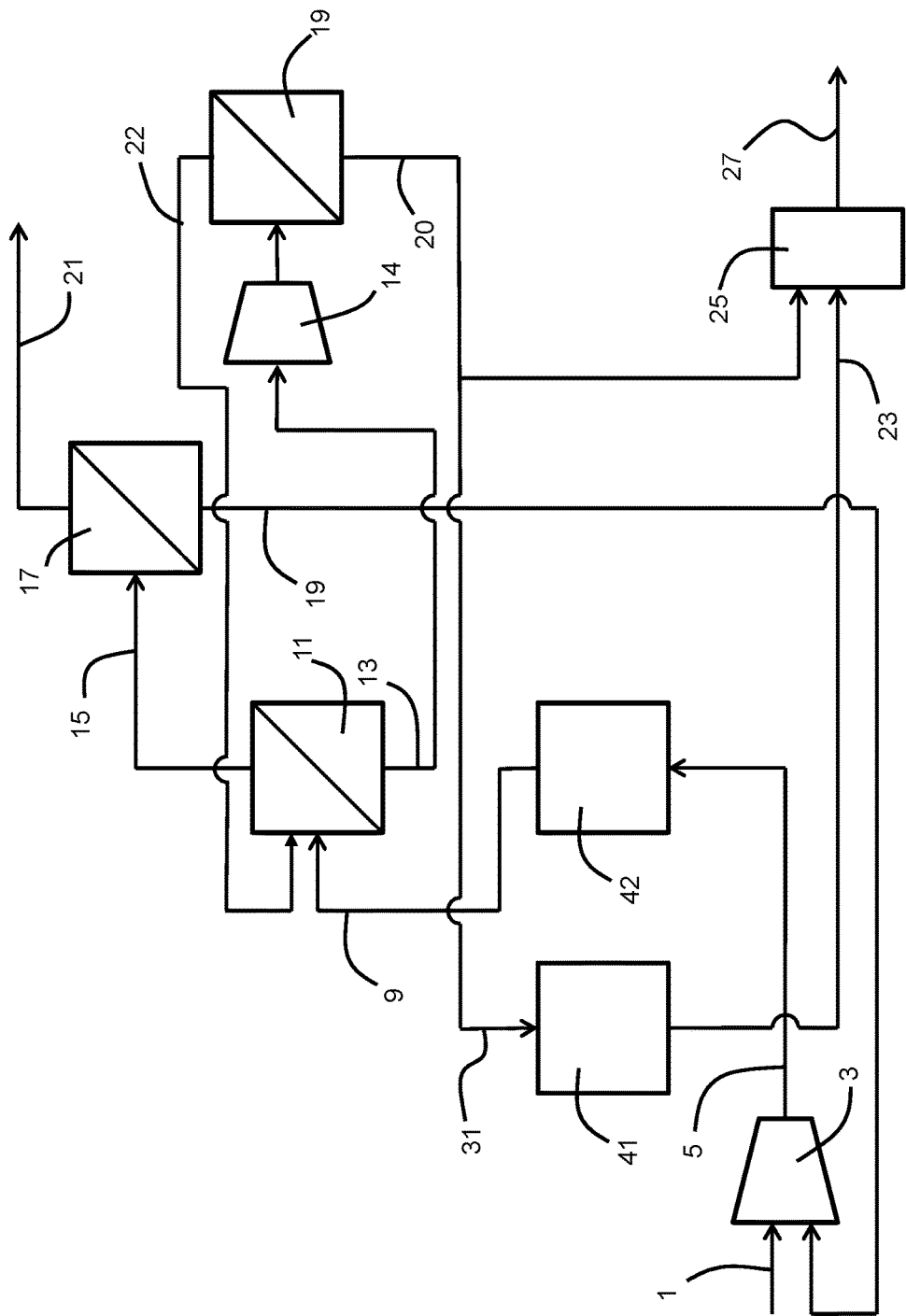
FIG 2C"

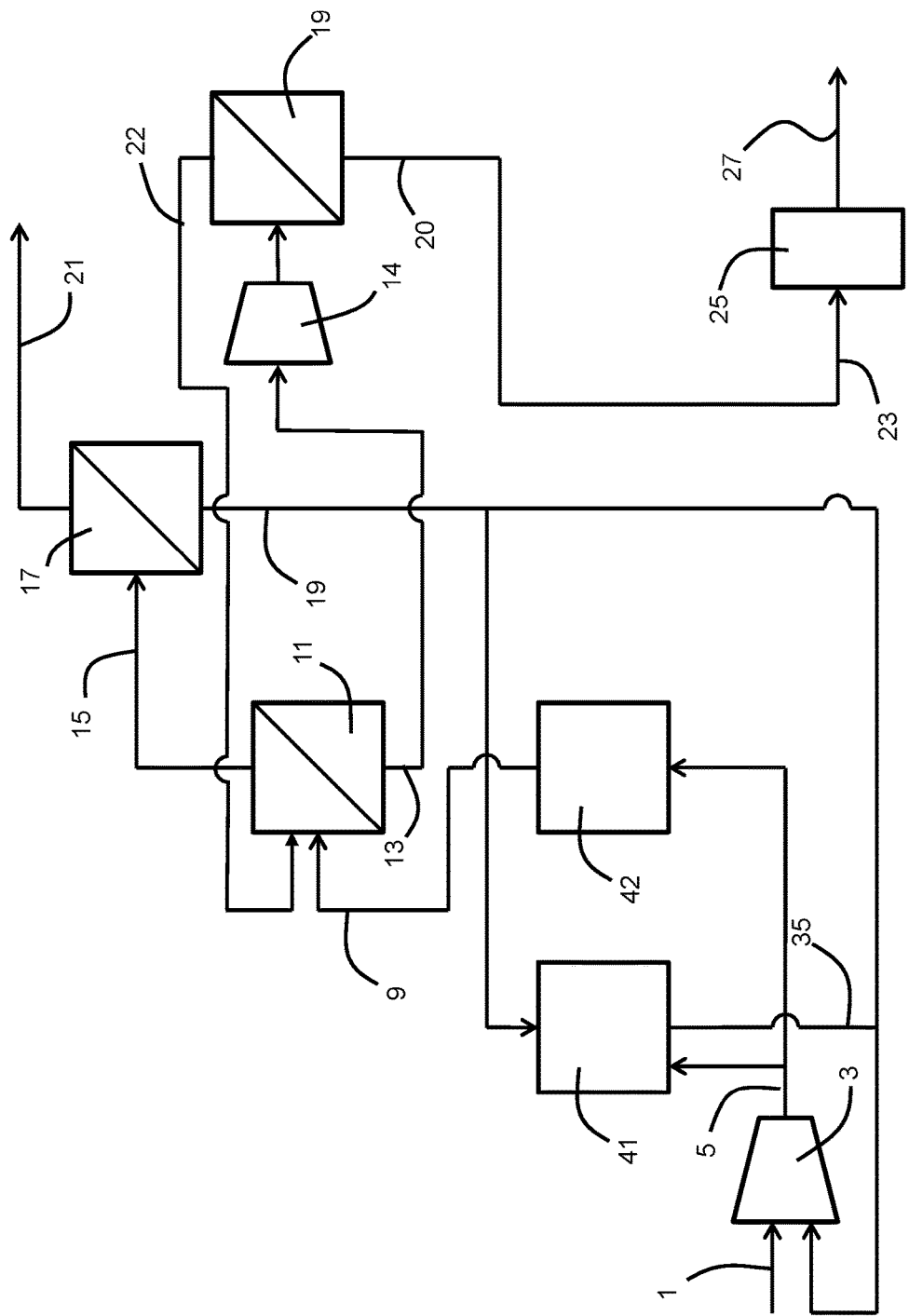
FIG 2D"

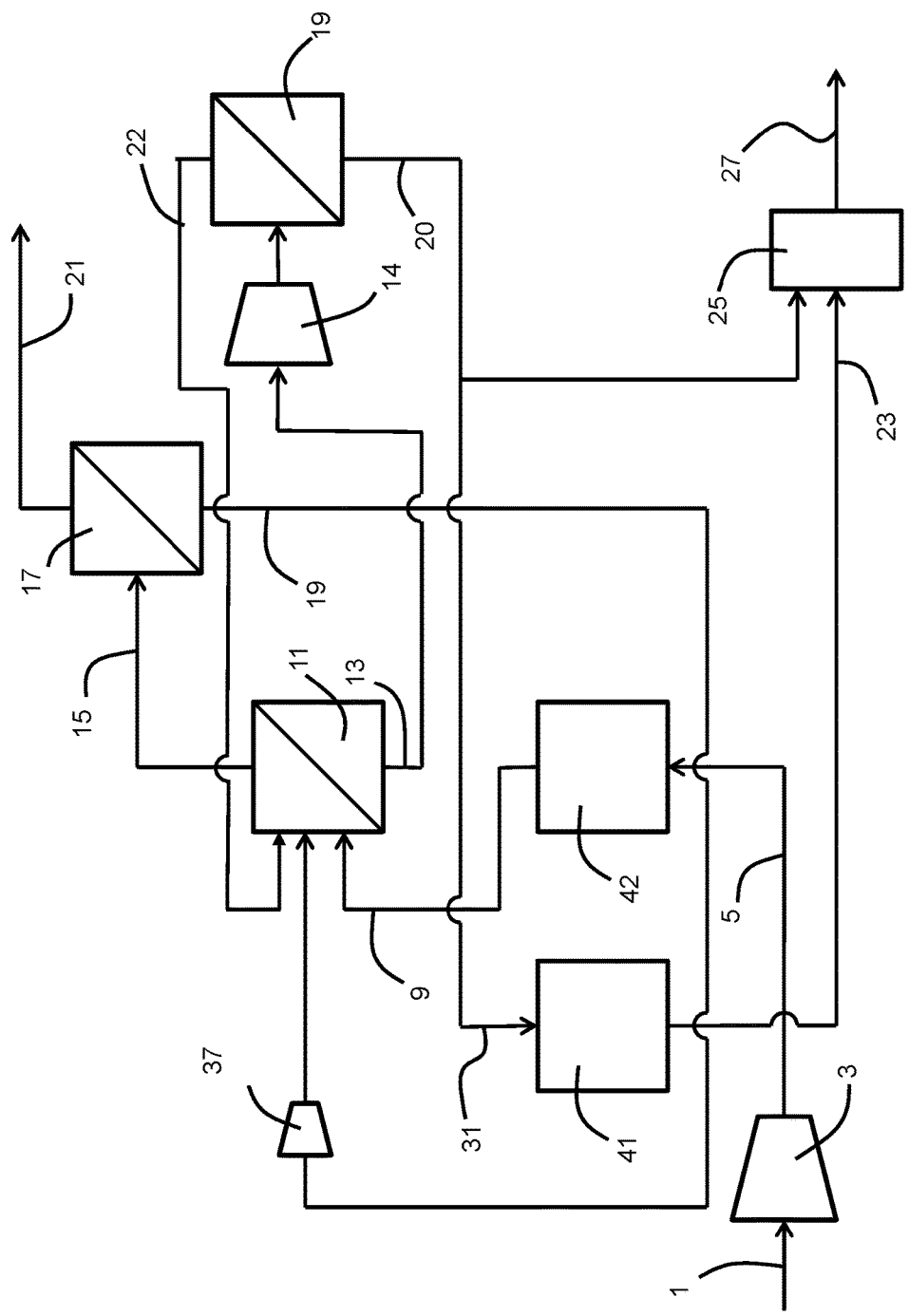

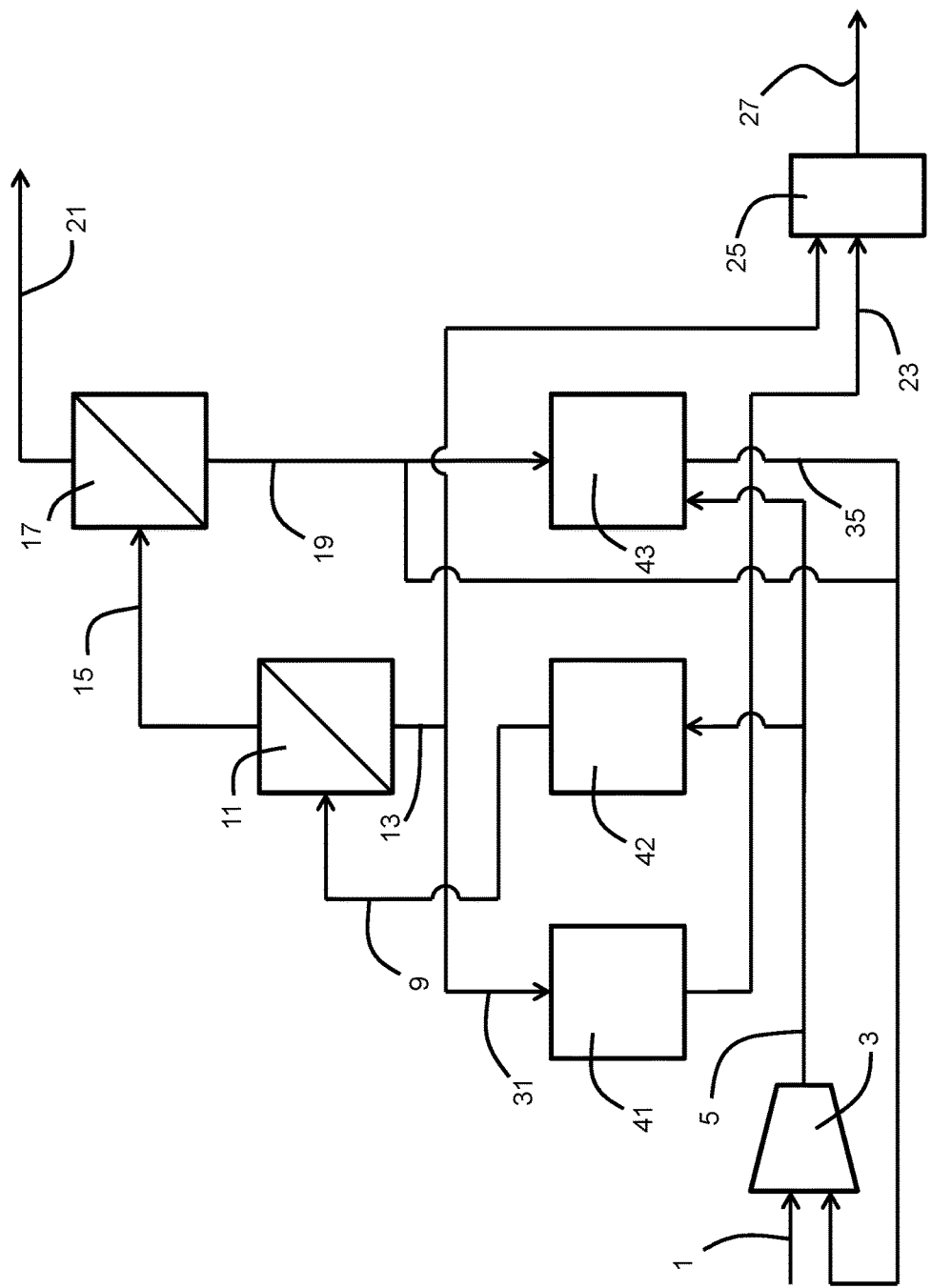

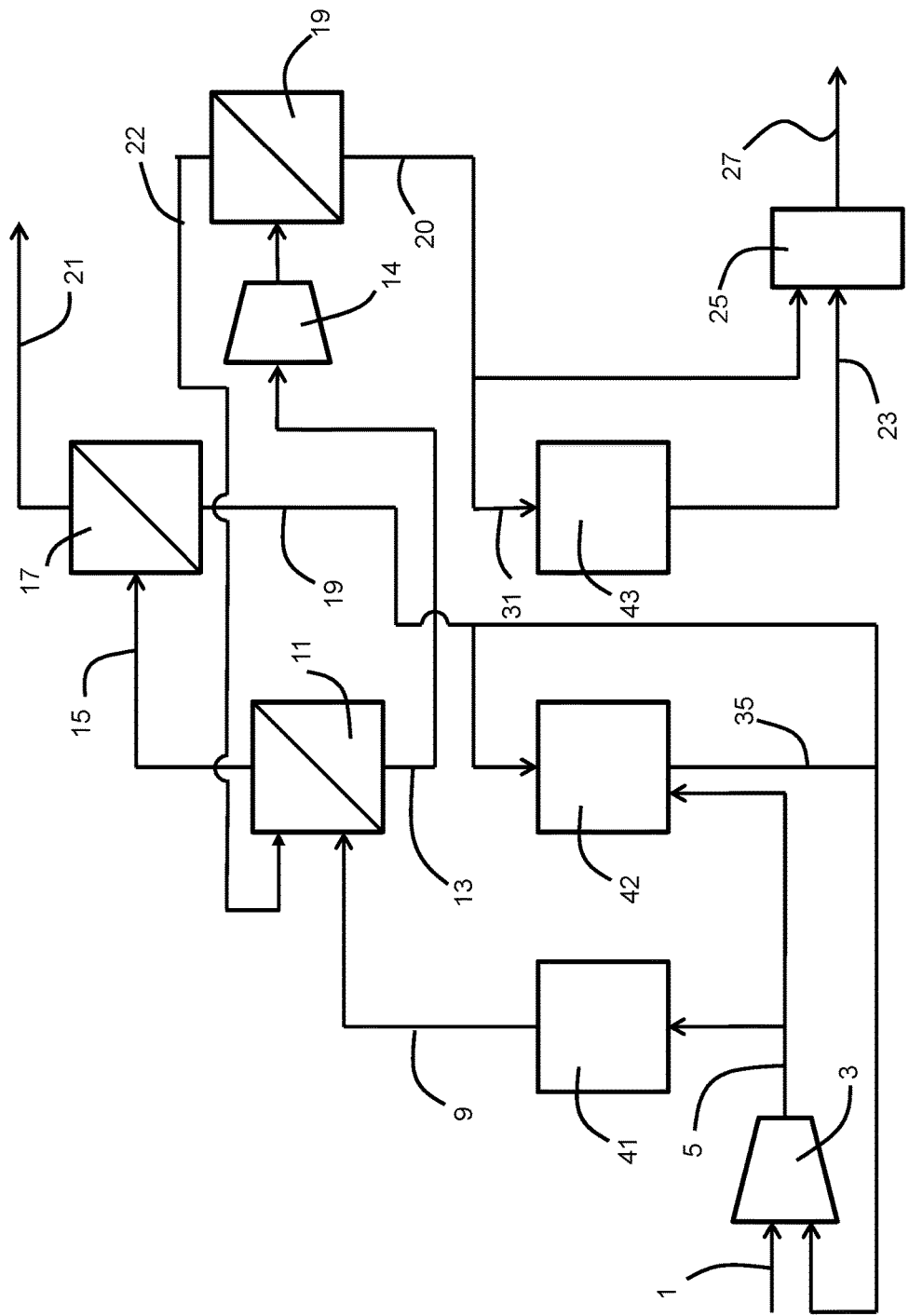
FIG 3A"

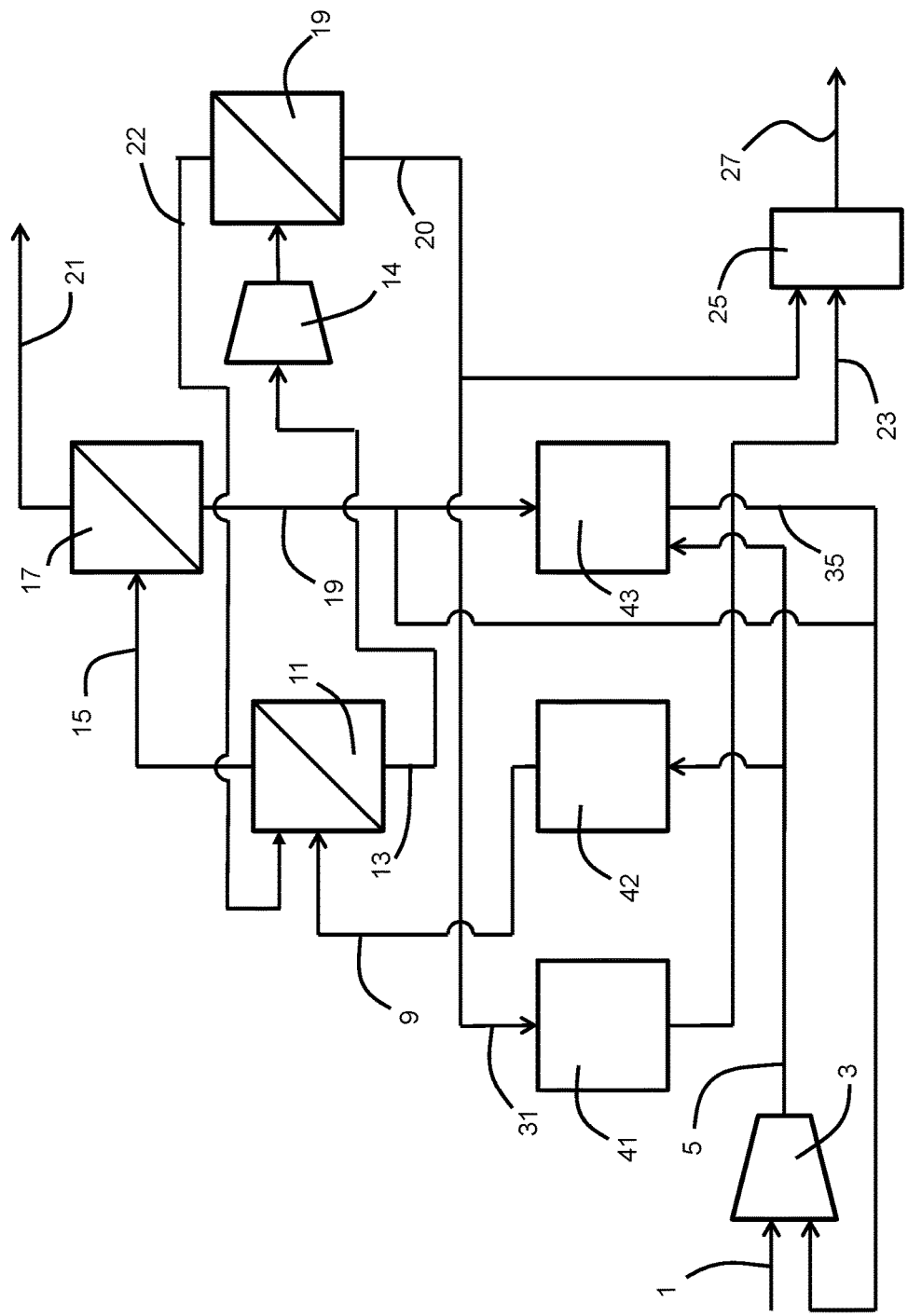

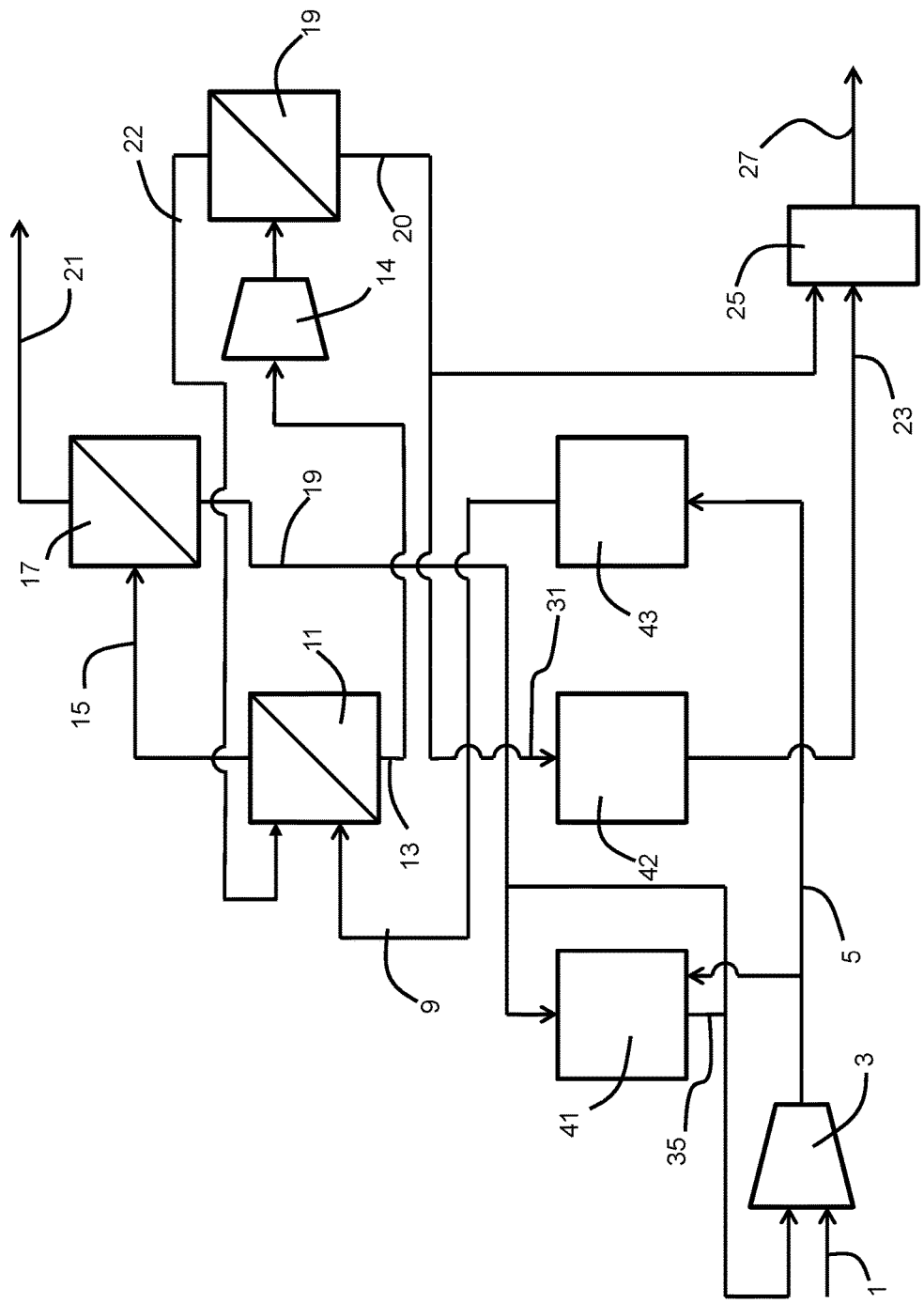
FIG 3C"

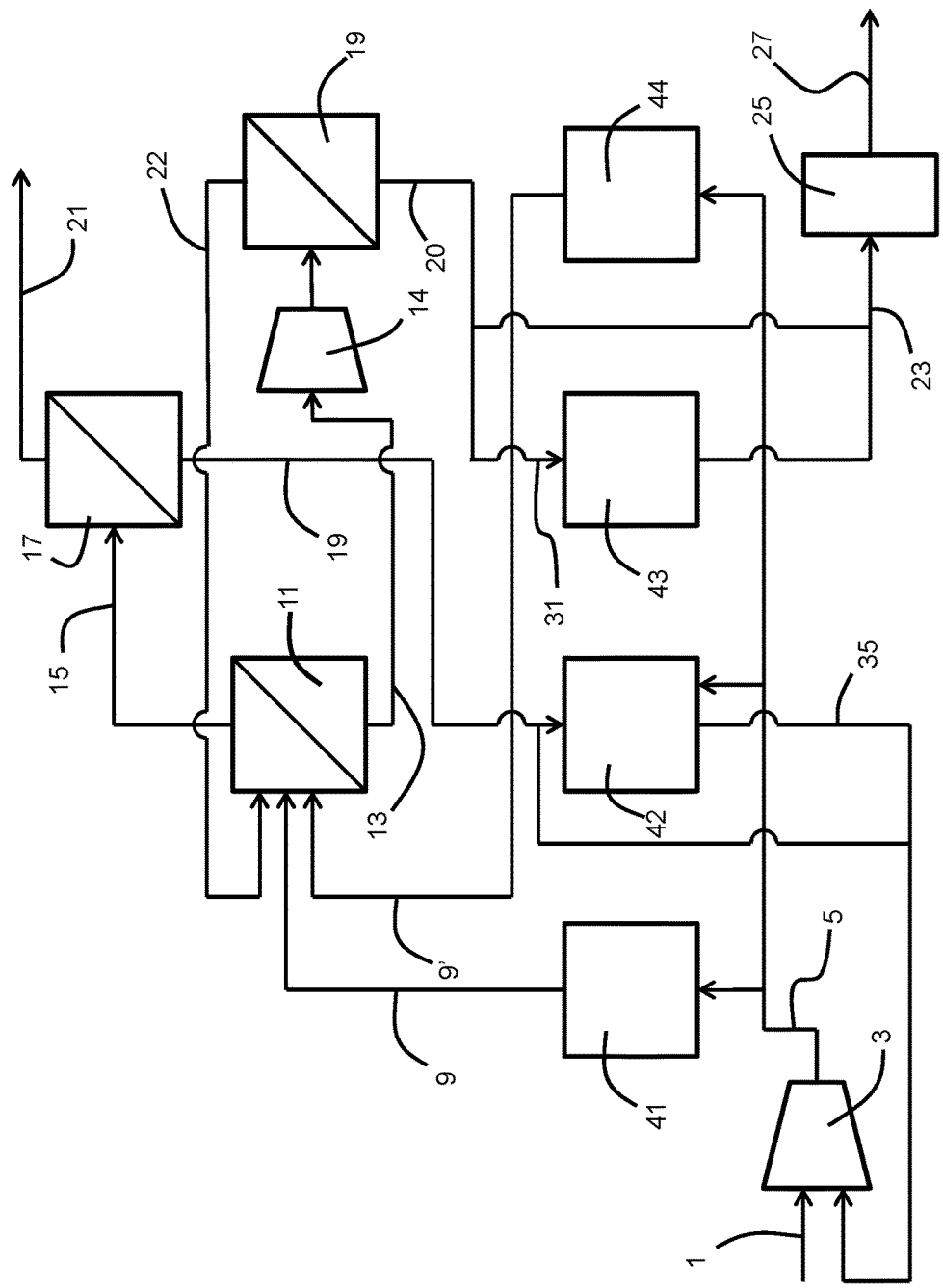
FIG 4A"

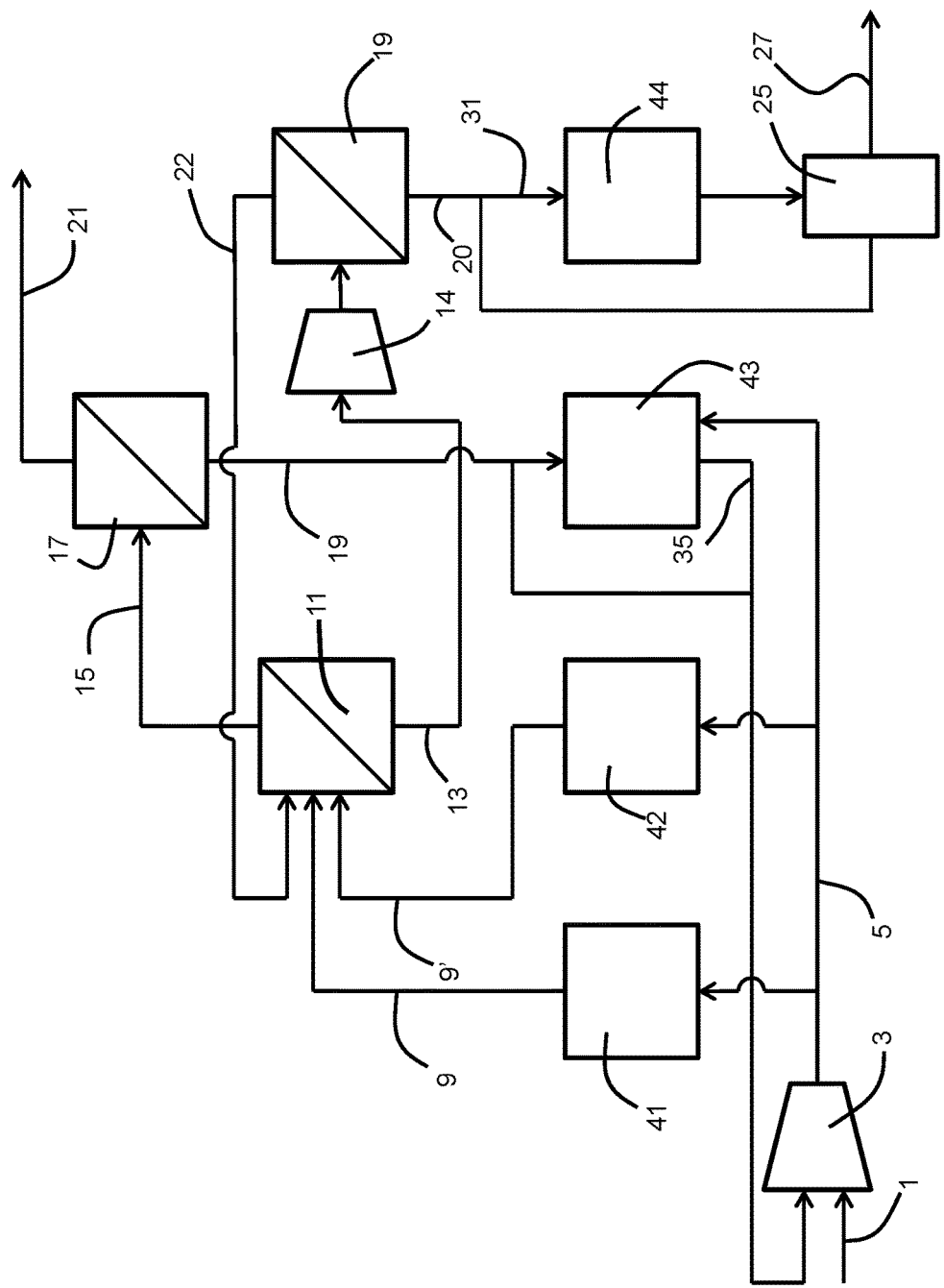
FIG 4B"

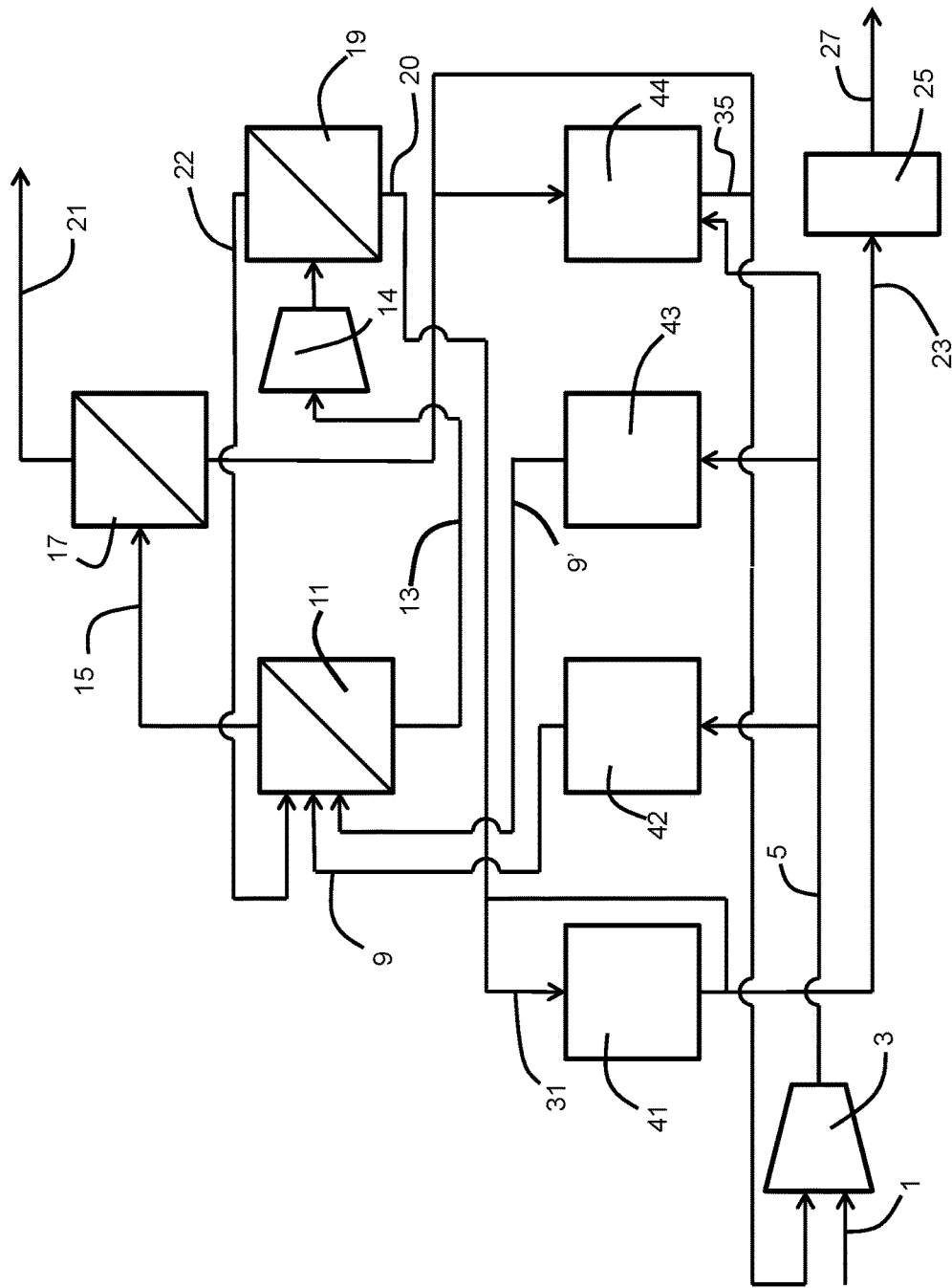
FIG 4C"

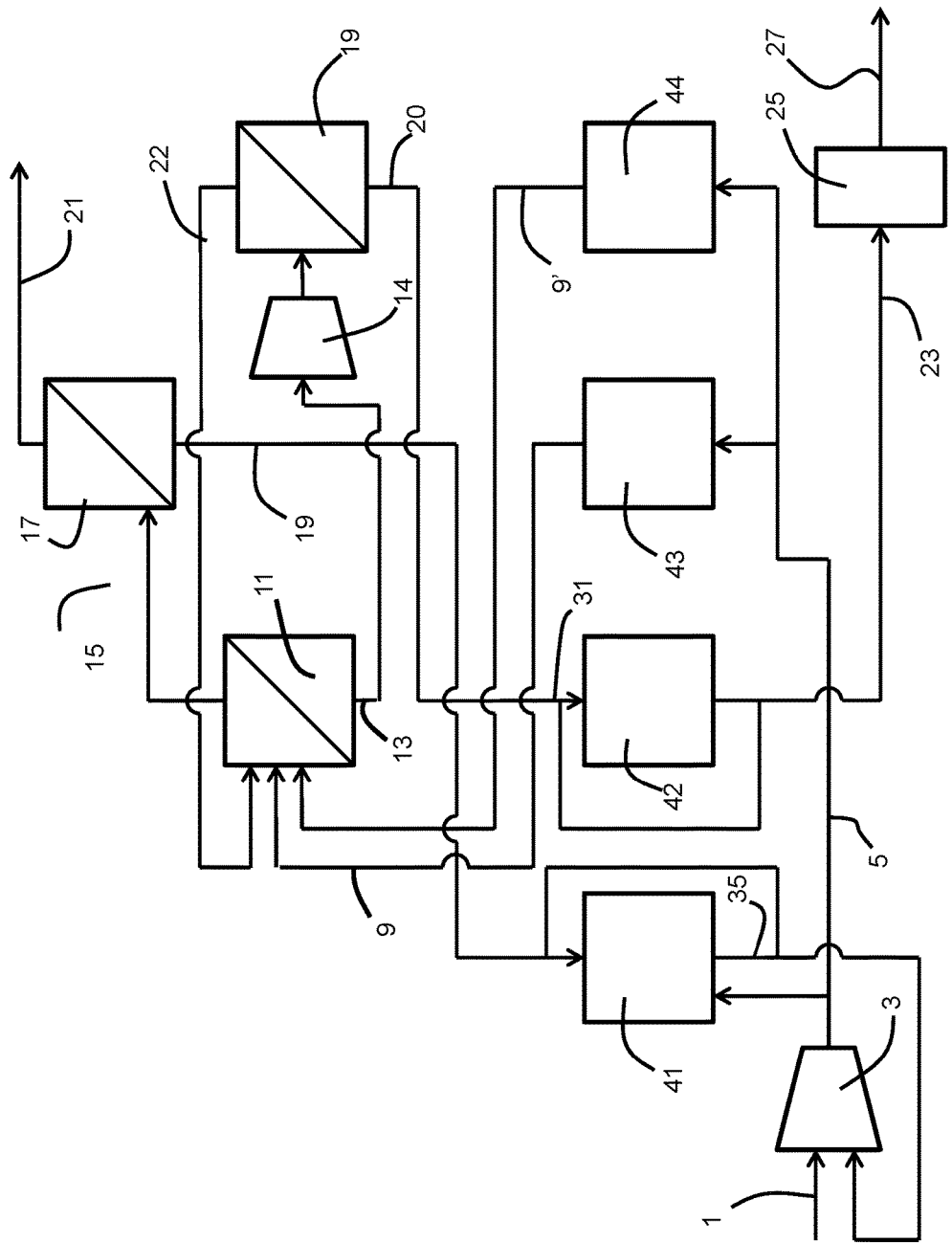
FIG 4D"

US 10,450,522 B2

INTEGRATED PTSA/MEMBRANE METHOD AND SYSTEM FOR H2S AND CO2 REMOVAL FROM BIOGAS

CROSS-REFERENCE TO RELATED APPLICATIONS

This application is a divisional of U.S. patent application Ser. No. 15/887,588, filed Feb. 2, 2018, now U.S. Pat. No. 10,179,883, which claims the benefit of U.S. Provisional Application No. 62/454,255, filed Feb. 3, 2017, which is being incorporated by reference herein in its entirety for all purposes.

BACKGROUND

Field of the Invention

The present invention relates to purification of biogas, in particular, of digester gas or landfill gas using an integrated gas separation system including TSA and membranes.

Related Art

Biogas contains impurities of $H_2S$, volatile organic compounds (VOCs), water, $CO_2$ and air. Removal of such impurities can yield nearly pure methane for sale as natural gas. Two typical types of biogas are landfill gas and digester gas. Landfill gas is obtained from a landfill where microorganisms convert waste primarily to methane and $CO_2$. Digesters anaerobically ferment agricultural, human waste, or other organic containing sources also resulting primarily in methane and $CO_2$. While the main constituents of biogas are methane and $CO_2$, they also include minor levels of water vapor, VOCs, $CO_2$, $H_2S$, and sometimes siloxanes (i.e., in landfill gas). The $H_2S$ present in biogas, especially for high $H_2S$ levels often found in digester gas, poses an economic and technical challenge because the product natural gas must meet requirements of relatively low $H_2S$ levels in order for it to be useful as a fuel or meet pipeline specifications. For example, while natural gas pipelines typically require an $H_2S$ level of 4 ppm (v/v) or less and a $CO_2$ level of 2% (v/v) or less, digester gas often contains $CO_2$ levels of 25-45% (v/v) and relatively high $H_2S$ levels of 100 ppm-1% (v/v).

Many technologies today are applied to upgrade digester gas including a patented (U.S. Pat. No. 7,025,803) purification system offered by Air Liquide Advanced Technologies, US. This system includes a pressure swing adsorption (PSA) unit followed by an activated carbon bed for water and VOC removal. The water and VOC-depleted gas is then fed to a two stage gas separation membrane unit for removal of $CO_2$. The first stage removes the bulk of the $CO_2$ present in the biogas. The $CO_2$ rich reject stream at low pressure from the first stage is used to regenerate the PSA unit to produce an impurity-laden $CO_2$ rich reject stream containing methane (lost from the feed gas via permeation through the membranes of the first stage), rejected $CO_2$ and desorbed VOCs and water. This stream is typically routed to a thermal oxidizer for destruction of the VOCs prior to venting. The methane rich second stage permeate is also at low pressure, so it is recycled to the suction inlet of the compressor upstream of the PSA unit. While this system has performed remarkably well, it does not satisfactorily handle relatively high levels of $H_2S$, and for that reason, a separate $H_2S$ removal system (such as SulfaTreat or other treatment method) may required for raw biogas containing relatively high $H_2S$ levels. Inclusion of the separate $H_2S$ removal system adds cost and complexity to the overall system.

A key advantage of the above-described Air Liquide system for treatment of biogas from landfills is removal by the membrane unit of a bulk of the $O_2$ in the biogas along with the $CO_2$. While pipeline specifications for $O_2$ may vary, a typical requirement is $O_2$ levels no higher than 0.2% (v/v). While biogas obtained from digesters should be $O_2$ free due to the anaerobic conditions of the digesters, digesters are low pressure operations that may allow of introduction of some amounts of air. Thus, some amount of $O_2$ is commonly encountered in digester-derived biogas.

Another digester gas upgrading system is offered by Guild Associates, Inc. One Guild system includes a PSA system that has the ability to adsorb $H_2O$, $H_2S$ and $CO_2$ in a single unit. A key attribute of this system is its ability to simultaneously adsorb and desorb $H_2S$, water and $CO_2$. However, this technology is limited for feeds containing $O_2$ and $N_2$ since the PSA unit enriches $O_2$ and $N_2$ in the product gas, typically by a factor of about 1.7× the feed gas concentration. Thus, for a product containing 2000 ppm $O_2$ (v/v), the raw gas fed to the PSA unit is limited to an $O_2$ level of only 1200 ppm (v/v). If the $O_2$ limit of the raw gas is exceeded, an additional process unit or units for removal of $O_2$ will be required. Inclusion of an additional process unit or units for removal of $O_2$ adds cost and complexity to the overall system.

Other PSA systems for digester gas upgrading have been proposed. However, many of such systems typically include a pretreatment system for $H_2S$ removal, thus adding cost and complexity.

Water-wash systems have been proposed for upgrading digester gas. Such systems include an air-stripped stream of water that is contacted over a packed bed against a rising feed stream. $CO_2$ present in the feed stream dissolves into the stream of water. The $CO_2$-laden water stream is subsequently let down in pressure and stripped with air for removal of the dissolved $CO_2$ derived from the feed stream. In water-wash system, amounts of $H_2S$ present in the feed stream may also be removed through dissolution in the water stream. In such a case, the regenerated stream is the stripping air plus the $CO_2$ and $H_2S$. As with the Guild system, $O_2$ and $N_2$ are not removed but instead are enriched in the product stream.

Similarly to the water-wash system, amine or physical solvent based upgrading systems have also been proposed for upgrading of biogas. In such systems, the solvent absorbs $CO_2$ and $H_2S$ present in the feed stream, and after pressure letdown, the solvent is regenerated by reboiling the solvent to drive off the previously absorbed $CO_2$ and $H_2S$. In other words, external stripping air is not used. For physical solvents, the reboiling can be reduced or in some cases eliminated and pressure letdown of the rich solvent may be used alone for regeneration. However, similar to the Guild system and water-wash systems, amine or physical solvent based systems enrich $O_2$ and $N_2$ in the product stream.

Thus, is an object to upgrade biogas, particularly digester gas, that includes $O_2$ and relatively high levels of $H_2S$ using a system that does not have an unnecessarily high cost or level of complexity.

SUMMARY

There is disclosed a biogas upgrading method based upon PTSA and gas separation membranes. The method includes the following steps. A stream of biogas is compressed with a main compressor. A PTSA feed gas stream withdrawn from an outlet of the main compressor is fed to a PTSA unit. $H_2S$ is removed from the PTSA feed gas stream with the PTSA unit. An $H_2S$-depleted PTSA product stream is withdrawn from the PTSA unit. The PTSA product stream is fed to a first gas separation membrane stage comprising one or more gas separation membranes selective for $CO_2$ and $O_2$ over methane. A first stage permeate stream enriched in $CO_2$ and $O_2$ and deficient in methane compared to the PTSA product stream and a first stage retentate stream deficient in $CO_2$ and $O_2$ and enriched in methane compared to the PTSA product stream are withdrawn from the first gas separation membrane stage. The first stage retentate stream is fed to a second gas separation membrane stage comprising one or more gas separation membranes selective for $CO_2$ and $O_2$ over methane. A second stage permeate stream enriched in $CO_2$ and deficient in methane compared to the first stage retentate stream and a second stage retentate stream deficient in $CO_2$ and enriched in methane compared to the first stage retentate stream are withdrawn from the second gas separation membrane stage. The second stage retentate stream is a product natural gas stream. Repressurization of the beds is performed with one or more of the PTSA feed gas stream, the PTSA product gas stream, the first stage retentate stream, and the second stage retentate stream. The PTSA unit comprises two or more adsorbent beds each of which is selective for water, VOCs, and $H_2S$ over $CO_2$ and for $H_2S$ over methane. Each of said beds is subjected to a PTSA cycle comprising the phases of: adsorption of water, VOCs, and $H_2S$ from the PTSA feed gas stream; depressurization; thermal regeneration using a regeneration gas stream in which adsorbed water, VOCs, and $H_2S$ are desorbed; cool down using a cool down gas stream; and repressurization.

There is also disclosed a biogas upgrading system based upon PTSA and gas separation membranes, comprising: a source of raw biogas comprising methane, $CO_2$, water, VOCs, and $H_2S$; a main compressor including a suction inlet in fluid communication with the source and receiving a stream of raw biogas from the source; a PTSA unit comprising two or more adsorbent beds each of which is selective for water, VOCs, and $H_2S$ over $CO_2$ and for $H_2S$ over methane, the PTSA unit being in downstream fluid communication with the main compressor and receiving a stream of a PTSA feed gas therefrom, the PTSA unit being adapted and configured to adsorb water, VOCs, and $H_2S$ from the PTSA feed gas and produce a PTSA product gas deficient in water, VOCs, and $H_2S$ in comparison to the PTSA feed gas; a first gas separation membrane stage comprising one or more gas separation membranes selective for $CO_2$ and $O_2$ over methane, a feed gas inlet of the first gas separation membrane stage being in downstream fluid communication with the PTSA unit, the first gas separation membrane stage being configured and adapted to separate the PTSA product gas into a first stage permeate gas stream and a first stage retentate gas stream; a second gas separation membrane stage comprising one or more gas separation membranes selective for $CO_2$ and $O_2$ over methane, a feed gas inlet of the second gas separation membrane stage being in downstream fluid communication with the retentate outlet of the first gas separation membrane stage and receiving the first stage permeate gas stream therefrom, the second gas separation membrane stage being adapted and configured to separate the first retentate gas stream into a second permeate gas stream and a second retentate gas stream; and a treatment unit in downstream fluid communication with the PTSA unit so as to receive a waste gas from the PTSA comprised of the thermal regeneration gas and water, VOCs, and $H_2S$, the treatment unit being adapted and configured to either oxidize or burn the VOCs contained in the waste gas. The PTSA unit is in fluid communication with the permeate gas outlet of the first gas separation membrane stages so as to receive a flow of the first stage permeate gas for use as a thermal regeneration gas to thermally regenerate and desorb water, VOCs, and $H_2S$ that was adsorbed upon the adsorbent beds from the PTSA feed gas stream. The PTSA unit is in fluid communication with the permeate gas outlet of the second gas separation membrane stage so as to receive a flow of the second permeate gas stream for use as a cool down stream for cooling one or more adsorbent beds after thermal regeneration thereof; and The method and/or system may include one or more of the following aspects:

- the compressed feed gas is cooled prior to introduction to the PTSA.
- some or all of the second stage permeate stream is the cool down gas stream and the cool down gas stream is received from the PTSA unit by a suction inlet of the main compressor where it is combined with the compressed biogas stream.
- the second stage permeate stream is received at and compressed by a secondary compressor and the compressed second stage permeate stream is fed to the first gas separation stage along with the PTSA product stream.
- a waste gas comprised of the regeneration gas stream and the $H_2S$, water, and VOCs desorbed from one or more adsorbent beds of the PTSA unit is thermally oxidized at a thermal oxidizer.
- the regeneration gas stream is comprised of some or all of the first stage permeate stream which has been heated to a temperature above the PTSA feed gas temperature.
- a waste gas stream comprised of the regeneration gas stream and the $H_2S$, water, and VOCs desorbed from one or more adsorbent beds of the PTSA unit is thermally oxidized at a thermal oxidizer.
- some or all of the second stage permeate stream is the cool down gas stream and the cool down gas stream is received from the PTSA unit at a suction inlet of the main compressor where it is combined with the compressed biogas stream
- amounts of $H_2S$ present in the PTSA feed gas stream are removing by an $H_2S$ removal unit prior to feeding the PTSA feed gas stream to the PTSA unit, wherein the PTSA unit removes amounts of water and VOCs from the PTSA feed gas stream and also amounts of the $H_2S$ remaining in the PTSA feed gas stream after treatment by the $H_2S$ removal unit.
- the regeneration gas stream is heated to the temperature above the PTSA feed gas temperature through heat exchange, at a heat exchanger, with cooling oil circulating through the first compressor.
- some or all of the regeneration gas stream is the first stage permeate stream.
- a waste gas comprised of the regeneration gas stream and the $H_2S$, water, and VOCs desorbed from one or more adsorbent beds of the PTSA unit is thermally oxidized at a thermal oxidizer and the regeneration gas stream is heated to the temperature above the PTSA feed gas temperature through heat exchange, at a heat exchanger, with hot gas produced in the thermal oxidizer.
- the PTSA unit comprises first and second adsorbent beds, and the PTSA unit cycle comprises: a first phase during which the first bed undergoes adsorption and the second bed undergoes depressurization and then thermal regeneration; a second phase during which the first bed undergoes adsorption and the second bed undergoes cool down and then repressurization; a third phase during which the second bed undergoes adsorption and the first bed undergoes depressurization and then thermal regeneration; and a fourth phase during which the second bed undergoes adsorption and the first bed undergoes cool down and then repressurization.

the PTSA unit comprises first, second, and third adsorbent beds, and the PTSA unit cycle comprises: a first phase during which the first bed undergoes adsorption, the second bed undergoes cool down and then repressurization, and the third bed undergoes depressurization and then thermal regeneration; a second phase during which the second bed undergoes adsorption, the third bed undergoes cool down and then repressurization, and the first bed undergoes depressurization and then thermal regeneration; and a third phase during which the third bed undergoes adsorption, the first bed undergoes cool down and then repressurization, and the second bed undergoes depressurization and then thermal regeneration.

the PTSA unit comprises first, second, third, and fourth adsorbent beds, and the PTSA unit cycle comprises: a first phase during which the first and fourth beds undergo adsorption, the second bed undergoes cool down and then repressurization, and the third bed undergoes depressurization and then thermal regeneration; a second phase during which the first and second beds undergo adsorption, the third bed undergoes cool down and then repressurization, and the fourth bed undergoes depressurization and then thermal regeneration; a third phase during which the second and third beds undergo adsorption, the fourth bed undergoes cool down and then repressurization, and the first bed undergoes depressurization and then thermal regeneration; and a fourth phase during which the third and fourth beds undergo adsorption, the first bed undergoes cool down and then repressurization, and the second bed undergoes depressurization and then thermal regeneration.

the suction inlet of the main compressor is in fluid communication with the PTSA unit so as to receive the cool down gas stream from the PTSA unit and allow combination and compression with the raw biogas stream.

a secondary compressor including a suction inlet is in fluid communication with the PTSA unit so as to receive the cool down gas stream from the PTSA, wherein the feed gas inlet of the first gas separation membrane stage is in downstream fluid communication with an outlet of the secondary compressor so as to receive the cool down gas stream after compression by the secondary compressor and separate a combined feed of the cool down gas stream and the PTSA product gas into the first stage permeate gas stream and a first stage retentate gas stream.

the main compressor includes an oil cooling circuit including a heat exchanger adapted and configured to exchange heat between the first stage permeate and oil flowing in the cooling circuit so as to heat the first stage permeate to the temperature at which thermal regeneration of the adsorbent beds is to take place.

a $H_2S$ removal unit is in flow communication between the main compressor and the PTSA unit, the $H_2S$ removal unit being adapted and configured to remove amounts of $H_2S$ present in the PTSA feed gas stream prior to feeding the PTSA feed gas stream to the PTSA unit, wherein the PTSA unit is adapted and configured to remove amounts of water and VOCs from the PTSA feed gas stream and also amounts of the $H_2S$ remaining in the PTSA feed gas stream after treatment by the $H_2S$ removal unit.

a heat exchanger is adapted and configured to exchange heat between hot gas from the treatment unit and the regeneration gas stream so as to heat the regeneration gas stream to the temperature above the PTSA feed gas temperature.

BRIEF DESCRIPTION OF THE DRAWINGS

For a further understanding of the nature and objects of the present invention, reference should be made to the following detailed description, taken in conjunction with the accompanying drawings, in which like elements are given the same or analogous reference numbers and wherein:

FIG. 1' is a schematic of another general embodiment of the method and system of the invention.

FIG. 1" is a schematic of another general embodiment of the method and system of the invention.

FIG. 1''' is a schematic of another general embodiment of the method and system of the invention.

FIG. 2C is a schematic of a third phase of the first two-bed embodiment of the method and system of the invention.

FIG. 2A' is a schematic of a first phase of a second two-bed embodiment of the method and system of the invention.

FIG. 2B' is a schematic of a second phase of the second two-bed embodiment of the method and system of the invention.

FIG. 2C' is a schematic of a third phase of the second two-bed embodiment of the method and system of the invention.

FIG. 2D' is a schematic of a third phase of the second two-bed embodiment of the method and system of the invention.

FIG. 2A" is a schematic of a first phase of a third two-bed embodiment of the method and system of the invention.

FIG. 2B" is a schematic of a second phase of the third two-bed embodiment of the method and system of the invention.

FIG. 2C" is a schematic of a third phase of the third two-bed embodiment of the method and system of the invention.

FIG. 2D" is a schematic of a fourth phase of the third two-bed embodiment of the method and system of the invention.

FIG. 2A''' is a schematic of a first phase of a fourth two-bed embodiment of the method and system of the invention.

FIG. 2B''' is a schematic of a second phase of the fourth two-bed embodiment of the method and system of the invention.

FIG. 2C''' is a schematic of a third phase of the fourth two-bed embodiment of the method and system of the invention.

FIG. 2D''' is a schematic of a fourth phase of the fourth two-bed embodiment of the method and system of the invention.

FIG. 3A' is a schematic of a first phase of a second three-bed embodiment of the method and system of the invention.

FIG. 3B' is a schematic of a second phase of the second three-bed embodiment of the method and system of the invention.

FIG. 3C' is a schematic of a third phase of the second three-bed embodiment of the method and system of the invention.

FIG. 3A'' is a schematic of a first phase of a third three-bed embodiment of the method and system of the invention.

FIG. 3B'' is a schematic of a second phase of the third three-bed embodiment of the method and system of the invention.

FIG. 3C'' is a schematic of a third phase of the third three-bed embodiment of the method and system of the invention.

FIG. 3A''' is a schematic of a first phase of a fourth three-bed embodiment of the method and system of the invention.

FIG. 3B''' is a schematic of a second phase of the fourth three-bed embodiment of the method and system of the invention.

FIG. 3C''' is a schematic of a third phase of the fourth three-bed embodiment of the method and system of the invention.

FIG. 4A' is a schematic of a first phase of a second four-bed embodiment of the method and system of the invention.

FIG. 4B' is a schematic of a second phase of the second four-bed embodiment of the method and system of the invention.

FIG. 4C' is a schematic of a third phase of the second four-bed embodiment of the method and system of the invention.

FIG. 4D' is a schematic of a fourth phase of the second four-bed embodiment of the method and system of the invention.

FIG. 4A'' is a schematic of a first phase of a third four-bed embodiment of the method and system of the invention.

FIG. 4B'' is a schematic of a second phase of the third four-bed embodiment of the method and system of the invention.

FIG. 4C'' is a schematic of a third phase of the third four-bed embodiment of the method and system of the invention.

FIG. 4D'' is a schematic of a third phase of the third four-bed embodiment of the method and system of the invention.

FIG. 4A''' is a schematic of a first phase of a fourth four-bed embodiment of the method and system of the invention.

FIG. 4B''' is a schematic of a second phase of the fourth four-bed embodiment of the method and system of the invention.

FIG. 4C''' is a schematic of a third phase of the fourth four-bed embodiment of the method and system of the invention.

FIG. 4D''' is a schematic of a third phase of the fourth four-bed embodiment of the method and system of the invention.

DESCRIPTION OF PREFERRED EMBODIMENTS

Figure 1:
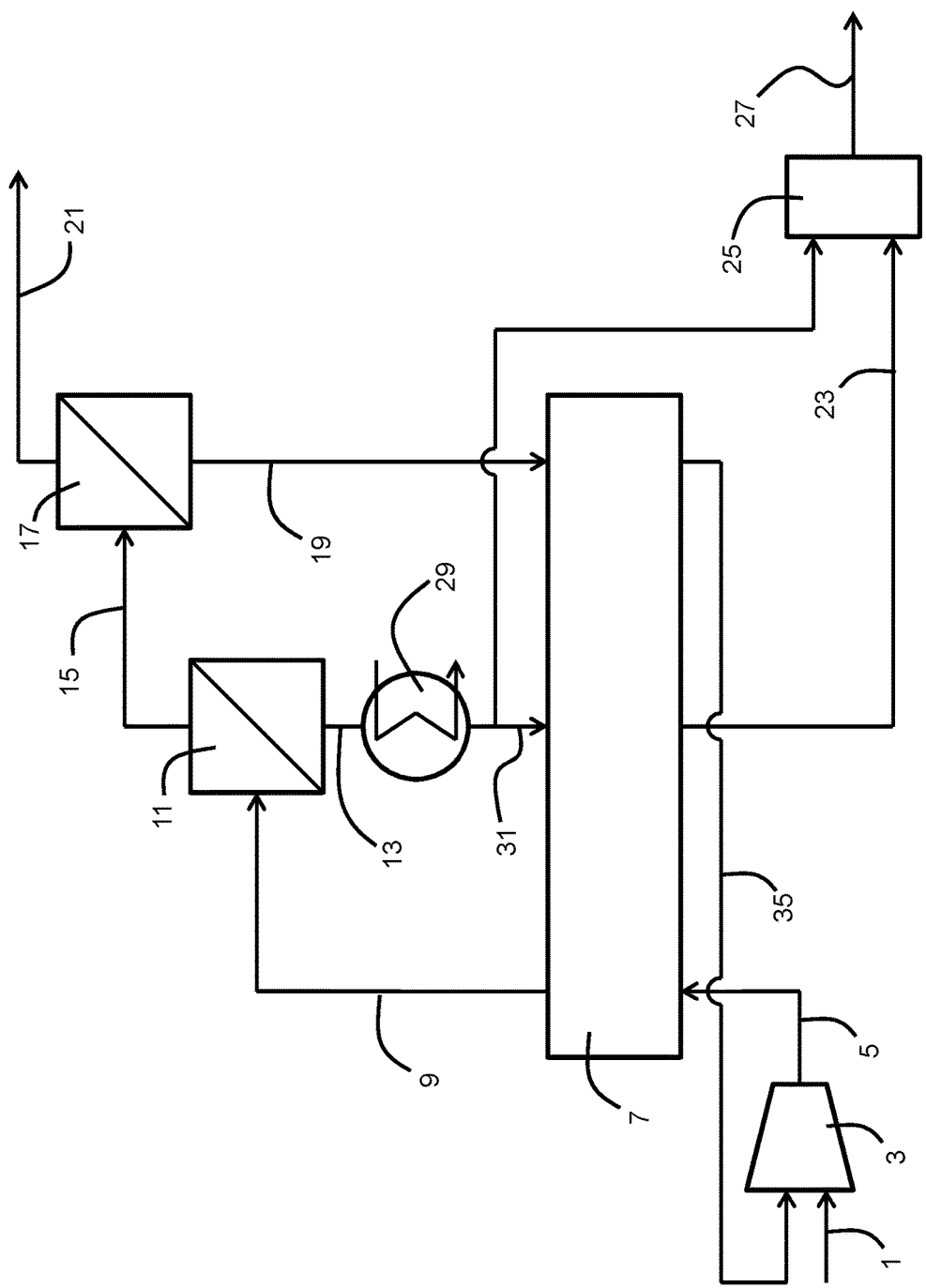
FIG. 1 is a schematic of one general embodiment of the method and system of the invention.
Figure 1:
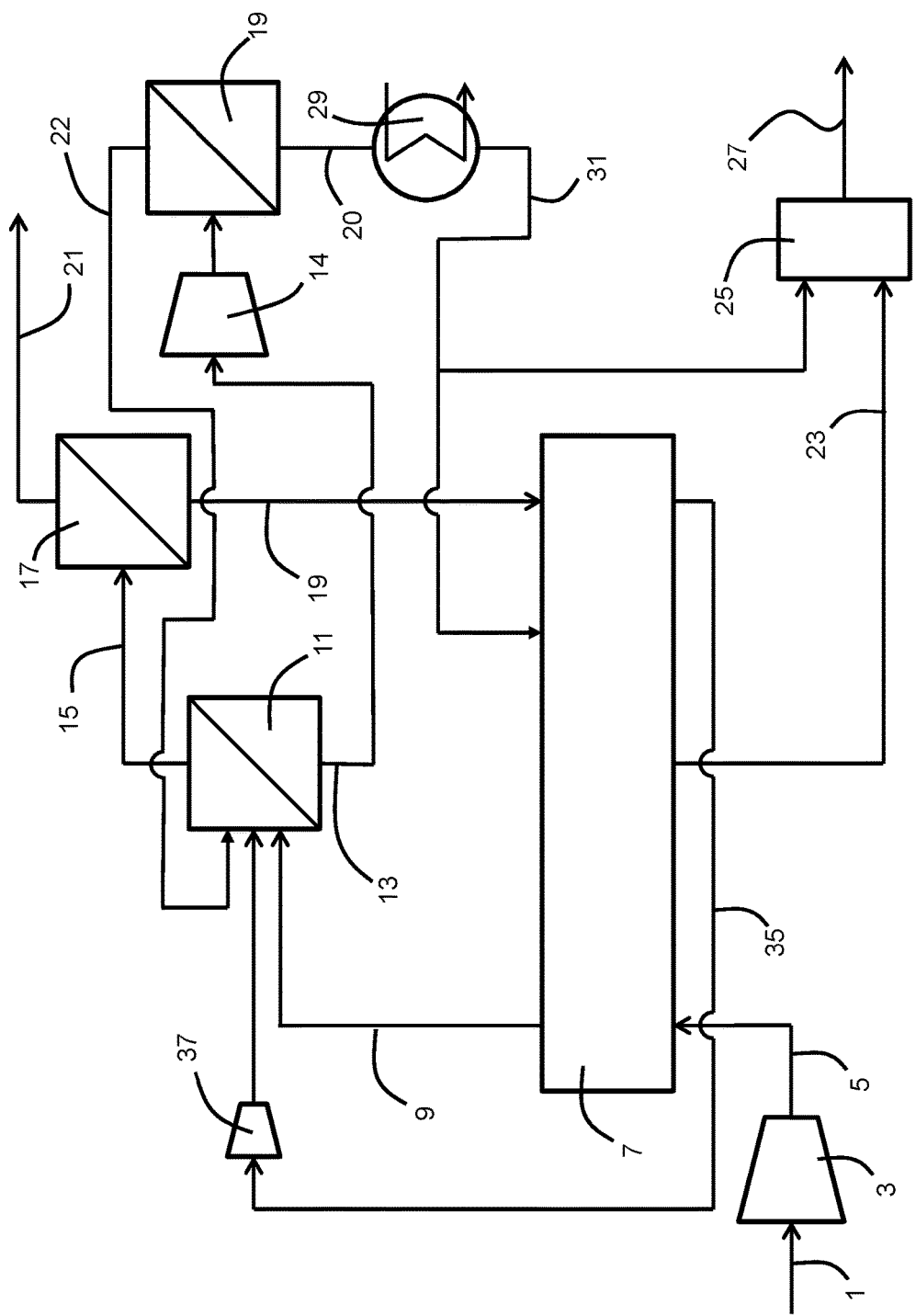

The invention is a hybrid PTSA/membrane method system for upgrading of biogas. It removes amounts of $H_2S$, water, VOCs, and $CO_2$ to yield a product gas meeting natural gas specifications. The $H_2S$ content of the product gas is no more than 100 ppm (v/v) for on-site use in generators or no more than 4 ppm (v/v) for meeting typical pipeline specifications for sale. For pipeline quality natural gas, the $H_2S$ level in the product gas may alternatively expressed as no more than 1 grain per 100 stdft$^3$, typically no more than 0.3 grain per 100 stdft$^3$. The product gas also contains no more than 0.4%, typically no more than 0.2% (v/v) of $O_2$, and no more than 2% (v/v) of $CO_2$.

The biogas may be obtained from a landfill or an anaerobic digester.

The composition of the raw landfill gas may vary but typically includes 40-60% (v/v) methane, 40-60% (v/v) $CO_2$, 2-15% (v/v) $N_2$, 0.1-1% (v/v) $O_2$, 0.001-0.3% $NH_3$ (v/v), 0.01-0.5 VOCs (excluding methane), and sometimes up to 1% (v/v) total sulfur compounds, up to 0.2% (v/v) $H_2$, up to 0.2% (v/v) CO, and varying levels of siloxanes. The $H_2S$ content can vary as widely as 50 ppm (v/v) to 15,000 ppm (v/v) but more typically is present at levels of 100 ppm (v/v) or less.

The composition of the digester gas may vary depending upon the type of waste processed, such as animal waste, food processing waste, or sewage. Digester gas typically contains 55-70% (v/v) methane and 25-45% (v/v) $CO_2$. It also includes water at or near its dew point, 3-4 ppm (v/v) $NH_3$, and up to 50 ppm (v/v) siloxanes. The $H_2S$ content of digester gas can reach as high as 10,000 ppm (v/v) $H_2S$, but more typically it is in the range of 40-3,000 ppm (v/v) and even more typically in the range of 300-2,500 ppm (v/v).

Before feeding a stream of the biogas to a compressor, it may optionally be passed through an inlet filter. The compressor compresses the biogas to a typical pressure of 50 to 500 psig, more typically 100-300 psig and often 150-250 psig. The compressor is cooled with cooling oil which is cooled at a heat exchanger that is either integrated with the compressor or separate from the compressor.

The compressed biogas feed stream (i.e., the PTSA feed gas stream) is fed to a PTSA unit that includes two or more (typically 2-4) adsorbent beds containing adsorbent. Each bed is selective for water, VOCs, and $H_2S$ over $CO_2$ and for $H_2S$ over methane. Each bed is optionally also selective for siloxanes over methane. The selectivity for $H_2S$ over $CO_2$ is not an arbitrary feature. While $H_2S$ and $CO_2$ adsorb strongly on most adsorbents used in the field of adsorbent-based gas separations, for gases containing relatively high levels of $CO_2$ in comparison to $H_2S$ (such as biogas), the $H_2S$ winds up being adsorbed in relatively lower amounts in comparison to $CO_2$. For this reason, it is important that the adsorbent beds be selective for $H_2S$ over $CO_2$. Otherwise, much of the adsorption sites needed for adsorption of $H_2S$ would tend to be blocked by adsorbed $CO_2$. The aforementioned selectivity properties may be accomplished by using a single adsorbent meeting each of these selectivities or by using multiple adsorbents in a layered bed. While it is desired to remove $H_2O$ and VOCs at the same time as removing $H_2S$, the adsorbent used for $H_2S$ removal may not be the most advantageous for removal of $H_2O$ or VOCs. Thus, multiple adsorbents can be used in the PTSA beds that are targeted to the composition of the PTSA feed gas stream being treated. Such adsorbents are normally installed in layers and such composite beds are commonly used and well know to one skilled in the art. The bed may be layered with an adsorbent particularly suitable for sorbing water and VOCs at the inlet of the bed and a different adsorbent (downstream of the inlet) particularly suitable for sorbing $H_2S$. Further, as with other PTSA systems, the adsorber vessels are insulated and either internal or external insulation can be applied with no change to the invention.

Suitable adsorbents include but are not limited to silica gel such as available from Grace or BASF (under the trade name Sorbead®), SulfaTrap™ available from SulfaTrap, Inc., various molecular sieves including 4A, 5A and 13X versions, natural zeolites, or alumina.

Each of the beds of the PTSA unit is operated in PTSA cycle phases of adsorption, depressurization, thermal regeneration using a regeneration gas stream heated to a temperature above that of the PTSA feed gas stream, cool down using a cool down gas stream, and repressurization with the PTSA feed gas, PTSA product gas and/or retentate gas stream from a first or second gas separation membrane stage (discussed below). During the adsorption phase, the PTSA feed gas stream (typically at a temperature of about 0 to 40° C. and at a pressure of 50 to 500 psig, more typically 150-250 psig) is fed to a regenerated, cooled, and pressurized adsorbent bed that selectively adsorbs water, VOCs, and $H_2S$ from the PTSA feed gas stream to produce a "PTSA product gas" which is further upgraded by the gas separation membranes.

Following the adsorption phase, the adsorption bed is depressurized down to the pressure at which regeneration takes place, for example, at 14-20 psia.

Once a suitable pressure has been reached, the adsorption bed is thermally regenerated by passing a relatively hot regeneration gas stream through the bed and desorbing the water, VOCs, and $H_2S$ that was adsorbed from the PTSA feed gas stream. A waste gas comprised of the gas of the thermal regeneration gas stream plus the desorbed water, VOCs, and $H_2S$ is withdrawn from the PTSA unit.

While the regeneration temperature may be selected dependent upon the impurities adsorbed upon the adsorbent from the PTSA feed gas stream and also upon the selected adsorbent applied, typically the regeneration temperature ranges from 250-600° F.

Following regeneration, the adsorbent bed is cooled down to a suitable temperature to prepare it for the adsorption phase of the next PTSA cycle. Once the suitable temperate is reached, the adsorbent bed is repressurized with PTSA feed gas in order to reach the pressure maintained during the adsorption phase. Following the cool down and repressurization, the PTSA cycle may be repeated.

A water, VOCs, and $H_2S$-depleted "PTSA product gas" stream is withdrawn from the PTSA unit and fed to a first of two gas separation membrane stages each of which includes one or more gas separation membranes. Each of the gas separation membranes of the two stages is selective for permeating $CO_2$ and $O_2$ over methane. Thus, the first gas separation membrane separates the PTSA product gas stream into a permeate gas stream that is enriched in $CO_2$ and $O_2$ over methane (in comparison to the PTSA product gas) and a retentate gas stream that is enriched in methane over $CO_2$ and $O_2$ (in comparison to the PTSA product gas). While the selective layer of the membranes of the first gas separation membrane stage may include any membrane known in the field of gas separation membranes to be selective for $CO_2$ over methane, typically, the selective layer is made of a polyimide.

The first stage retentate gas stream is fed to the second gas separation membrane stage. The second gas separation membrane stage separates the first stage retentate gas stream into a permeate gas stream that is enriched in $CO_2$ and $O_2$ over methane (in comparison to the first stage retentate gas stream) and a retentate gas stream that is enriched in methane over $CO_2$ and $O_2$ (in comparison to the first stage retentate gas stream). The second stage retentate gas stream is withdrawn as the product gas meeting natural gas specifications as described above. The selective layer of the membranes may be the same or different as that of the first gas separation membrane stage and may include any membrane known in the field of gas separation membranes to be selective for $CO_2$ over methane. Typically, the selective layer is made of a polyimide.

A stream of the waste gas withdrawn from the PTSA unit may be vented or sent to a treatment unit for destruction of the VOCs and $H_2S$. Suitable treatment units include burners (which may be supplemented with natural gas for flame stability) especially porous burners. Typically, however, the impurity-laden regeneration gas is treated in a thermal oxidizing (TOX) unit. The heat necessary for desorption of the impurities may be added to the regeneration gas stream by an external heater, and may also use some or all of recovered heat from hot gas or hot oil from the compressor or heat recovery from a thermal oxidizer or other source of waste heat.

While any gas may be used for thermal regeneration of the adsorbent beds, in one aspect of the invention, all or some of the first stage permeate gas stream is used as the thermal regeneration gas. Because some amounts of the methane contained in the PTSA product gas stream will necessarily permeate across the membranes of the first gas separation membrane stage, the first stage permeate gas stream will not only include $CO_2$ but also methane. Typically, the first stage permeate gas stream contains 5-13% (v/v) methane. Because the waste gas will include the methane from the first stage permeate gas stream, thermal oxidization or burning of the VOCs is enhanced by the presence of the methane. Additionally, in the event that the effluent from the hybrid system of the invention is subject to regulatory control over the amount of methane emissions, those amounts of methane not recovered in the product natural gas stream will be burned or oxidized in the treatment unit. Finally, through use of the first stage permeate gas stream as the regeneration gas stream, there is no need to provide another source of gas that is suitably dry and impurity-free enough to allow satisfactory amounts of water, VOCs, and $H_2S$ to be desorbed from the adsorbent beds during thermal regeneration.

While any gas may be used to cool down regenerated adsorbent beds during the cool down phase of the PTSA cycle, in another aspect of the invention, all or some of the second stage permeate gas stream is used as the cool down gas stream. The second stage permeate gas stream withdrawn from the adsorbent bed undergoing cool down (as a recycle stream) is fed to the suction inlet of the main compressor where it is compressed and combined with the raw biogas feed stream to form the PTSA feed gas stream. After the second stage permeate gas is used as the cool down gas stream, it may be fed directly to the suction inlet of the main compressor, or alternatively, it instead may be compressed in a secondary compressor. While this alternative routing of the second stage permeate gas stream/recycle stream requires a second compressor, these gases are largely free of impurities so they may be routed directly to the first gas separation membrane stage after compression. This avoids an increase in the flow rate of the PTSA feed gas stream that must be treated by the PTSA unit. As a result, the size and cost of the PTSA unit may be decreased in comparison to the general scheme where the recycle stream is compressed and combined with the raw biogas feed stream at the main compressor.

When the first stage permeate is used as the regeneration gas stream and the second stage permeate is used as the cool down gas stream, various PTSA cycles may be created depending upon the number of beds in the PTSA unit.

A three-bed PTSA unit maximizes the uses of the first and second stage permeate gas streams as the regeneration and cool down gas streams. For a three-bed PTSA unit, a typical cycle is described in Table I below.

TABLE I typical PTSA cycle for three beds

| | | Phase # | | |
|---|---|---|---|---|
| | | 1 | 2 | 3 |
| Bed # | 1 | adsorption | depressurization then regeneration | cool down then repressurization |
| | 2 | cool down then repressurization | adsorption | depressurization then regeneration |
| | 3 | depressurization then regeneration | cool down then repressurization | adsorption |

For feeds of biogas where excess regeneration gas is available, a more simple two bed cycle can be applied. An example of when excess regeneration gas is available is when the feed gas contains relatively low levels of impurities, such as low levels of H2S such that the amount of adsorbent to be heated is reduced as compared to a feed with higher levels of impurities. A typical cycle for a two-bed PTSA unit is described in Table II below.

TABLE II typical PTSA cycle for two beds

| | | Phase # | | | |
|---|---|---|---|---|---|
| | | 1 | 2 | 3 | 4 |
| Bed # | 1 | adsorption | adsorption | depressurization then regeneration | cool down then repressurization |
| | 2 | depressurization then regeneration | cool down then repressurization | adsorption | adsorption |

While the three bed cycle is a basic approach the technology is not limited by the cycle used. For example where upflow adsorption is used, the velocity of the feed gas can be limited by the fluidization velocity and using two vessels simultaneously for adsorption allows a more optimal process. A typical cycle for a four-bed PTSA unit is described in Table III below.

TABLE III typical PTSA cycle for four beds

| | | Phase # | | | |
|---|---|---|---|---|---|
| | | 1 | 2 | 3 | 4 |
| Bed # | 1 | adsorption | adsorption | depressurization then regeneration | cool down then repressurization |
| | 2 | cool down then repressurization | adsorption | adsorption | depressurization then regeneration |
| | 3 | depressurization then regeneration | cool down then repressurization | adsorption | adsorption |
| | 4 | adsorption | depressurization then regeneration | cool down then repressurization | adsorption |

I will now proceed to describe some process configurations for carrying out the invention described above. One of ordinary skill in the art will recognize that any of the aspects (including alternative embodiments or variations) of the invention described above may be combined with any of the specific process configurations described below.

As best shown in FIGS. 1 and 1', a stream of raw biogas 1 is fed to a main compressor 3. A PTSA feed gas stream 5 is received from the compressor 3 and fed to one or more adsorbent beds the PTSA unit 7 that are undergoing the repressurization phase and one or more adsorbent beds that are undergoing the adsorption phase. The adsorbent beds of the PTSA unit selectively adsorb, from the pressurized gas of the PTSA feed gas stream 5, $H_2S$, water, and VOCs (and optionally siloxanes) over methane and $H_2S$ over $CO_2$.

A PTSA product gas 9 deficient in $H_2S$, water, and VOCs (and optionally siloxanes) and enriched in $CH_4$ and $CO_2$ in comparison to the PTSA feed gas stream 5 is withdrawn from one or more beds of the PTSA unit 7 undergoing adsorption and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15.

The first stage retentate gas stream 15 is fed to the second gas separation membrane stage 17. The second gas separation membrane stage, including one or more gas separation membranes selective for $CO_2$ over methane separate the first stage retentate stream 15 into a second stage permeate stream 19 and a second stage retentate stream 21. The second stage retentate stream 21 is the product gas that is suitable for on-site use in generators or meets typical pipeline specifications for sale (as described above).

A waste stream 23 includes depressurization gas withdrawn from one or more of the beds the PTSA unit 7 that are undergoing depressurization is fed to a treatment unit 25 where it is burned or thermally oxidized to yield a vent gas 27. After the one or more beds undergoing depressurization are suitably depressurized, instead of bypassing the PTSA unit 7, the first stage permeate gas stream 13 is heated at a heater 29 and fed as a regeneration gas stream 31 to the one or more depressurized adsorbent beds of the PTSA unit 7 that are undergoing regeneration. Thus, the waste stream 23 now includes the gas of the regeneration stream 31 plus impurities desorbed from the one or more beds being regenerated and is fed to the treatment unit 25 for burning or thermal oxidization to yield the vent gas 27.

The second stage permeate gas stream 19 is fed to one or more beds of the PTSA unit 7 undergoing cool down and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the one or more beds undergoing cool down reach a suitable temperature, the second stage permeate gas stream 19 is instead fed to the suction inlet of the main compressor 3 where it combined and compressed with the raw biogas stream 1 to produce the PTSA feed gas stream 5. Alternatively and as shown in FIG. 1', instead of feeding the recycle stream 35 to the suction inlet of the main compressor 3, it is compressed at a secondary compressor 37 and fed to the first gas separation membrane stage 11. Optionally, stream 35 is cooled before being fed to the suction inlet of the main or secondary compressor 3, 37.

Regardless of whether the recycle stream 35 is fed to the main compressor 3 or secondary compressor 37, simultaneous with this, the PTSA feed gas 5 is also fed to the one or more beds that have been cooled down in order to repressurize them in anticipation of undergoing adsorption in the next phase of the PTSA cycle. Optionally, repressurization is conducted with PTSA product gas and/or the first or second gas separation membrane stage retentate streams 15, 21.

In two particular embodiments and as best shown in FIGS. 1" and 1''', there are three membrane gas separation stages 11, 17, 18 each of which includes one or more gas separation membranes selective for $CO_2$ over methane. The difference between the embodiments of FIGS. 1 and 1' and the embodiments of FIGS. 1" and 1''' is as follows. Instead of heating the first stage permeate gas stream 13 and using it as a regeneration gas stream for the one or more depressurized adsorbent beds of the PTSA unit 7 that are undergoing regeneration, additional amounts of methane are recovered from the first stage permeate gas stream 13 at the third gas separation membrane stage 18. The first permeate gas stream 13 is first compressed at a tertiary compressor 14 to a pressure at or above that of the PTSA product gas stream 9 and subsequently fed to the third gas separation membrane stage 18 where it is separated into a third permeate stream 20 and a third retentate stream 22. The third retentate stream 22 is fed, along with the PTSA product gas stream 9, to the first gas separation membrane stage 11 where some of the methane recovered at the third stage 18 may be recovered in the first retentate gas 15. In this embodiment, the third permeate stream 20 performs the same functions of the first permeate stream 13 in the embodiment of FIGS. 1 and 1'. Thus, the regeneration stream 31 is fed to the one or more depressurized adsorbent beds of the PTSA unit 7 that are undergoing regeneration so as to desorb impurities from the one or more beds being regenerated. As with the embodiments of FIG. 1 and 1' the regeneration stream 31, now containing desorbed impurities, is fed to the treatment unit 25 for burning or thermal oxidization to yield the vent gas 27. Finally, the embodiment of FIG. 1''' differs from that of FIG. 1'' in that, instead of feeding the recycle stream 35 to the suction inlet of the main compressor 3, in the embodiment of FIG. 1''' it is compressed at a secondary compressor 37 and fed to the first gas separation membrane stage 11. Optionally, stream 35 is cooled before being fed to the suction inlet of the main or secondary compressor 3, 37.

In two other particulars embodiments and as best shown in FIGS. 2A-2D and 2A'-2D', the PTSA unit 7 includes two adsorbent beds 41, 42 that undergo four phases in the PTSA cycle as shown in Table II above.

Figure 2A:
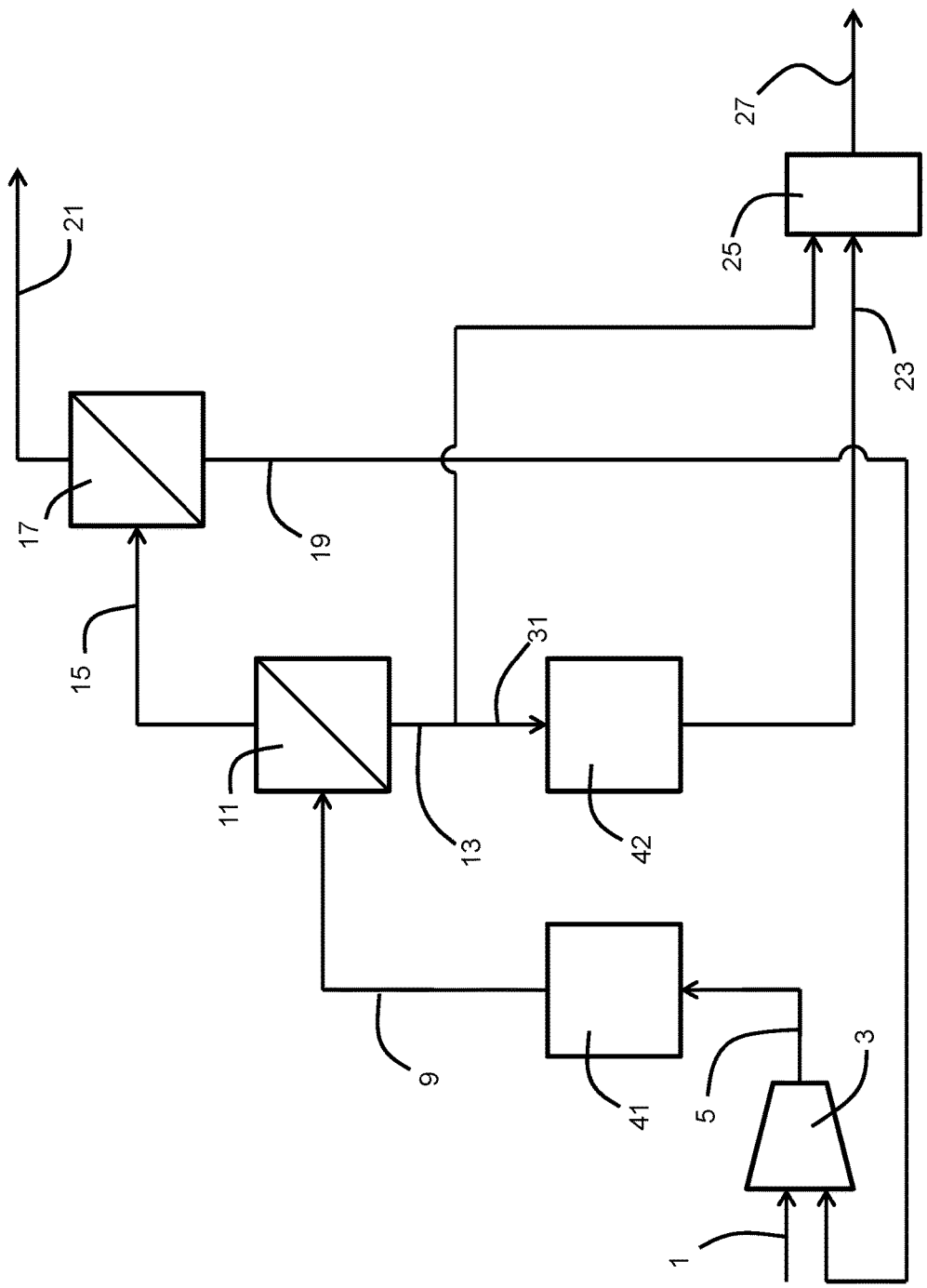
FIG. 2A is a schematic of a first phase of a first two-bed embodiment of the method and system of the invention.

In a first phase of the embodiments of FIGS. 2A-2D and FIGS. 2A'-2D' and as best shown in FIGS. 2A and 2A', the raw biogas stream 1 is fed to and compressed by the main compressor 3. The PTSA feed gas stream 5 is withdrawn from the main compressor 3 and fed to a first adsorbent bed 41 of the PTSA unit 7 (the outlines of which are not illustrated for sake of clarity). The first adsorbent bed 41 undergoes adsorption in the first and second phases where it selectively adsorbs, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the first adsorbent bed 41 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas that is suitable for on-site use in generators or meets typical pipeline specifications for sale (as described above).

A waste stream 23 includes depressurization gas withdrawn from a second adsorption bed 42 of the PTSA unit 7 that is undergoing depressurization. The waste stream 23 is fed to the treatment unit 25 where it is burned or thermally oxidized to yield the vent gas 27. After the second bed 42 is suitably depressurized, instead of being directly fed to the treatment unit 25 and bypassing the PTSA unit 7, the first stage permeate gas stream 13 is heated at the heater 29 and fed as a regeneration gas stream 31 to the second adsorbent bed 42 which now undergoes regeneration. Thus, the waste stream 23 now includes the gas of the regeneration stream 31 plus impurities desorbed from the second adsorbent bed and is fed to the treatment unit 25 for burning or thermal oxidization to yield the vent gas 27.

The second stage permeate gas stream 19 is recycled to the suction inlet of the main compressor 3 where it is combined and compressed with the raw biogas stream 1 to yield the PTSA feed gas stream 5. Alternatively and as illustrated in FIG. 2A', the second stage permeate gas stream 19 may be recycled to a suction inlet of a secondary compressor 37, compressed thereat, and subsequently fed to the first gas separation membrane stage 11.

Figure 2B:
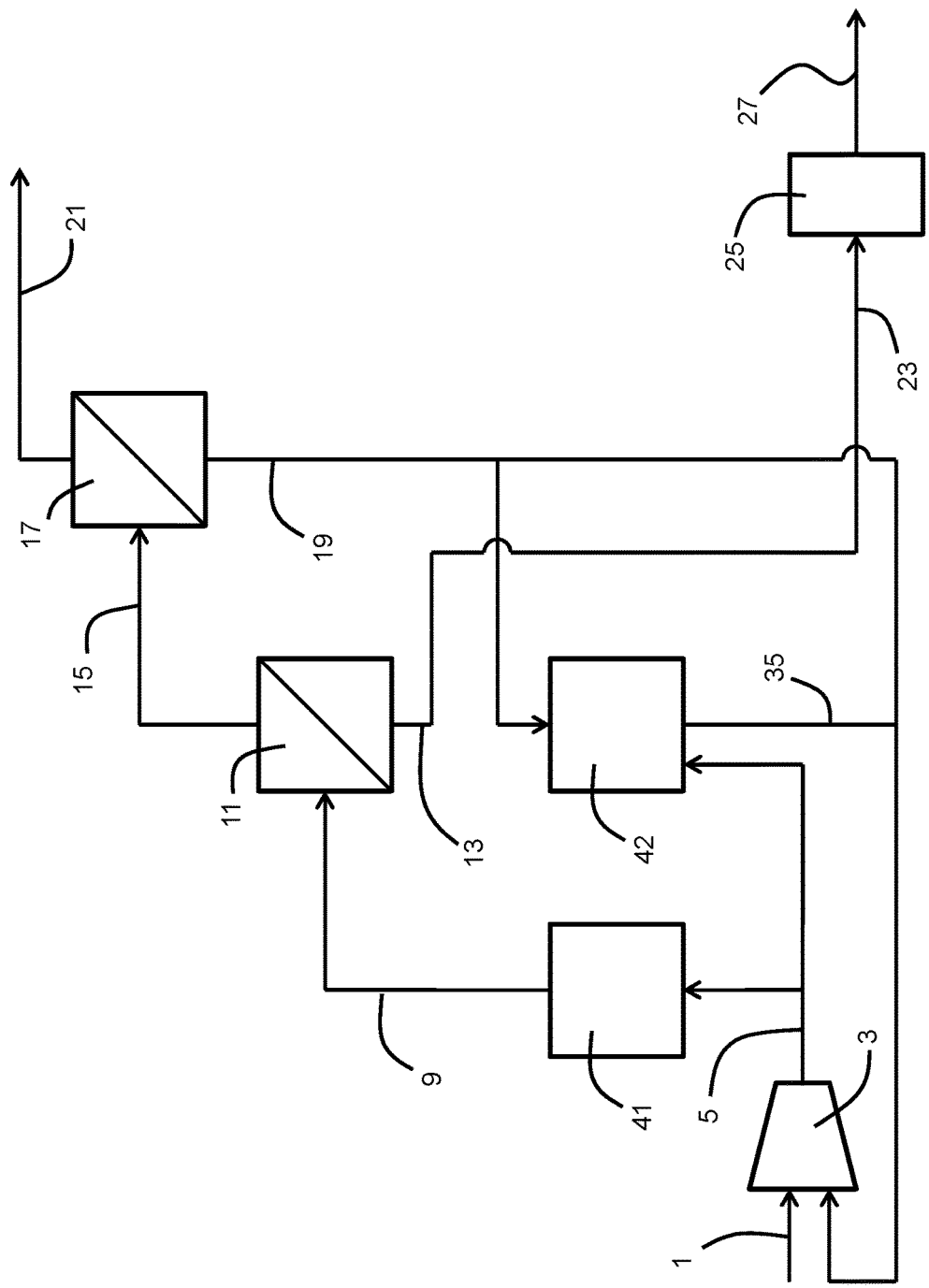
FIG. 2B is a schematic of a second phase of the first two-bed embodiment of the method and system of the invention.
Figure 2A:
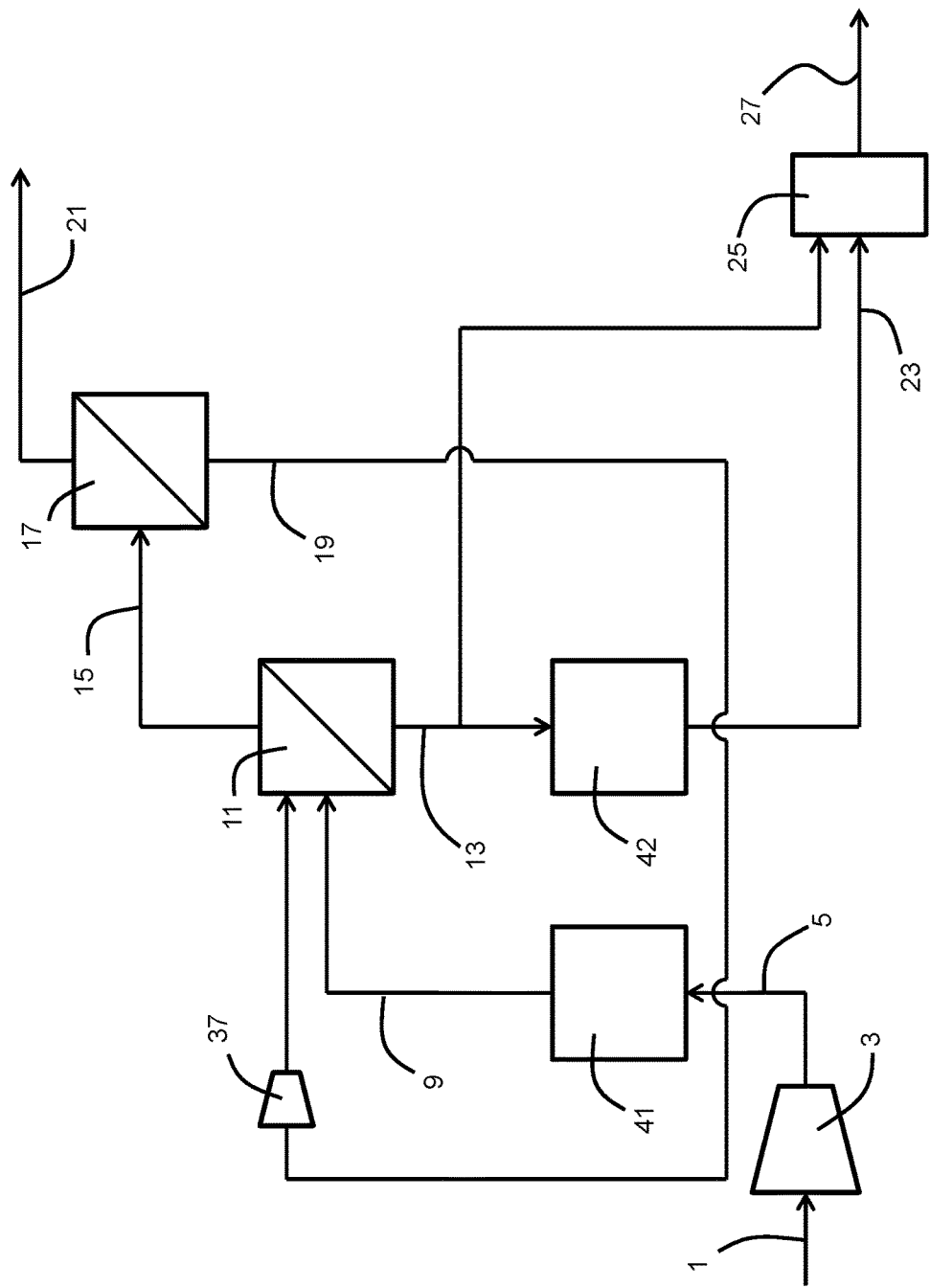
Figure 2B:
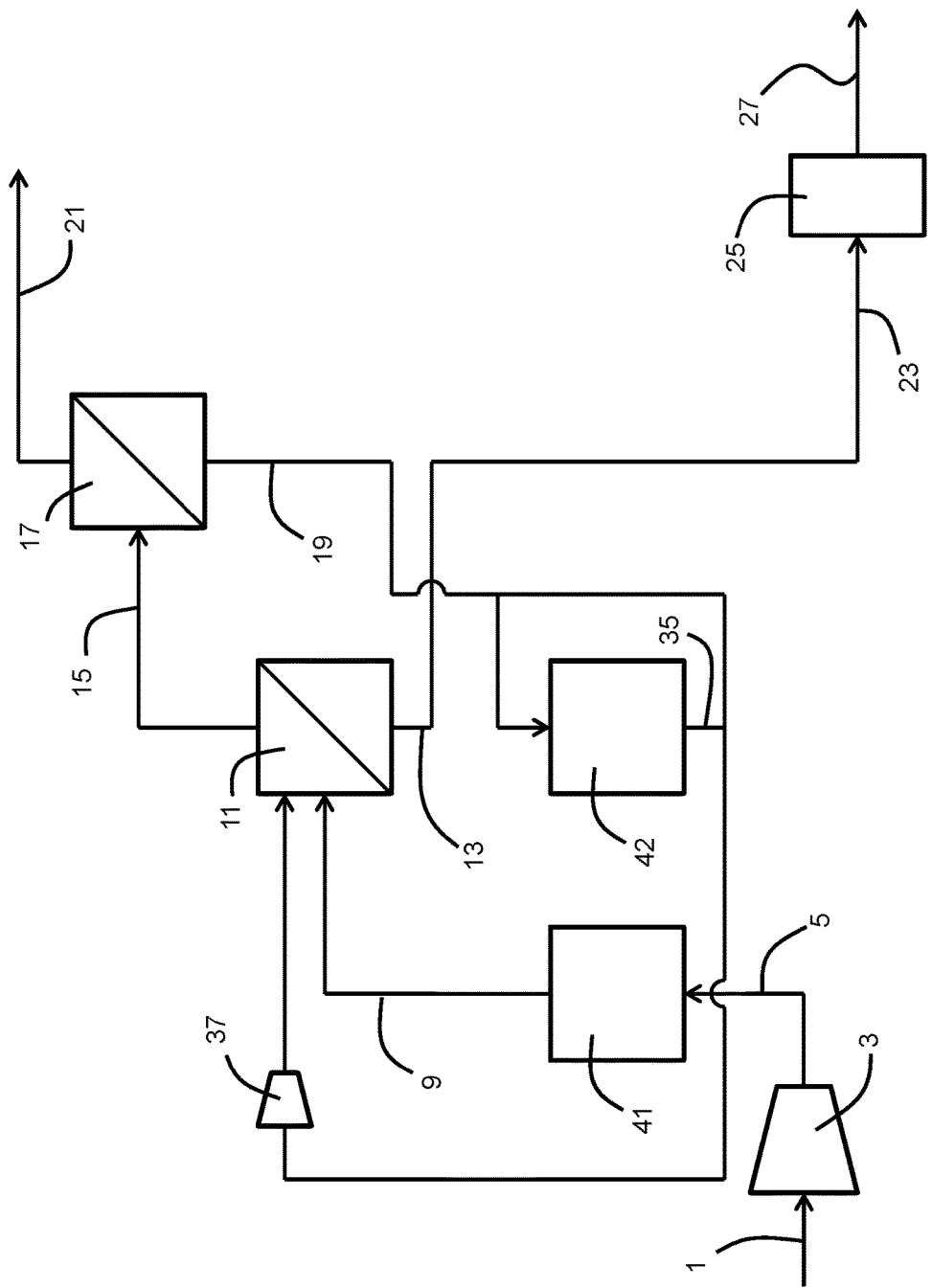

In a second phase of the embodiment of FIGS. 2A-2D and 2A'-2D' and as best shown in FIGS. 2B and 2B', the raw biogas stream 1 is continued to be fed to and compressed by the main compressor 3 and the PTSA feed gas stream 5 continues to be withdrawn from the main compressor 3 and fed to the first adsorbent bed 41 of the PTSA unit 7 as explained above. The first adsorbent bed 41 continues to undergoes adsorption as explained above.

Similarly, the PTSA product gas 9 is withdrawn from the first adsorbent bed 41 and fed to the first gas separation membrane stage 11 where it is separated into a first stage permeate gas stream 13 and a first stage retentate gas stream 15.

The first stage retentate gas stream 15 is fed to the second gas separation membrane stage 17. The second gas separation membrane stage, including one or more gas separation membranes selective for $CO_2$ over methane separate the first stage retentate stream 15 into a second stage permeate stream 19 and a second stage retentate stream 21. The second stage retentate stream 21 is the product gas that is suitable for on-site use in generators or meets typical pipeline specifications for sale (as described above).

Instead of being fed to the second adsorbent bed 42 as a regeneration gas, the first stage permeate gas stream 13 is fed to the treatment unit 25. The first stage retentate gas stream 15 is fed to the second gas separation membrane stage 17 where it is separated into a second stage permeate stream 19 and the second stage retentate stream 21.

The second stage permeate gas stream 19 is fed to the second adsorbent bed 42 (which is now undergoing cool down) and recycled as a recycle stream 35 (containing the gas of the second stage permeate gas plus impurities desorbed from the second adsorbent bed 42) to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the second adsorbent bed 42 reaches a suitable temperature, the second stage permeate gas stream 19 bypasses the second adsorbent bed 42 and is instead fed to the suction inlet of the main compressor 3 where it combined and compressed with the raw biogas stream 1 to produce the PTSA feed gas stream 5. Simultaneous with this, the PTSA feed gas stream 5 is also fed to the second adsorbent bed 42 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 2B', instead of feeding the bypassing second stage permeate gas stream 19 to the suction inlet of the main compressor 3, it is compressed at the suction inlet of the secondary compressor 37, compressed thereat, and subsequently fed to the first gas separation membrane stage 11. Optionally, the recycle stream 35 may be cooled before being fed to the suction inlet of the secondary compressor 37.

I note that, although streams 19 and 35 are illustrated as being contiguous along a common terminal branch in FIGS. 2B, 2B', 2D, 2D', 3A-3C, 3A'-3C', 4A-4D, and 4A'-4D', the skilled artisan will recognize that the flows of gas may be directed through a common section of piping or different piping terminating at the main compressor 3.

In a third phase of the embodiment of FIGS. 2A-2D and 2A'-2D' and as best shown in FIGS. 2C and 2C', the raw biogas stream 1 is fed to and compressed by the main compressor 3. The PTSA feed gas stream 5 is withdrawn from the main compressor 3 and is now fed to the second adsorbent bed 42 instead of the first adsorbent bed 41. The second adsorbent bed 42 undergoes adsorption in the third and fourth phases where it selectively adsorbs, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the second adsorbent bed 42 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas as described above.

A waste stream 23 includes depressurization gas withdrawn from the first adsorption bed 41 which is now undergoing depressurization. The waste stream 23 is fed to the treatment unit 25 where it is burned or thermally oxidized to yield the vent gas 27. After the first bed 41 is suitably depressurized, instead of being directly fed to the treatment unit 25, the first stage permeate gas stream 13 is heated at the heater 29 and fed as a regeneration gas stream 31 to the first adsorbent bed 41 which is now undergoing regeneration. Thus, the waste stream 23 now includes the gas of the regeneration stream 31 plus impurities desorbed from the first adsorbent bed 41 and is fed to the treatment unit 25 for burning or thermal oxidization to yield the vent gas 27.

The second stage permeate gas stream 19 is recycled to the suction inlet of the main compressor 3 where it is combined and compressed with the raw biogas stream 1 to yield the PTSA feed gas stream 5. Alternatively and as shown in FIG. 2C', the second stage permeate gas stream 19 is fed to the suction inlet of the secondary compressor 37, compressed thereat, and subsequently fed to the first gas separation membrane stage 11. Optionally, the recycle stream 35 may be cooled before being fed to the suction inlet of the main compressor 3.

Figure 2D:
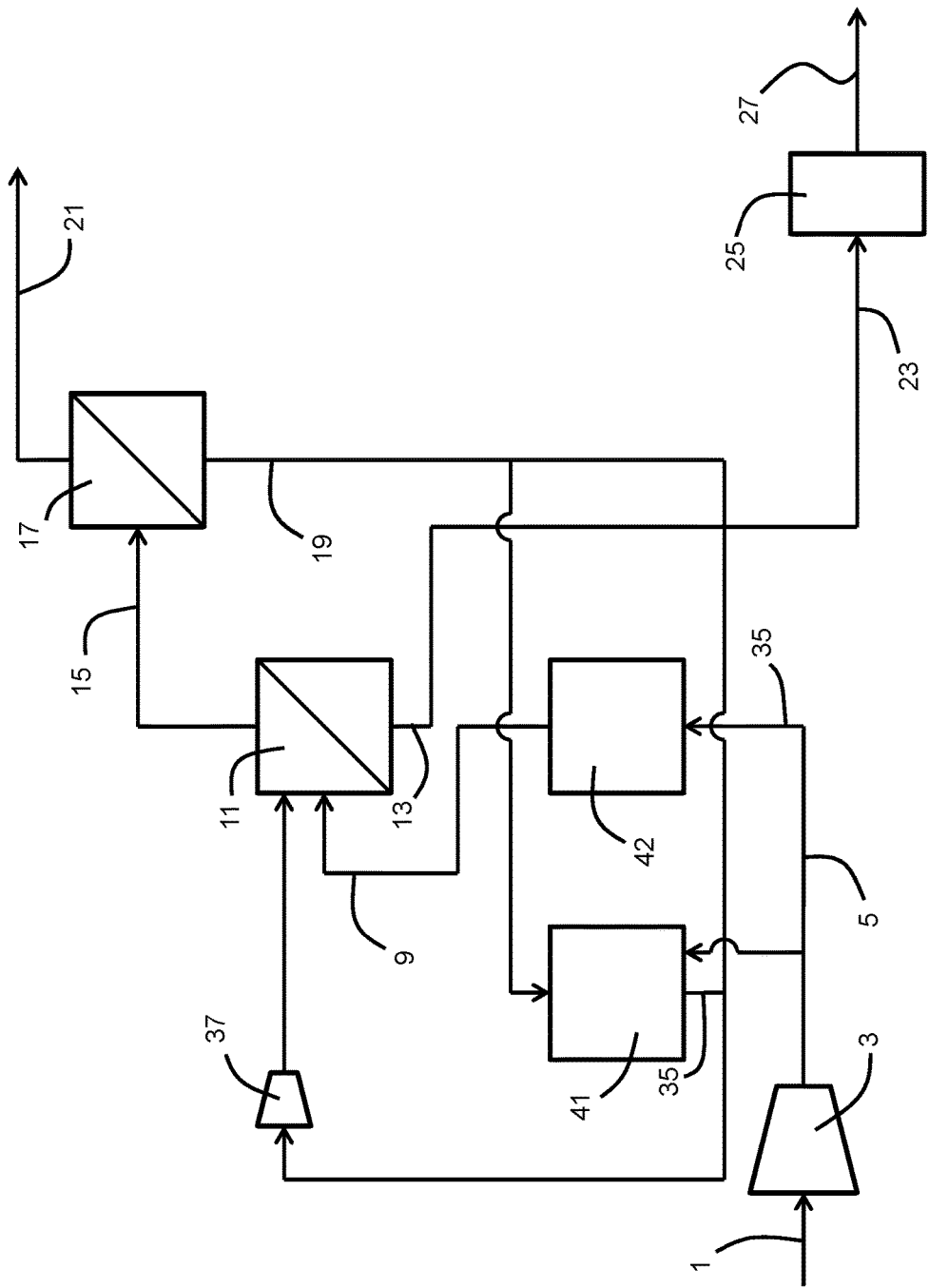
FIG. 2D is a schematic of a fourth phase of the first two-bed embodiment of the method and system of the invention.
Figure 2A:
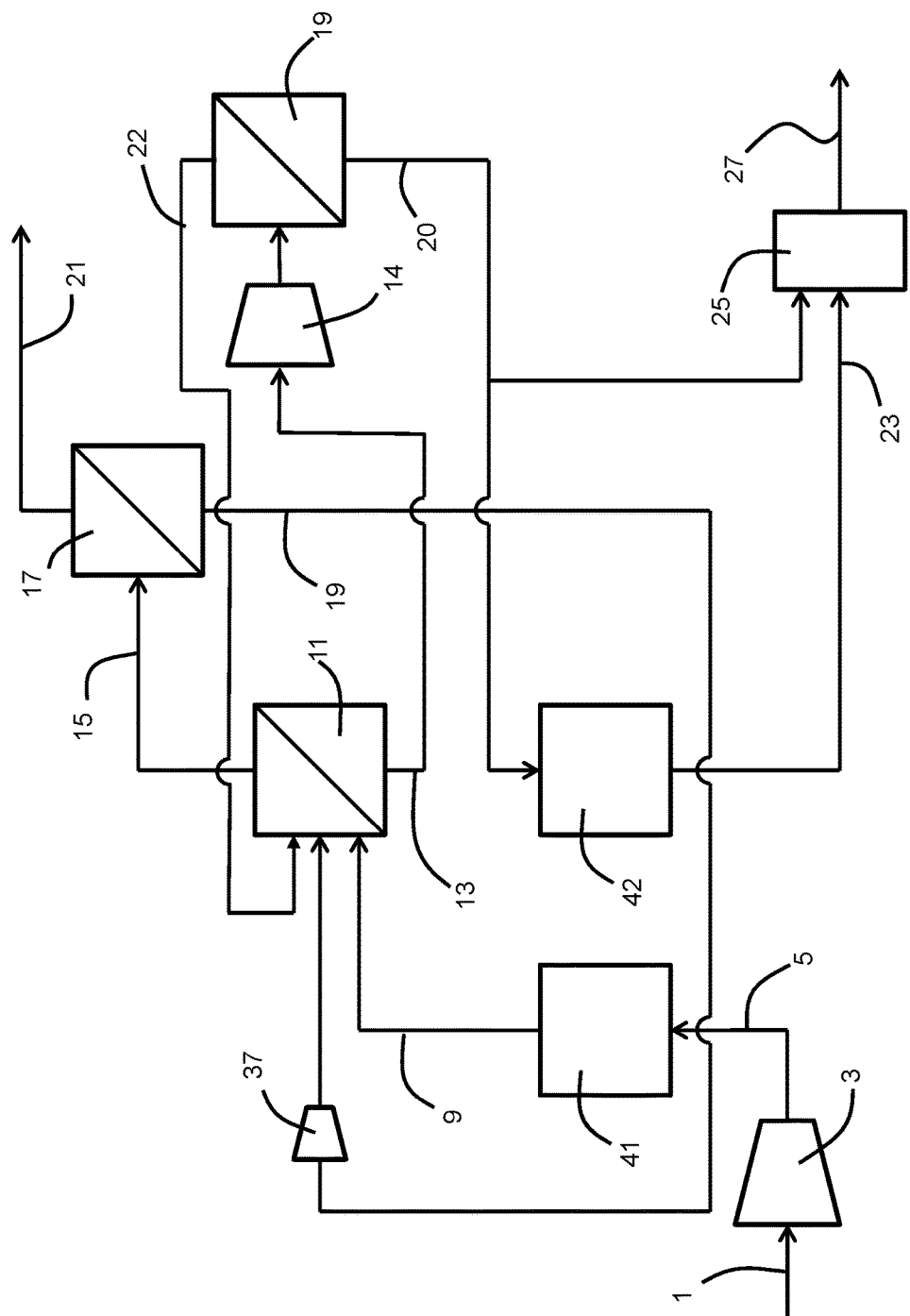
Figure 2B:
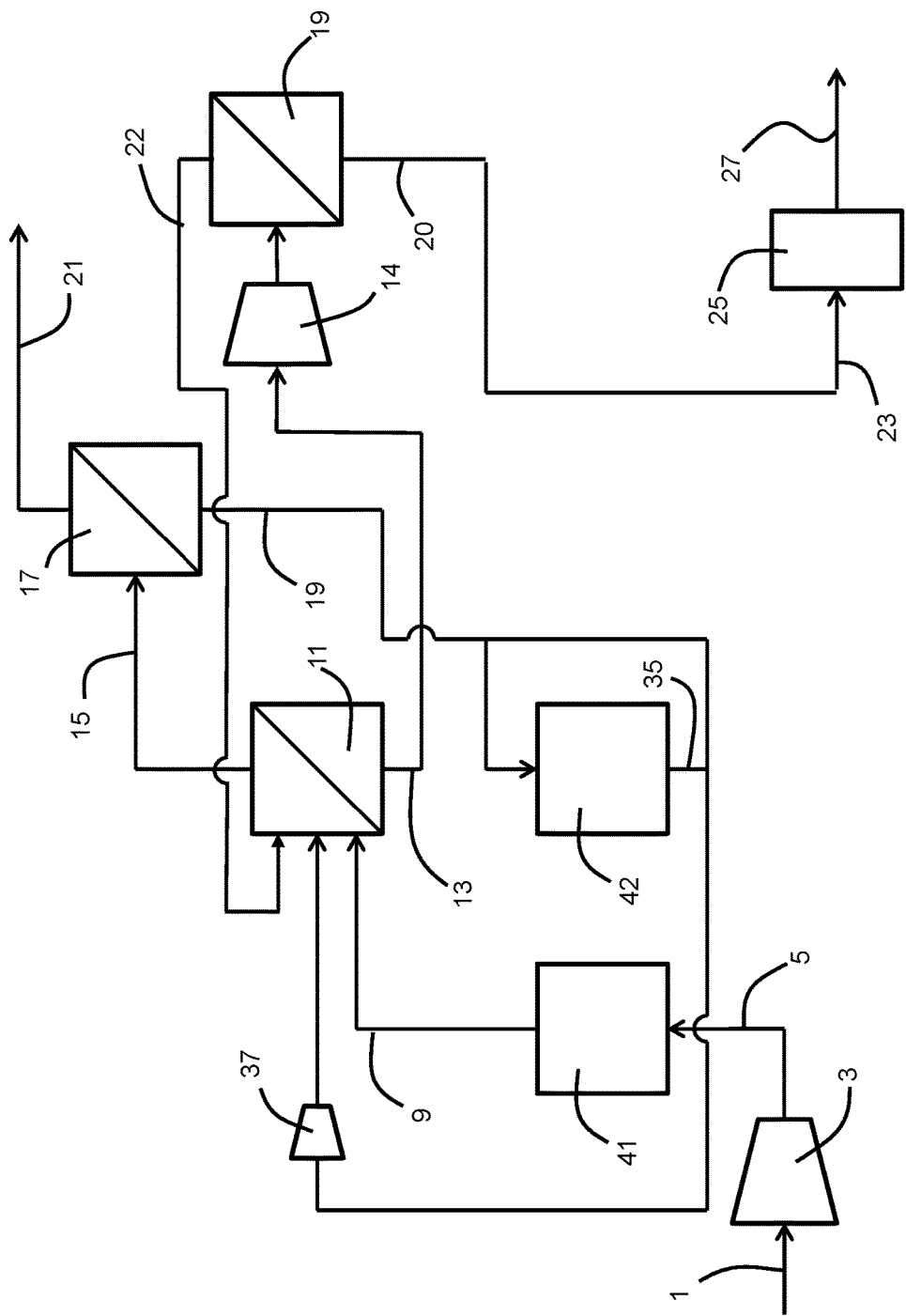
Figure 2D:
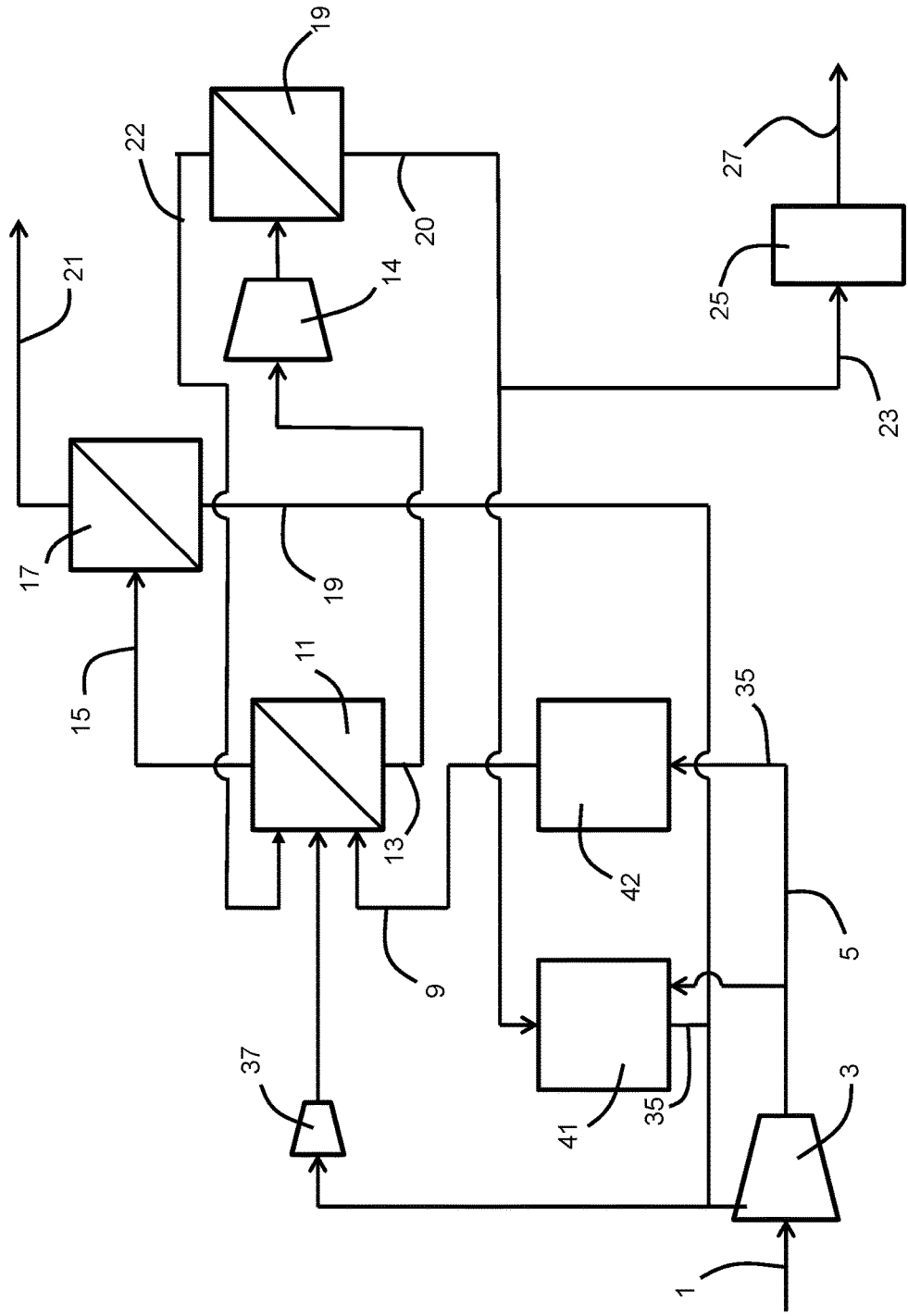

In a fourth phase of the embodiment of FIGS. 2A-2D and 2A'-2D' and as best shown in FIGS. 2D and 2D', the raw biogas stream 1 is continued to be fed to and compressed by the main compressor 3 and the PTSA feed gas stream 5 continues to be withdrawn from the main compressor 3 and fed to the second adsorbent bed 42 as explained above. The first adsorbent bed 42 continues to undergoes adsorption as explained above.

Similarly, the PTSA product gas 9 is withdrawn from the second adsorbent bed 42 and fed to the first gas separation membrane stage 11 where it is separated into a first stage permeate gas stream 13 and a first stage retentate gas stream 15.

Instead of being fed to the first adsorbent bed 41 as a regeneration gas, the first stage permeate gas stream 13 is fed to the treatment unit 25. The first stage retentate gas stream 15 is fed to the second gas separation membrane stage 17 where it is separated into a second stage permeate stream 19 and the second stage retentate stream 21.

The second stage permeate gas stream 19 is fed to the first adsorbent bed 41 (which is now undergoing cool down) and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the first adsorbent bed 41 reaches a suitable temperature, the second stage permeate gas stream 19 bypasses the first adsorbent bed 41 and is instead fed to the suction inlet of the main compressor 3 where it combined and compressed with the raw biogas stream 1 to produce the PTSA feed gas stream 5. Simultaneous with this, the PTSA feed gas stream 5 is also fed to the first adsorbent bed 41 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 2D', instead of feeding the bypassing second stage permeate gas stream 19 to the suction inlet of the main compressor 3, it is fed to the suction inlet of the secondary compressor 37, compressed thereat, and fed to the first gas separation membrane stage 11. Optionally, the recycle stream 35 may be cooled before being fed to the suction inlet of the secondary compressor 37.

In two particular other embodiments illustrated in FIGS. 2A"-2D" and 2A'"-2D'", there are three membrane gas separation stages 11, 17, 18 each of which includes one or more gas separation membranes selective for $CO_2$ over methane. The difference between the embodiments of FIGS. 2A-2D/2A'-2D' and the embodiments of 2A"-2D"/2A'"-2D'" is as follows. Instead of heating the first stage permeate gas stream 13 and using it as a regeneration gas stream for one of the adsorbent beds 41, 42 which have undergone depressurization, additional amounts of methane are recovered from the first stage permeate gas stream 13 at the third gas separation membrane stage 18. The first permeate gas stream 13 is first compressed at a tertiary compressor 14 to a pressure at or above that of the PTSA product gas stream 9 and subsequently fed to the third gas separation membrane stage 18 where it is separated into a third permeate stream 20 and a third retentate stream 22. The third retentate stream 22 is fed, along with the PTSA product gas stream 9, to the first gas separation membrane stage 11 where some of the methane recovered at the third stage 18 may be recovered in the first retentate gas 15. In this embodiment, the third permeate stream 20 performs the same functions of the first permeate stream 13 in the embodiment of FIGS. 2A-2D and 2A'-2D'. Thus, the regeneration stream 31 is fed to the adsorbent bed 41, 42 (which has undergone regeneration) so as to desorb impurities from the one or more beds being regenerated. As with the embodiments of FIGS. 2A-2D and 2A'-2D', the regeneration stream 31, now containing desorbed impurities, is fed to the treatment unit 25 for burning or thermal oxidization to yield the vent gas 27. Finally, the embodiment of FIGS. 2A'''-2D''' differs from that of FIGS. 2A''-2D'' in that, instead of feeding the recycle stream 35 to the suction inlet of the main compressor 3, in the embodiment of FIGS. 2A'''-2D''' it is compressed at a secondary compressor 37 and fed to the first gas separation membrane stage 11. Optionally, stream 35 is cooled before being fed to the suction inlet of the main or secondary compressor 3, 37.

Figure 3A:
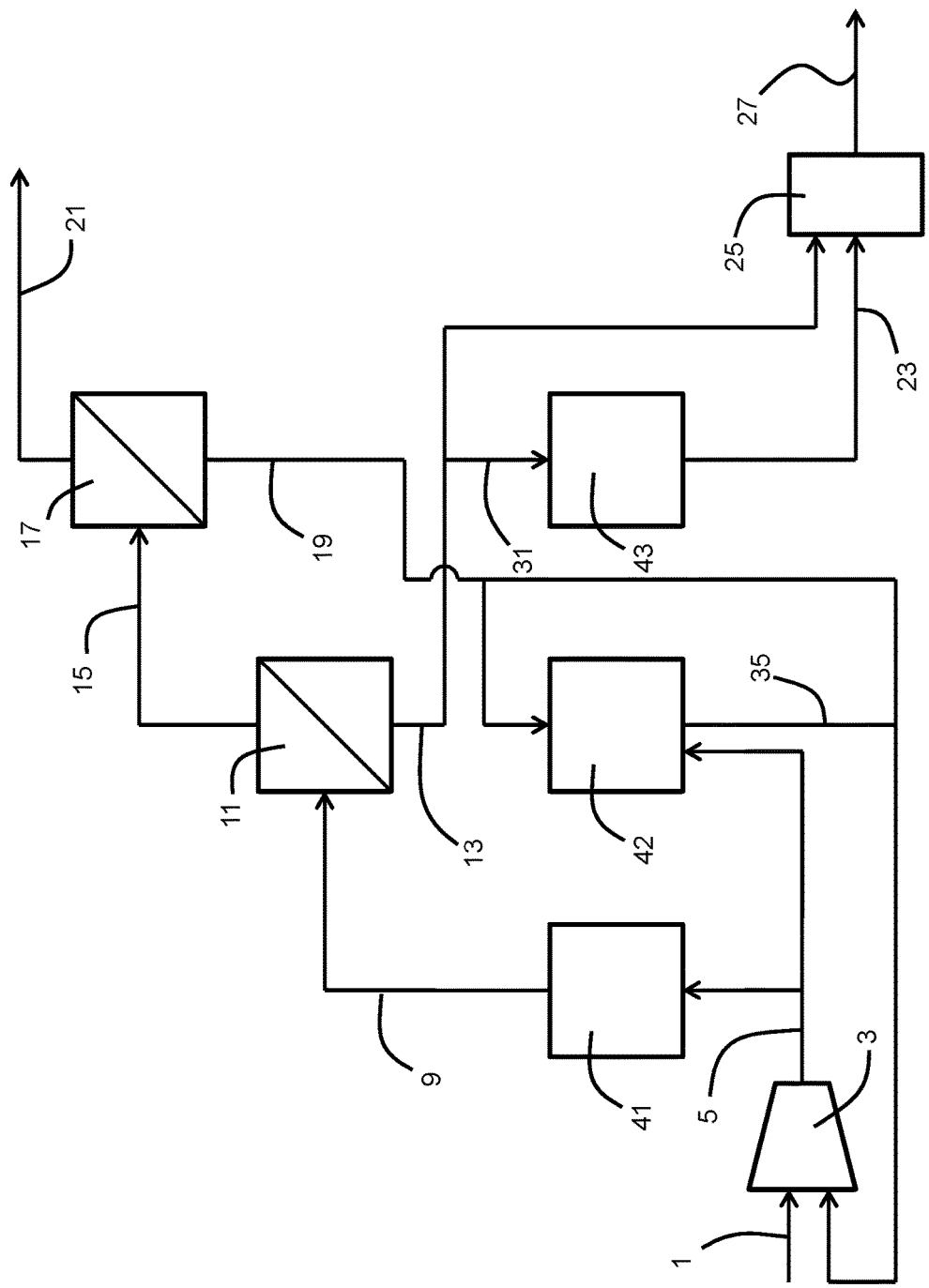
FIG. 3A is a schematic of a first phase of a first three-bed embodiment of the method and system of the invention.
Figure 3C:
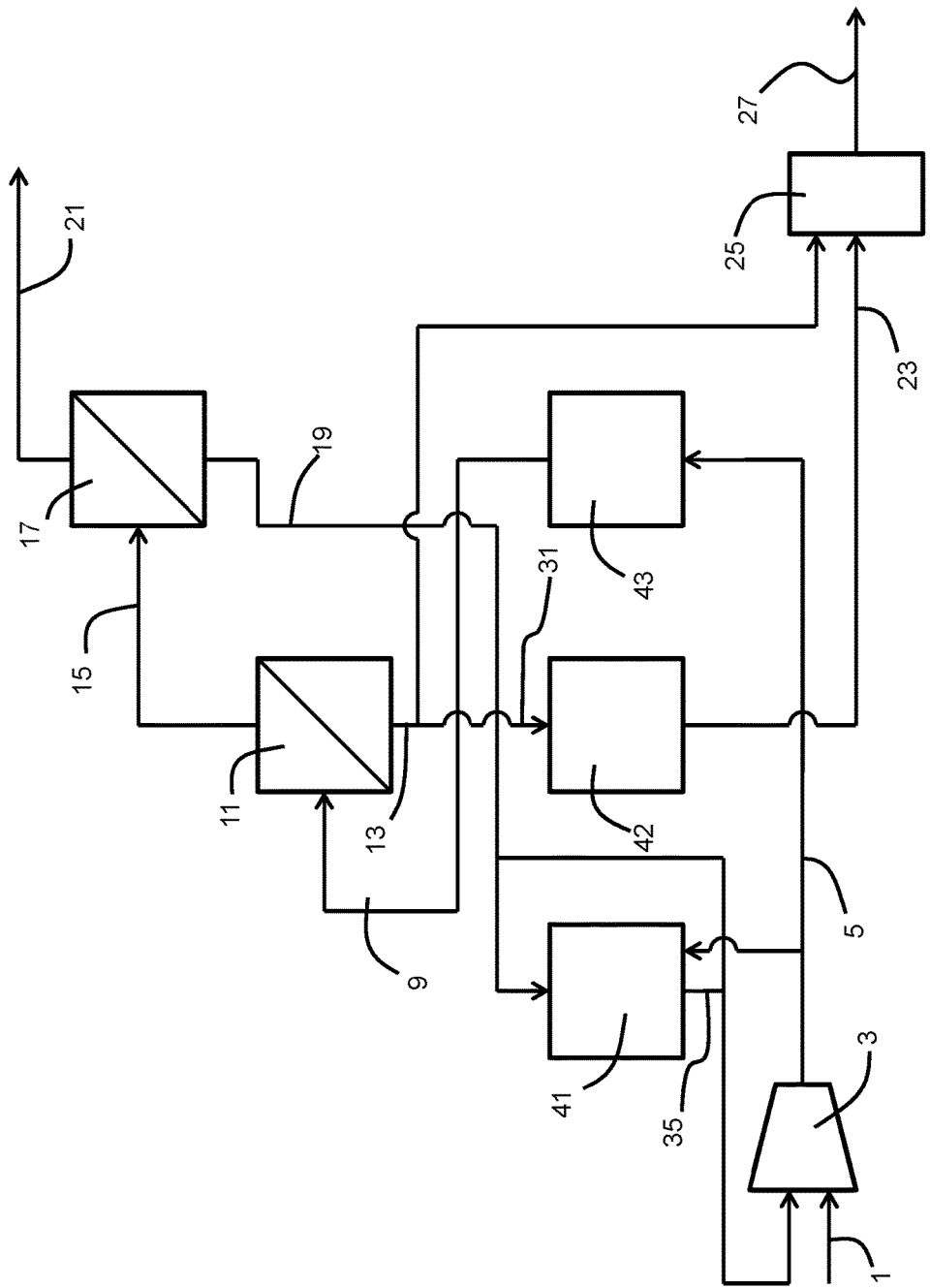
FIG. 3C is a schematic of a third phase of the first three-bed embodiment of the method and system of the invention.
Figure 3A:
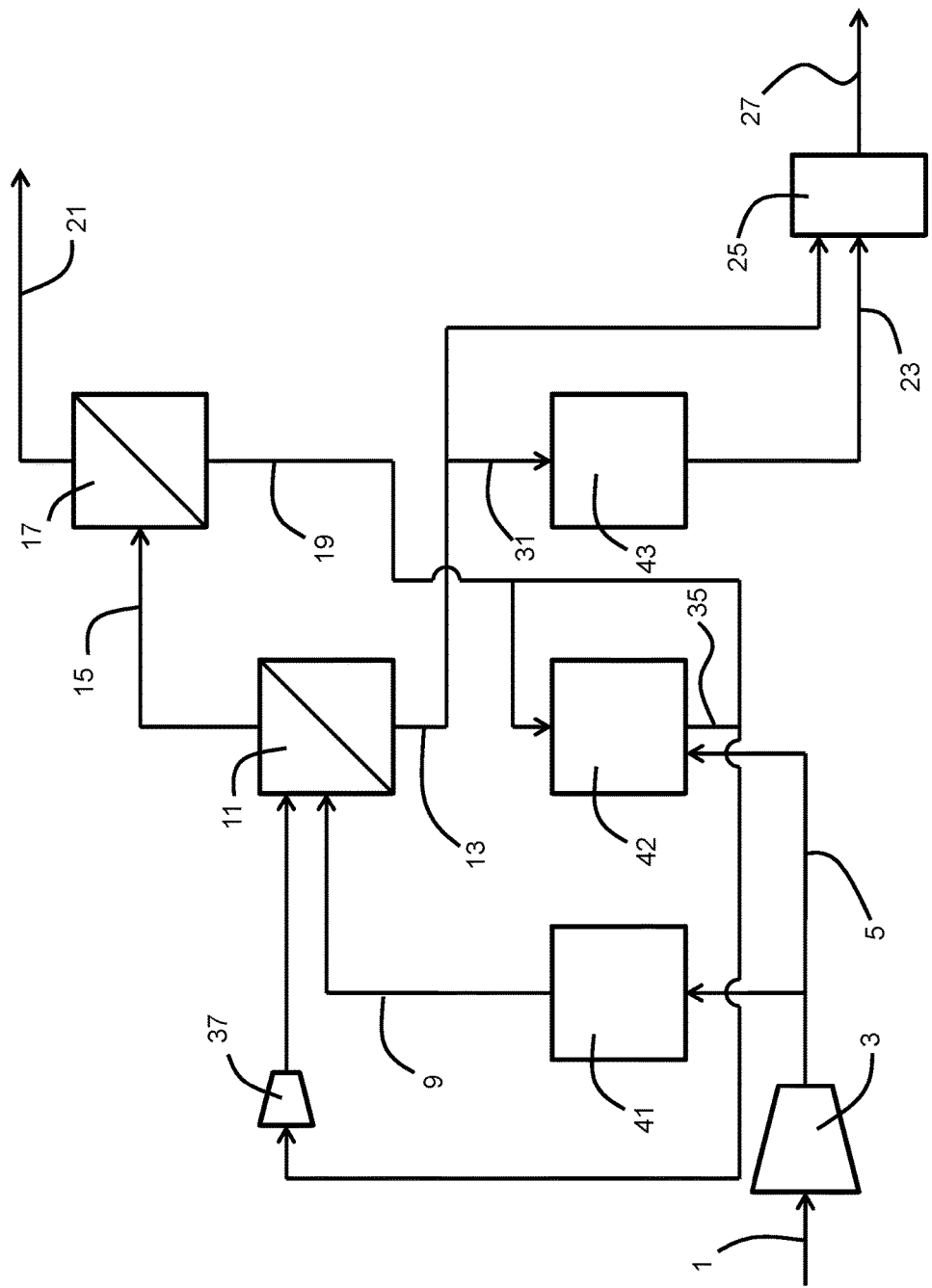
Figure 3B:
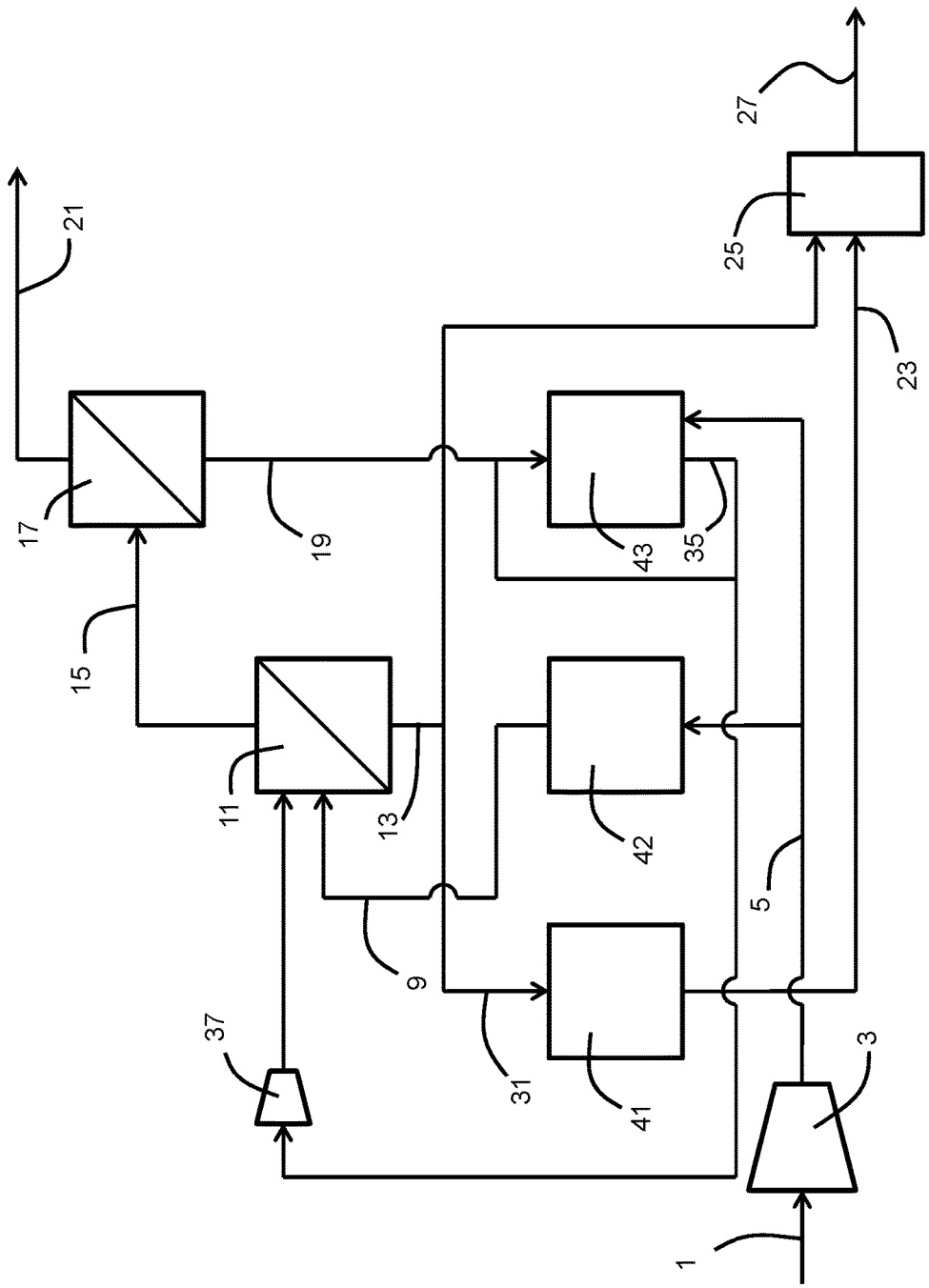
FIG. 3B is a schematic of a second phase of the first three-bed embodiment of the method and system of the invention.
Figure 3C:
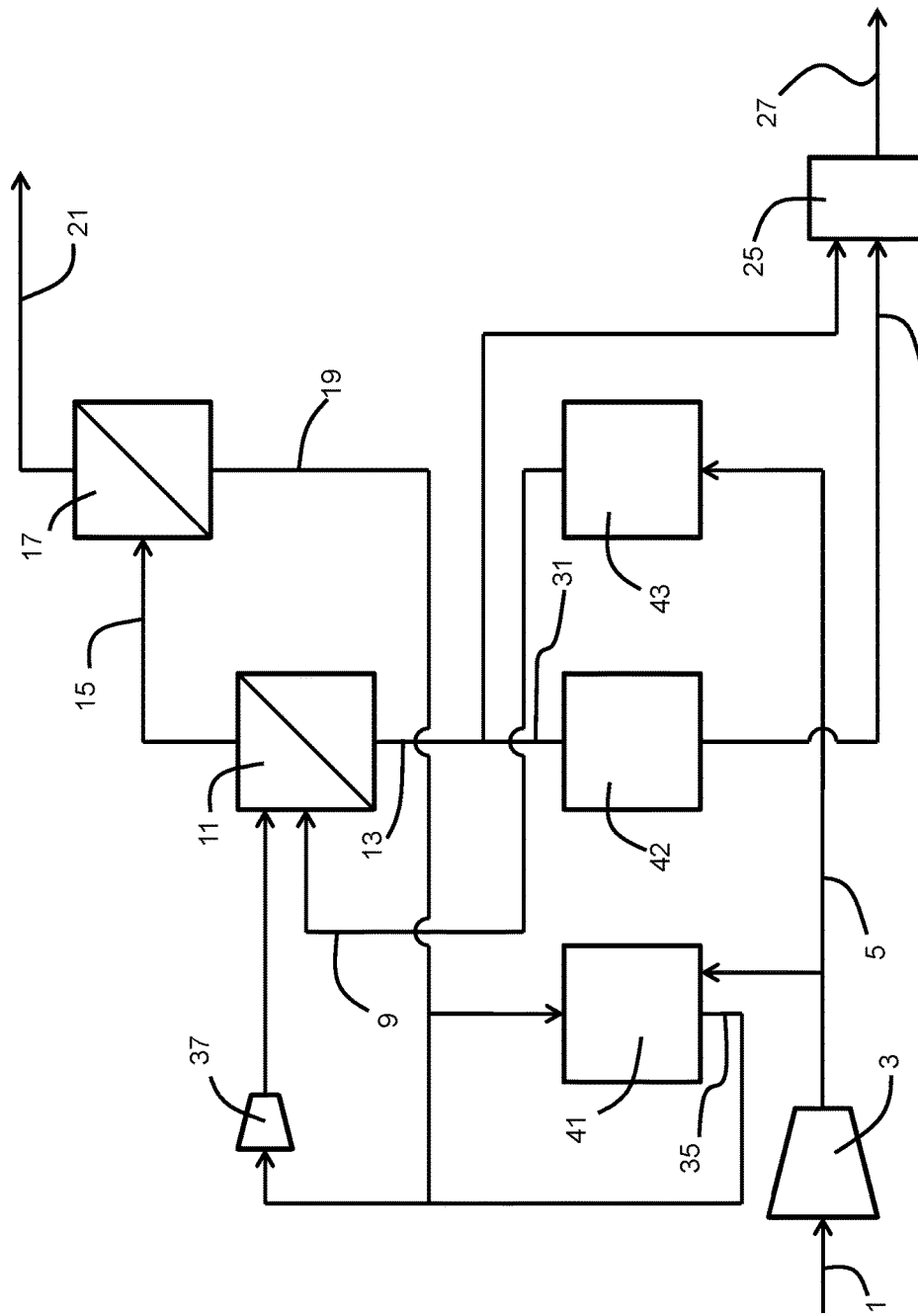
Figure 3A:
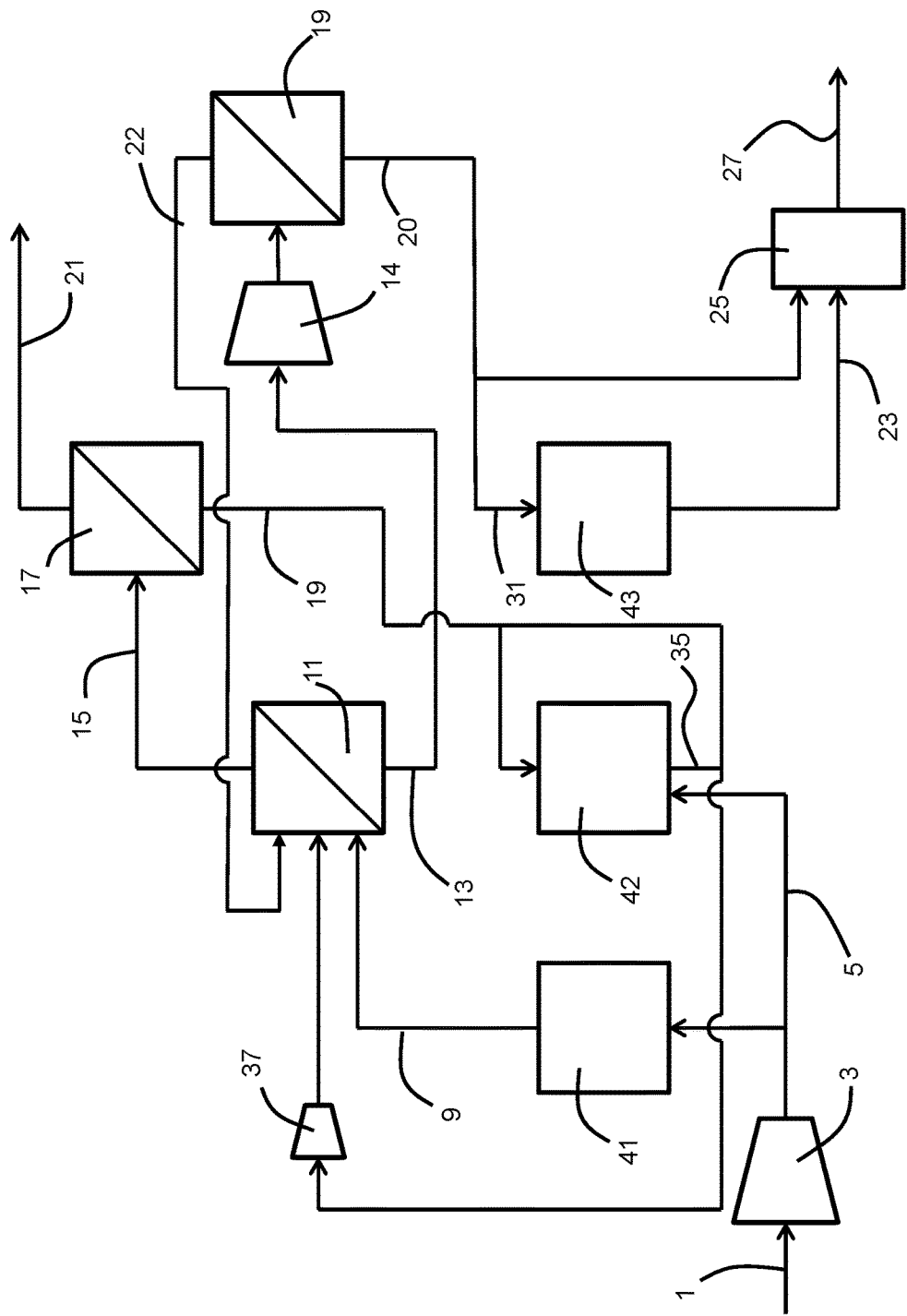
Figure 3B:
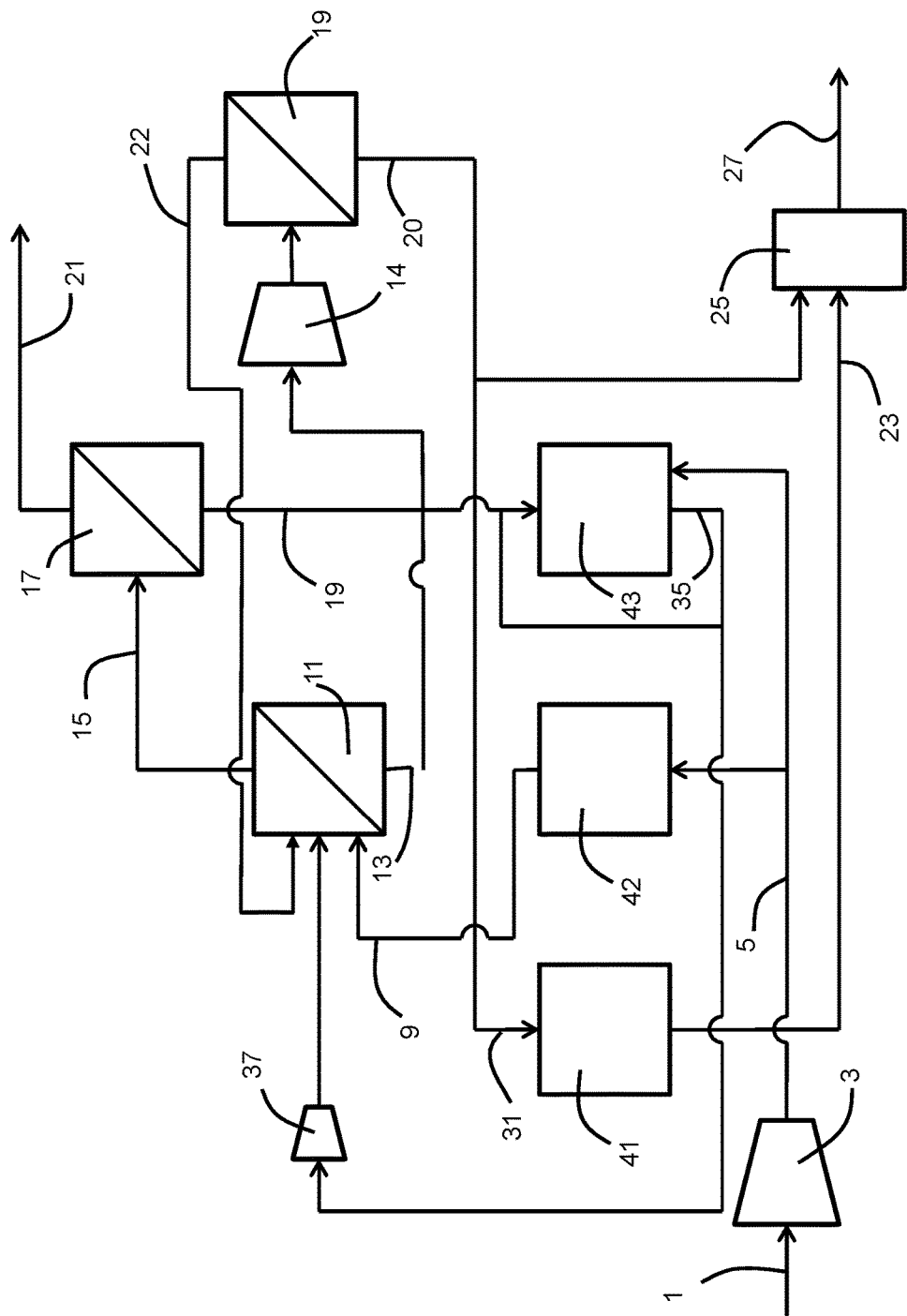
Figure 3C:
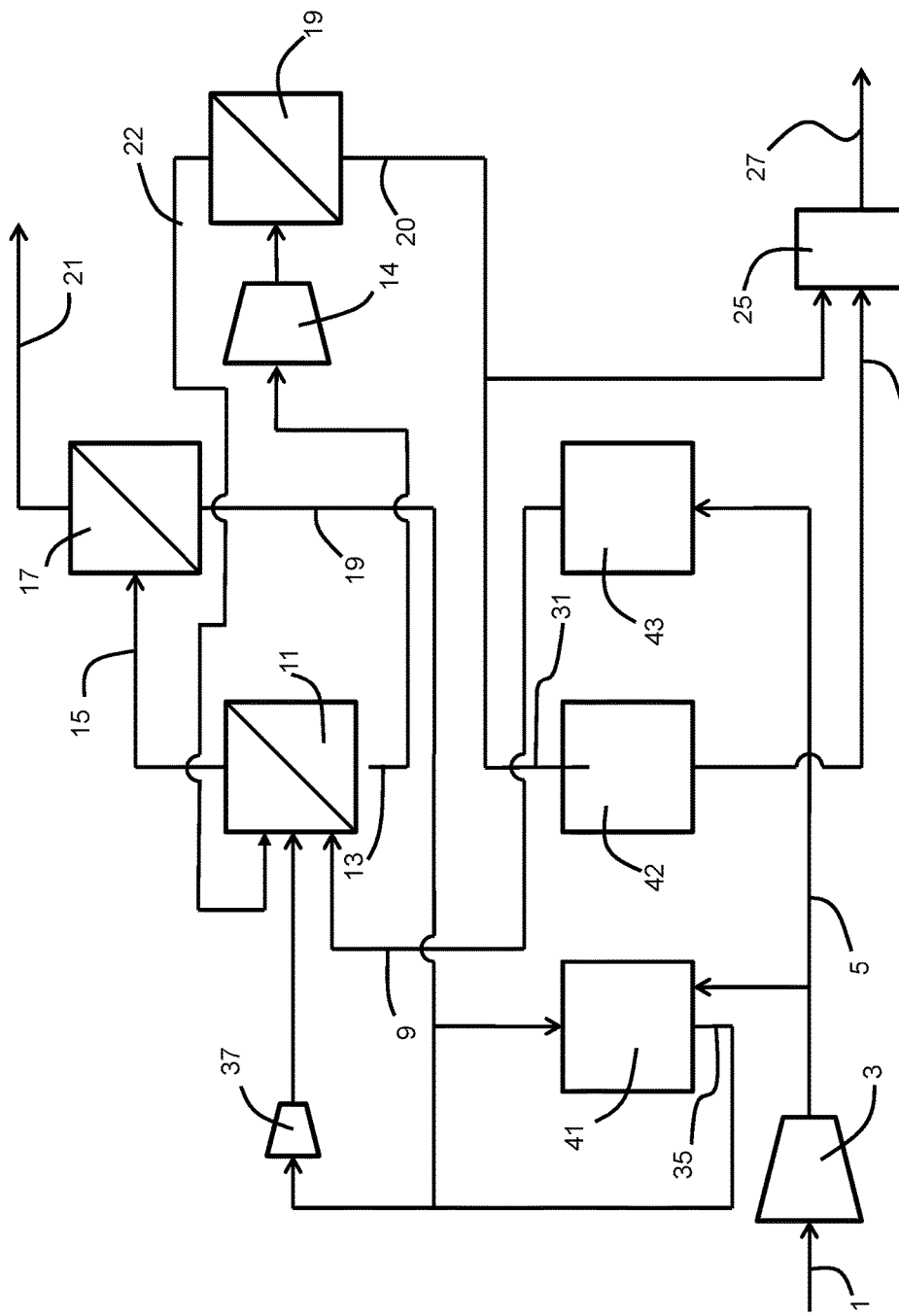

In another embodiment and as best shown in FIGS. 3A-3C and 3A'-3C', the PTSA unit 7 includes three adsorbent beds 41, 42, 43 that undergo three phases in the PTSA cycle as shown in Table I above.

In a first phase of the embodiment of FIGS. 3A-3C and 3A'-3C' and as best shown in FIGS. 3A and 3A', the raw biogas stream 1 is fed to and compressed by the main compressor 3. The PTSA feed gas stream 5 is withdrawn from the main compressor 3 and fed to a first adsorbent bed 41 of the PTSA unit 7 (the outlines of which are not illustrated for sake of clarity). The first adsorbent bed 41 undergoes adsorption in the first and second phases where it selectively adsorbs, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the first adsorbent bed 41 and fed to a feed gas inlet of the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13, withdrawn from a permeate gas outlet of the first gas separation membrane stage, is initially fed to the treatment unit 25 where it is burned or thermally oxidized to yield the vent gas 27.

The first stage retentate gas stream 15, withdrawn from a retentate gas outlet of the first gas separation membrane stage, is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas that is suitable for on-site use in generators or meets typical pipeline specifications for sale (as described above).

A waste stream 23 includes depressurization gas withdrawn from the third adsorption bed 43 of the PTSA unit 7 that is undergoing depressurization. The waste stream 23 is fed to the treatment unit 25 where it is burned or thermally oxidized to yield the vent gas 27. After the third bed 43 is suitably depressurized, instead of being directly fed to the treatment unit 25 and bypassing the PTSA unit 7, the first stage permeate gas stream 13 is heated at the heater 29 and fed as a regeneration gas stream 31 to the third adsorbent bed 42 which now undergoes regeneration. Thus, the waste stream 31 now includes the gas of the regeneration stream 31 plus impurities desorbed from the third adsorbent bed and is fed to the treatment unit 25 for burning or thermal oxidization to yield the vent gas 27.

The second stage permeate gas stream 19 is fed to the second adsorbent bed 42 which is undergoing cool down and recycled as a recycle stream 35 (containing the gas of the second stage permeate gas plus impurities desorbed from the second adsorbent bed 42) to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the second adsorbent bed reaches a suitable temperature, the second stage permeate gas stream 19 is instead fed to the suction inlet of the main compressor 3 where it combined and compressed with the raw biogas stream 1 to produce the PTSA feed gas stream 5. Simultaneous with this, the PTSA feed gas 5 is also fed to the second adsorbent bed 42 in order to repressurize it in anticipation of undergoing adsorption in the next phase of the PTSA cycle. Optionally, repressurization is conducted with PTSA product gas and/or the first or second gas separation membrane stage retentate gas streams 15, 21.

Alternatively and as shown in FIG. 3A', instead of feeding the recycle stream 35 or the second stage permeate gas stream 19 to the suction inlet of the main compressor 3, each may be fed to the suction inlet of the secondary compressor 37, compressed thereat, and subsequently fed to the first gas separation membrane stage 11. Optionally, the recycle stream 35 may be cooled before being fed to the suction inlet of the secondary compressor 37.

In a second phase of the embodiment of FIGS. 3A-3C and 3A'-3C' and as best shown in FIGS. 3B and 3B', the raw biogas stream 1 is continued to be fed to and compressed by the main compressor 3, but the PTSA feed gas stream 5 withdrawn from the main compressor 3 is now fed to the second adsorbent bed 42 as explained above.

The PTSA product gas 9 is withdrawn from the second adsorbent bed 42 and fed to the first gas separation membrane stage 11 where it is separated into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas that is suitable for on-site use in generators or meets typical pipeline specifications for sale (as described above).

A waste stream 23 includes depressurization gas withdrawn from the first adsorption bed 41 of the PTSA unit 7 that is undergoing depressurization. The waste stream 23 is fed to the treatment unit 25 where it is burned or thermally oxidized to yield the vent gas 27. After the first bed 41 is suitably depressurized, instead of being directly fed to the treatment unit 25 and bypassing the PTSA unit 7, the first stage permeate gas stream 13 is heated at the heater 29 and fed as a regeneration gas stream 31 to the first adsorbent bed 41 which now undergoes regeneration. Thus, the waste stream 23 now includes the gas of the regeneration stream 31 plus impurities desorbed from the first adsorbent bed 41 and is fed to the treatment unit 25 for burning or thermal oxidization to yield the vent gas 27.

The second stage permeate gas stream 19 is fed to the third adsorbent bed 43 (which is now undergoing cool down) and recycled as a recycle stream 35 (containing the gas of the second stage permeate gas plus impurities desorbed from the third adsorbent bed 43) to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the third adsorbent bed 43 reaches a suitable temperature, the second stage permeate gas stream 19 bypasses the third adsorbent bed 43 and is instead fed to the suction inlet of the main compressor 3 where it combined and compressed with the raw biogas stream 1 to produce the PTSA feed gas stream 5. Simultaneous with this, the PTSA feed gas stream 5 is also fed to the third adsorbent bed 43 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 3B', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11. Optionally, the recycle stream 35 may be cooled before being fed to the suction inlet of the secondary compressor 37.

In a third phase of the embodiment of FIGS. 3A-C and 3A'-3C' and as best shown in FIG. 3C and FIG. 3C', the raw biogas stream 1 is fed to and compressed by the main compressor 3. The PTSA feed gas stream 5 is withdrawn from the main compressor 3 and is now fed to the third adsorbent bed 43 instead of the second adsorbent bed 42. The third adsorbent bed 43 undergoes adsorption in the third and fourth phases where it selectively adsorbs, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the third adsorbent bed 43 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas as described above.

A waste stream 23 includes depressurization gas withdrawn from the second adsorption bed 42 which is now undergoing depressurization. The waste stream 23 is fed to the treatment unit 25 where it is burned or thermally oxidized to yield the vent gas 27. After the second bed 42 is suitably depressurized, instead of being directly fed to the treatment unit 25, the first stage permeate gas stream 13 is heated at the heater 29 and fed as a regeneration gas stream 31 to the second adsorbent bed 42 which is now undergoing regeneration. Thus, the waste stream 23 now includes the gas of the regeneration stream 31 plus impurities desorbed from the second adsorbent bed 42 and is fed to the treatment unit 25 for burning or thermal oxidization to yield the vent gas 27.

The second stage permeate gas stream 19 is fed to the first adsorbent bed 41 (which is now undergoing cool down) and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the first adsorbent bed 41 reaches a suitable temperature, the second stage permeate gas stream 19 bypasses the first adsorbent bed 41 and is instead fed to the suction inlet of the main compressor 3 where it combined and compressed with the raw biogas stream 1 to produce the PTSA feed gas stream 5. Simultaneous with this, the PTSA feed gas stream 5 is also fed to the first adsorbent bed 41 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 3C', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11.

In two particular other embodiments illustrated in FIGS. 3A"-3C" and 3A'"-3C'", there are three membrane gas separation stages 11, 17, 18 each of which includes one or more gas separation membranes selective for $CO_2$ over methane.

The difference between the embodiments of FIGS. 3A-3C/3A'-3C' and the embodiments of 3A"-3C"/3A'"-3C'" is as follows. Instead of heating the first stage permeate gas stream 13 and using it as a regeneration gas stream for one of the adsorbent beds 41, 42, 43 which have undergone depressurization, additional amounts of methane are recovered from the first stage permeate gas stream 13 at the third gas separation membrane stage 18. The first permeate gas stream 13 is first compressed at a tertiary compressor 14 to a pressure at or above that of the PTSA product gas stream 9 and subsequently fed to the third gas separation membrane stage 18 where it is separated into a third permeate stream 20 and a third retentate stream 22. The third retentate stream 22 is fed, along with the PTSA product gas stream 9, to the first gas separation membrane stage 11 where some of the methane recovered at the third stage 18 may be recovered in the first retentate gas 15. In this embodiment, the third permeate stream 20 performs the same functions of the first permeate stream 13 in the embodiment of FIGS. 3A-3C and 3A'-3C'. Thus, the regeneration stream 31 is fed to the adsorbent bed 41, 42, 43 (which has undergone regeneration) so as to desorb impurities from the one or more beds being regenerated. As with the embodiments of FIGS. 3A-3C and 3A'-3C', the regeneration stream 31, now containing desorbed impurities, is fed to the treatment unit 25 for burning or thermal oxidization to yield the vent gas 27. Finally, the embodiment of FIGS. 3A'"-3C'" differs from that of FIGS. 3A"-3C" in that, instead of feeding the recycle stream 35 to the suction inlet of the main compressor 3, in the embodiment of FIGS. 3A'"-3C'" it is compressed at a secondary compressor 37 and fed to the first gas separation membrane stage 11. Optionally, stream 35 is cooled before being fed to the suction inlet of the main or secondary compressor 3, 37.

In another embodiment and as best shown in FIGS. 4A-4D and 4A'-4D', the PTSA unit 7 includes four adsorbent beds 41, 42, 43, 44 that undergo three phases in the PTSA cycle as shown in Table III above.

Figure 4A:
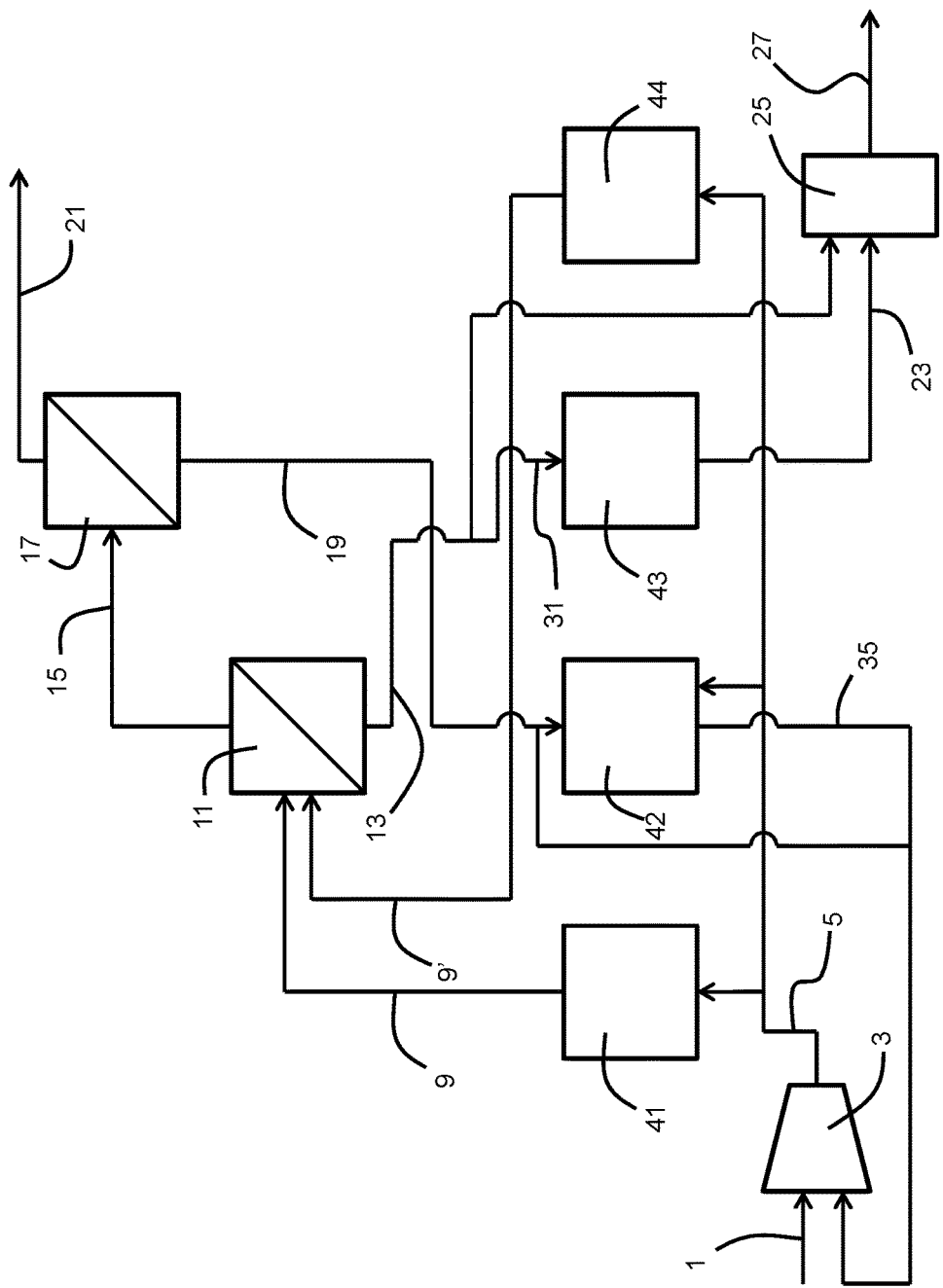
FIG. 4A is a schematic of a first phase of a first four-bed embodiment of the method and system of the invention.

In a first phase of the embodiment of FIGS. 4A-4D and 4A'-4D' and as best shown in FIGS. 4A and 4A', the raw biogas stream 1 is fed to and compressed by the main compressor 3. The PTSA feed gas stream 5 is withdrawn from the main compressor 3 and fed to the first and fourth adsorbent beds 41, 44 of the PTSA unit 7 (the outlines of which are not illustrated for sake of clarity) which selectively adsorb, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the first and fourth adsorbent beds 41, 44 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas that is suitable for on-site use in generators or meets typical pipeline specifications for sale (as described above).

A waste stream 23 includes depressurization gas withdrawn from the third adsorption bed 43 of the PTSA unit 7 that is undergoing depressurization. The waste stream 23 is fed to the treatment unit 25 where it is burned or thermally oxidized to yield the vent gas 27. After the third bed 43 is suitably depressurized, instead of being directly fed to the treatment unit 25 and bypassing the PTSA unit 7, the first stage permeate gas stream 13 is heated at the heater 29 and fed as a regeneration gas stream 31 to the third adsorbent bed 43 which now undergoes regeneration. Thus, the waste stream 23 now includes the gas of the regeneration stream 31 plus impurities desorbed from the third adsorbent bed and is fed to the treatment unit 25 for burning or thermal oxidization to yield the vent gas 27.

The second stage permeate gas stream 19 is fed to the second adsorbent bed 42 which is undergoing cool down and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the second adsorbent bed reaches a suitable temperature, the second stage permeate gas stream 19 is instead fed to the suction inlet of the main compressor 3 where it combined and compressed with the raw biogas stream 1 to produce the PTSA feed gas stream 5. Simultaneous with this, the PTSA feed gas 5 is also fed to the second adsorbent bed 42 in order to repressurize it in anticipation of undergoing adsorption in the next phase of the PTSA cycle. Optionally, repressurization is conducted with PTSA product gas and/or the first or second gas separation membrane stage retentate gas streams 15, 21.

Alternatively and as shown in FIG. 4A', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11. Optionally, the recycle stream 35 may be cooled before being fed to the suction inlet of the secondary compressor 37.

Figure 4B:
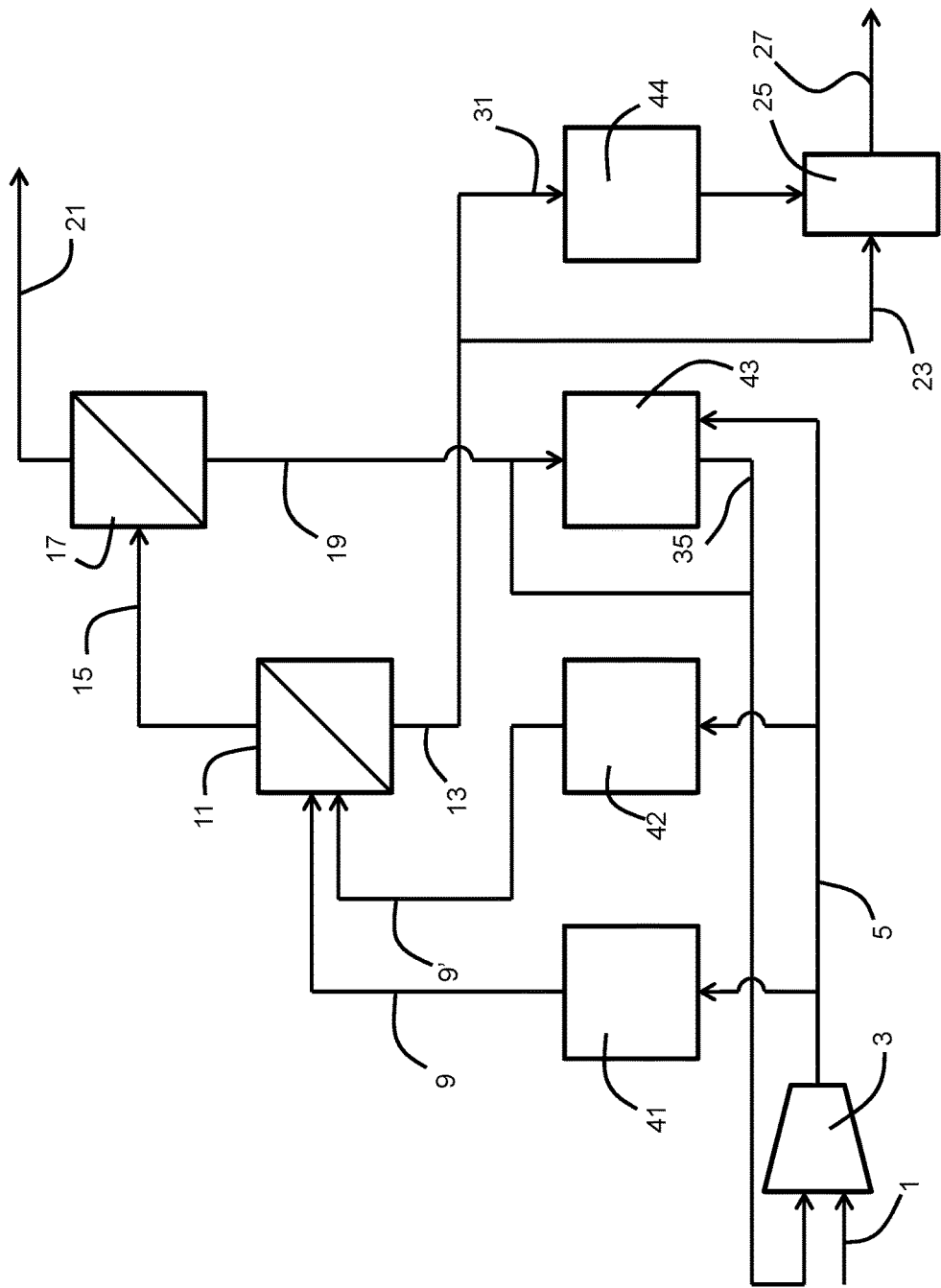
FIG. 4B is a schematic of a second phase of the first four-bed embodiment of the method and system of the invention.

In a second phase of the embodiment of FIGS. 4A-4D and 4A'-4D' and as best shown in FIGS. 4B and 4B', the raw biogas stream 1 is continued to be fed to and compressed by the main compressor 3, and the PTSA feed gas stream 5 withdrawn from the main compressor 3 is still fed to the first adsorbent bed 41. In this second phase, however, the PTSA feed gas stream 5 withdrawn from the main compressor 3 is no longer fed to the fourth adsorbent bed 44 but is instead fed to the second adsorbent bed 42. Thus, the first and second adsorbent beds 41, 42 undergo adsorption where they selectively adsorb, from the pressurized gas of the PTSA feed gas stream 5, $H_2S$, water, and VOCs (and optionally siloxanes) over methane and $H_2S$ over $CO_2$.

The PTSA product gas 9 is withdrawn from the first and second adsorbent beds 41, 42 and fed to the first gas separation membrane stage 11 where it is separated into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas that is suitable for on-site use in generators or meets typical pipeline specifications for sale (as described above).

A waste stream 23 includes depressurization gas withdrawn from the fourth adsorption bed 44 of the PTSA unit 7 that is undergoing depressurization. The waste stream 23 is fed to the treatment unit 25 where it is burned or thermally oxidized to yield the vent gas 27. After the first bed 44 is suitably depressurized, instead of being directly fed to the treatment unit 25 and bypassing the PTSA unit 7, the first stage permeate gas stream 13 is heated at the heater 29 and fed as a regeneration gas stream 31 to the fourth adsorbent bed 44 which now undergoes regeneration. Thus, the waste stream 23 now includes the gas of the regeneration stream 31 plus impurities desorbed from the fourth adsorbent bed 44 and is fed to the treatment unit 25 for burning or thermal oxidization to yield the vent gas 27.

The second stage permeate gas stream 19 is fed to the third adsorbent bed 43 (which is now undergoing cool down) and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the third adsorbent bed 43 reaches a suitable temperature, the second stage permeate gas stream 19 bypasses the third adsorbent bed 43 and is instead fed to the suction inlet of the main compressor 3 where it combined and compressed with the raw biogas stream 1 to produce the PTSA feed gas stream 5. Simultaneous with this, the PTSA feed gas stream 5 is also fed to the third adsorbent bed 43 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 4B', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11. Optionally, the recycle stream 35 may be cooled before being fed to the suction inlet of the secondary compressor 37.

Figure 4C:
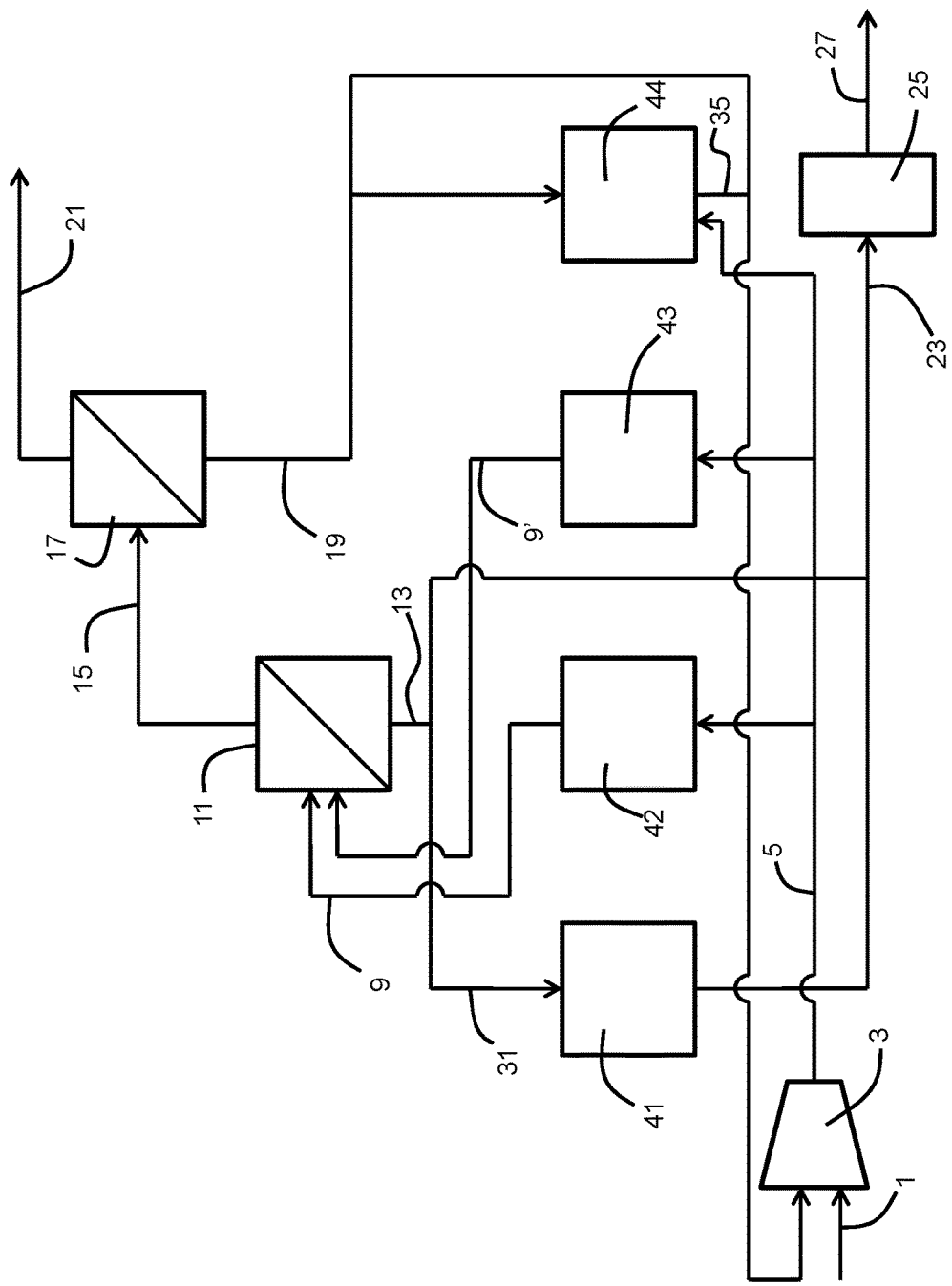
FIG. 4C is a schematic of a third phase of the first four-bed embodiment of the method and system of the invention.

In a third phase of the embodiment of FIGS. 4A-D and 4A'-3D' and as best shown in FIG. 4C and FIG. 4C', the raw biogas stream 1 is fed to and compressed by the main compressor 3. The PTSA feed gas stream 5 continues to be withdrawn from the main compressor 3 and fed to the second adsorbent bed 42. In this third phase, however, instead of also feeding the PTSA feed gas stream 5 to the first adsorbent bed 41, it is now fed to the third adsorbent bed 43. Thus, the second and third adsorbent beds 42, 43 undergo adsorption where they selectively adsorbs, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the second and third adsorbent beds 42, 43 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas as described above.

A waste stream 23 includes depressurization gas withdrawn from the first adsorption bed 41 which is now undergoing depressurization. The waste stream 23 is fed to the treatment unit 25 where it is burned or thermally oxidized to yield the vent gas 27. After the first bed 41 is suitably depressurized, instead of being directly fed to the treatment unit 25, the first stage permeate gas stream 13 is heated at the heater 29 and fed as a regeneration gas stream 31 to the first adsorbent bed 41 which is now undergoing regeneration. Thus, the waste stream 23 now includes the gas of the regeneration stream 31 plus impurities desorbed from the first adsorbent bed 41 and is fed to the treatment unit 25 for burning or thermal oxidization to yield the vent gas 27.

The second stage permeate gas stream 19 is fed to the fourth adsorbent bed 44 (which is now undergoing cool down) and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the fourth adsorbent bed 44 reaches a suitable temperature, the second stage permeate gas stream 19 is instead fed to the suction inlet of the main compressor 3 where it combined and compressed with the raw biogas stream 1 to produce the PTSA feed gas stream 5. Simultaneous with this, the PTSA feed gas stream 5 is also fed to the fourth adsorbent bed 44 in order to repressurize it in anticipation of undergoing adsorption in the fourth phase. Optionally, repressurization is conducted with PTSA product gas and/or the first or second gas separation membrane stage retentate gas streams 15, 21.

Alternatively and as shown in FIG. 4C', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11. Optionally, the recycle stream 35 may be cooled before being fed to the suction inlet of the secondary compressor 37.

Figure 4D:
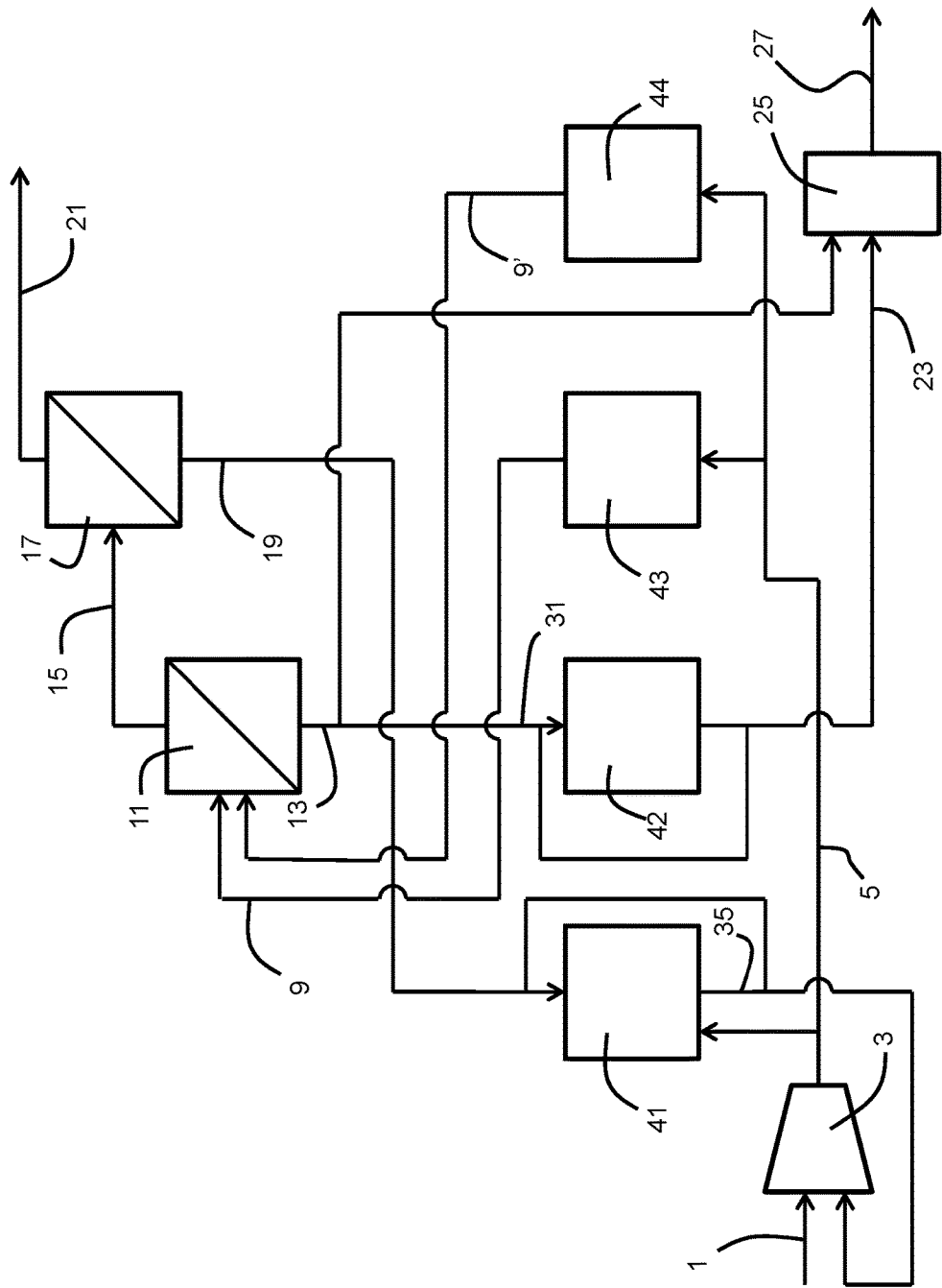
FIG. 4D is a schematic of a fourth phase of the four-bed embodiment of the method and system of the invention.
Figure 4A:
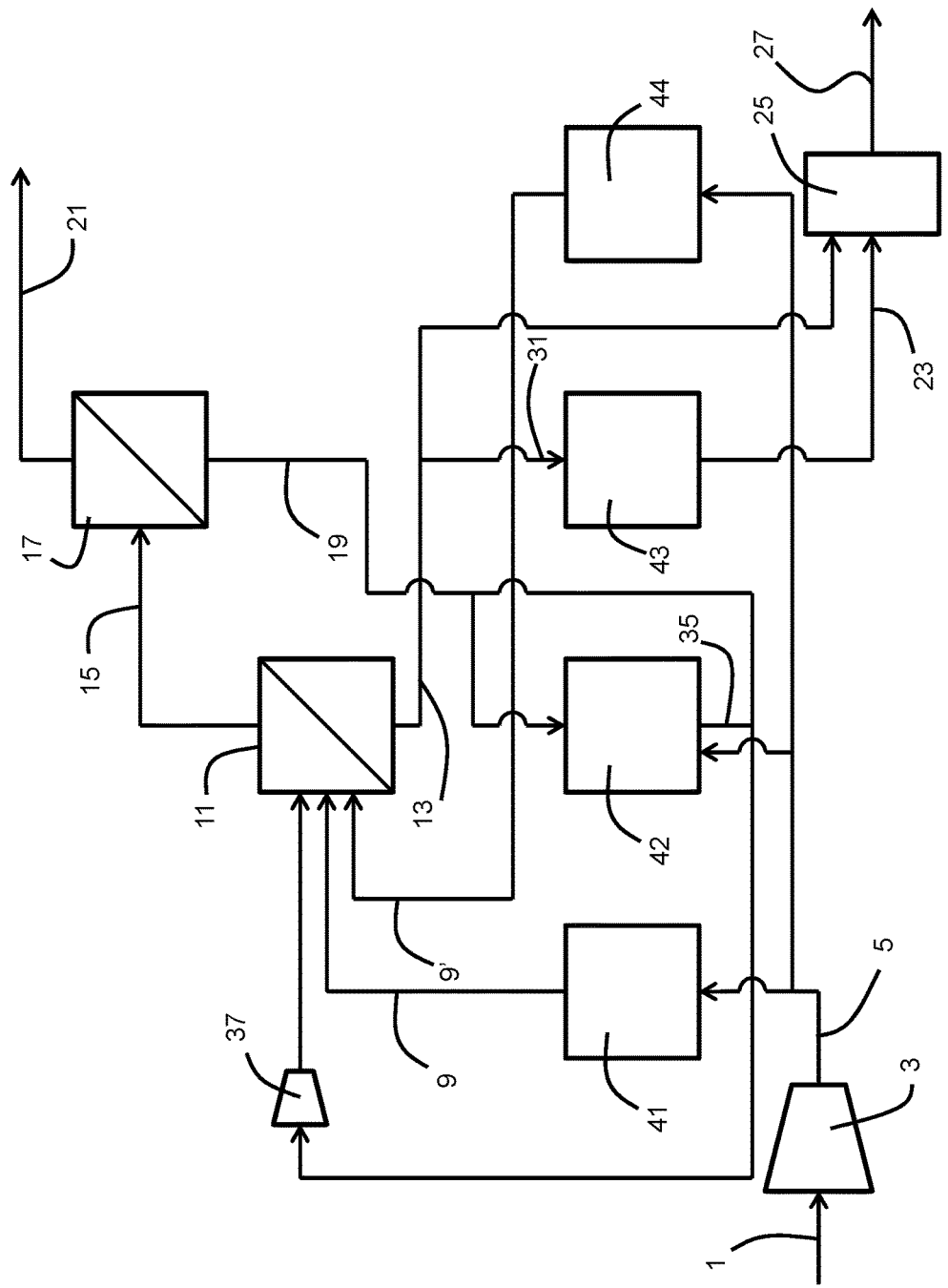
Figure 4B:
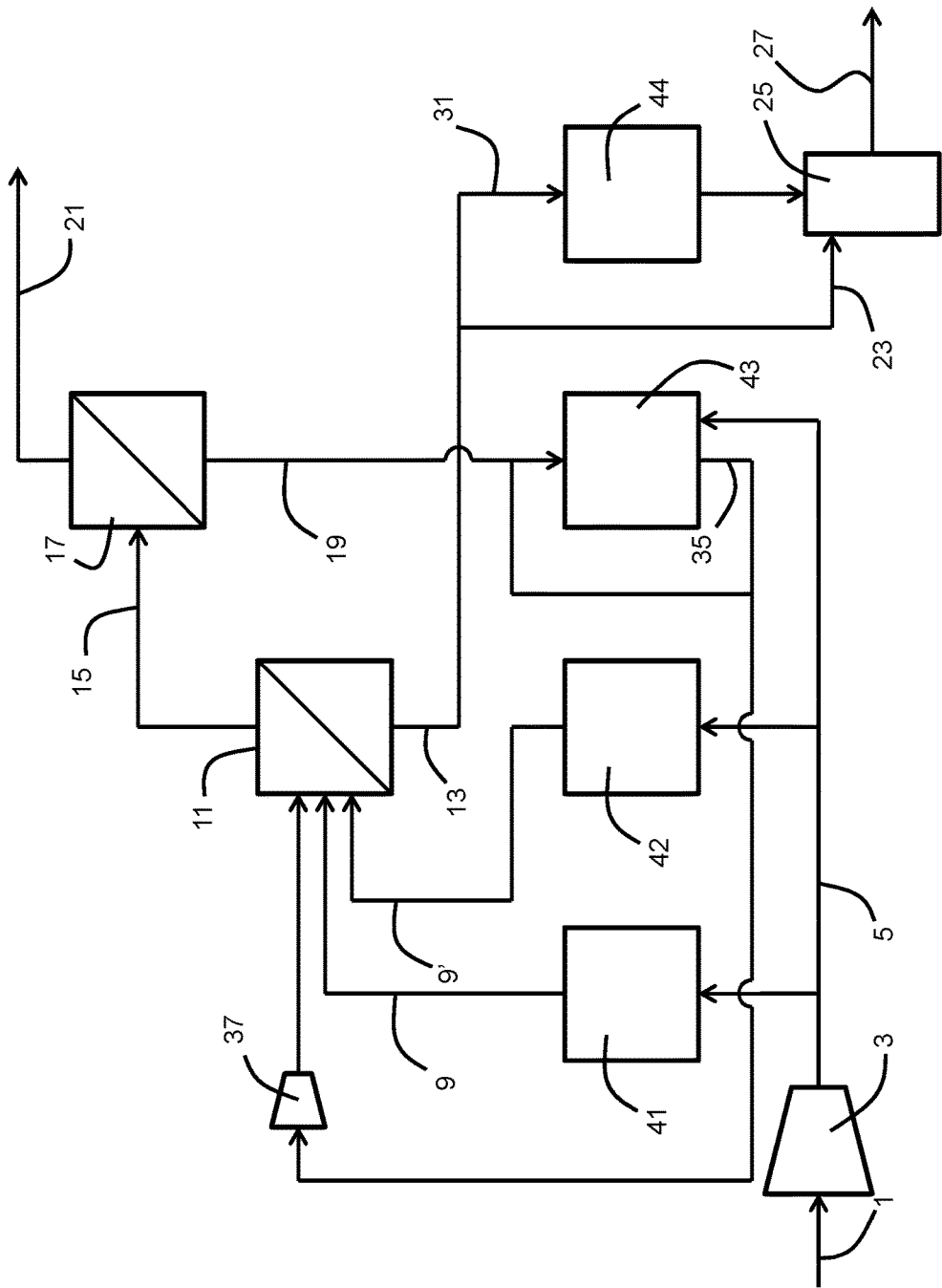
Figure 4C:
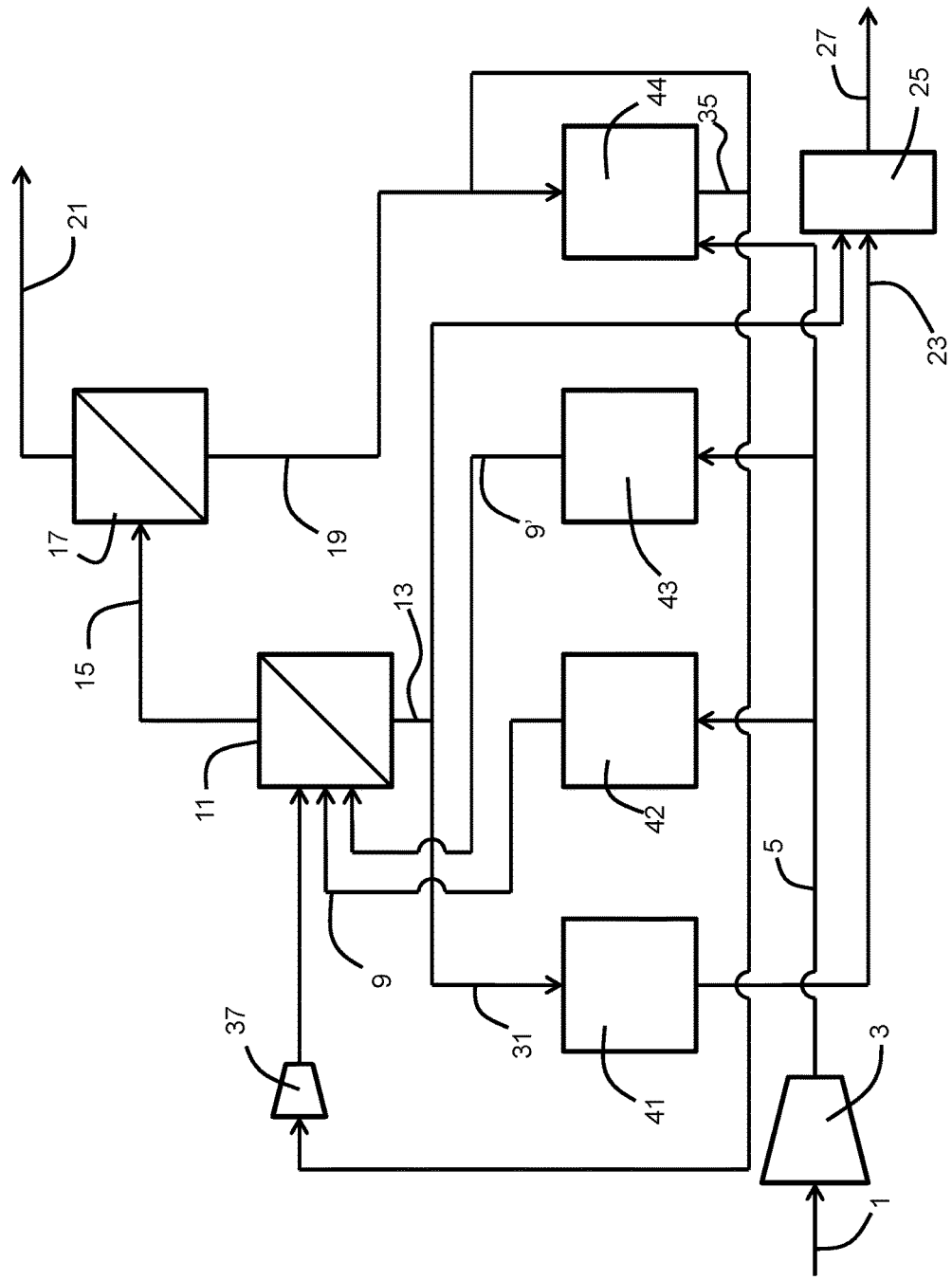
Figure 4D:
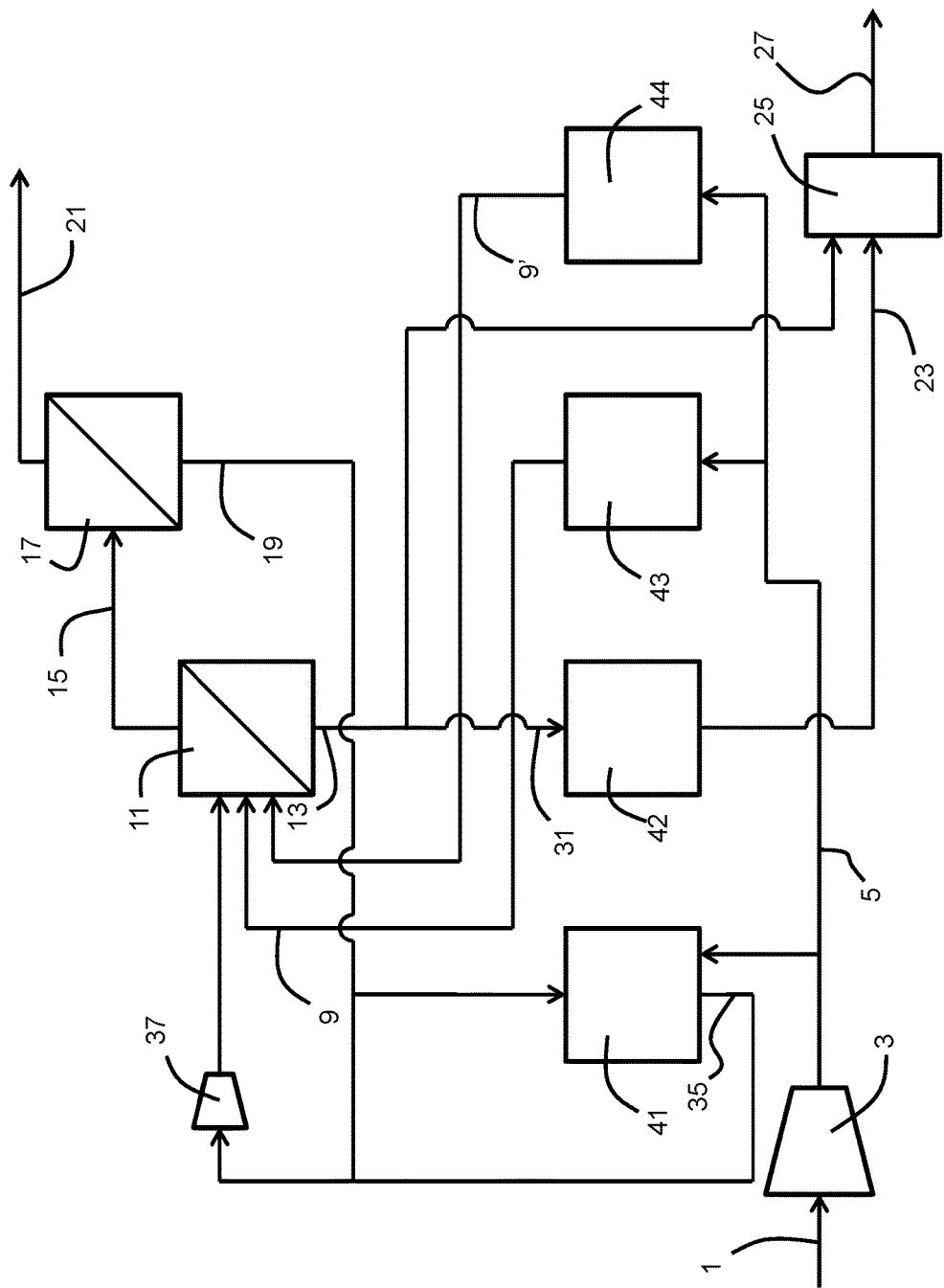
Figure 4A:
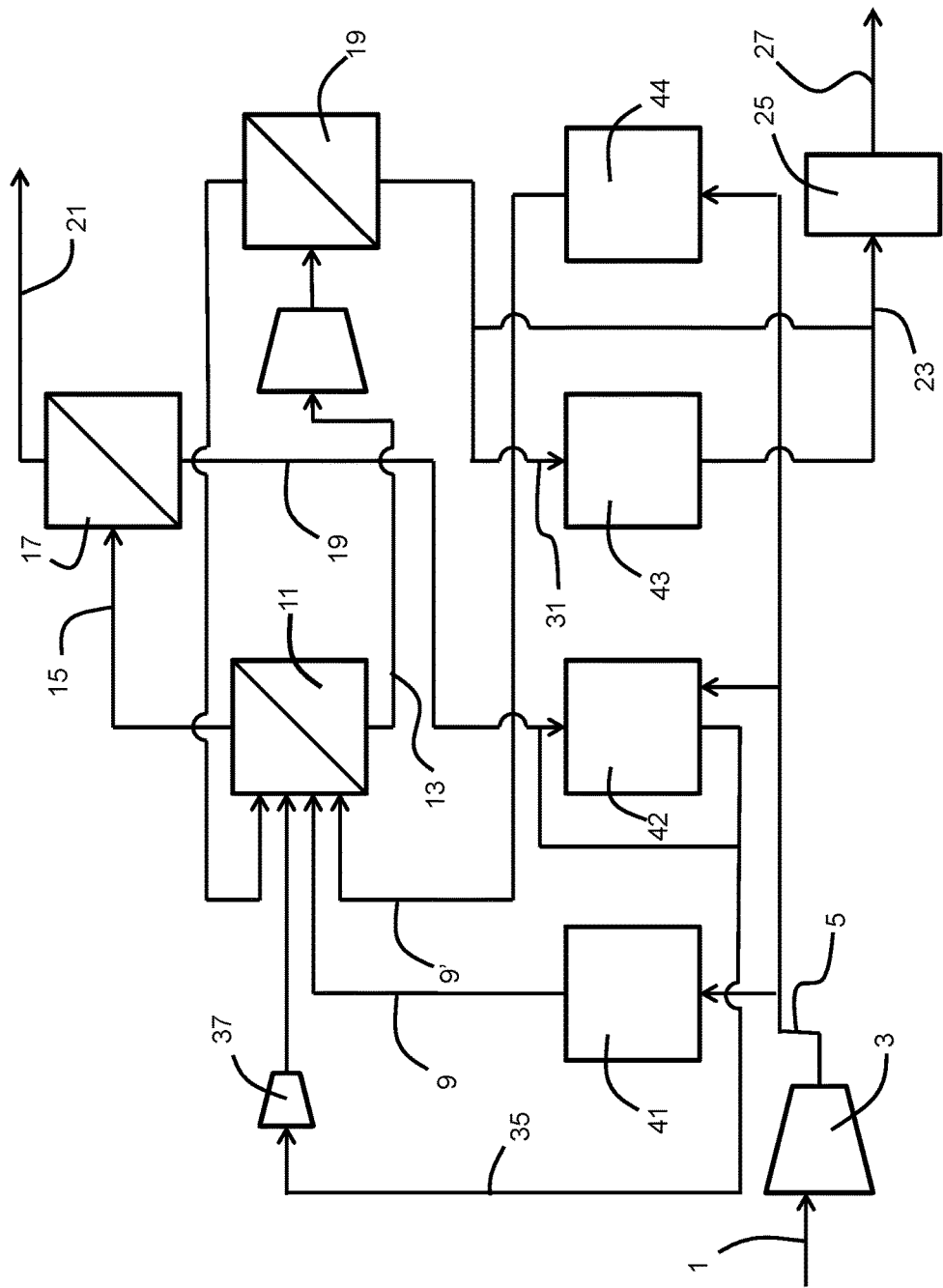
Figure 4B:
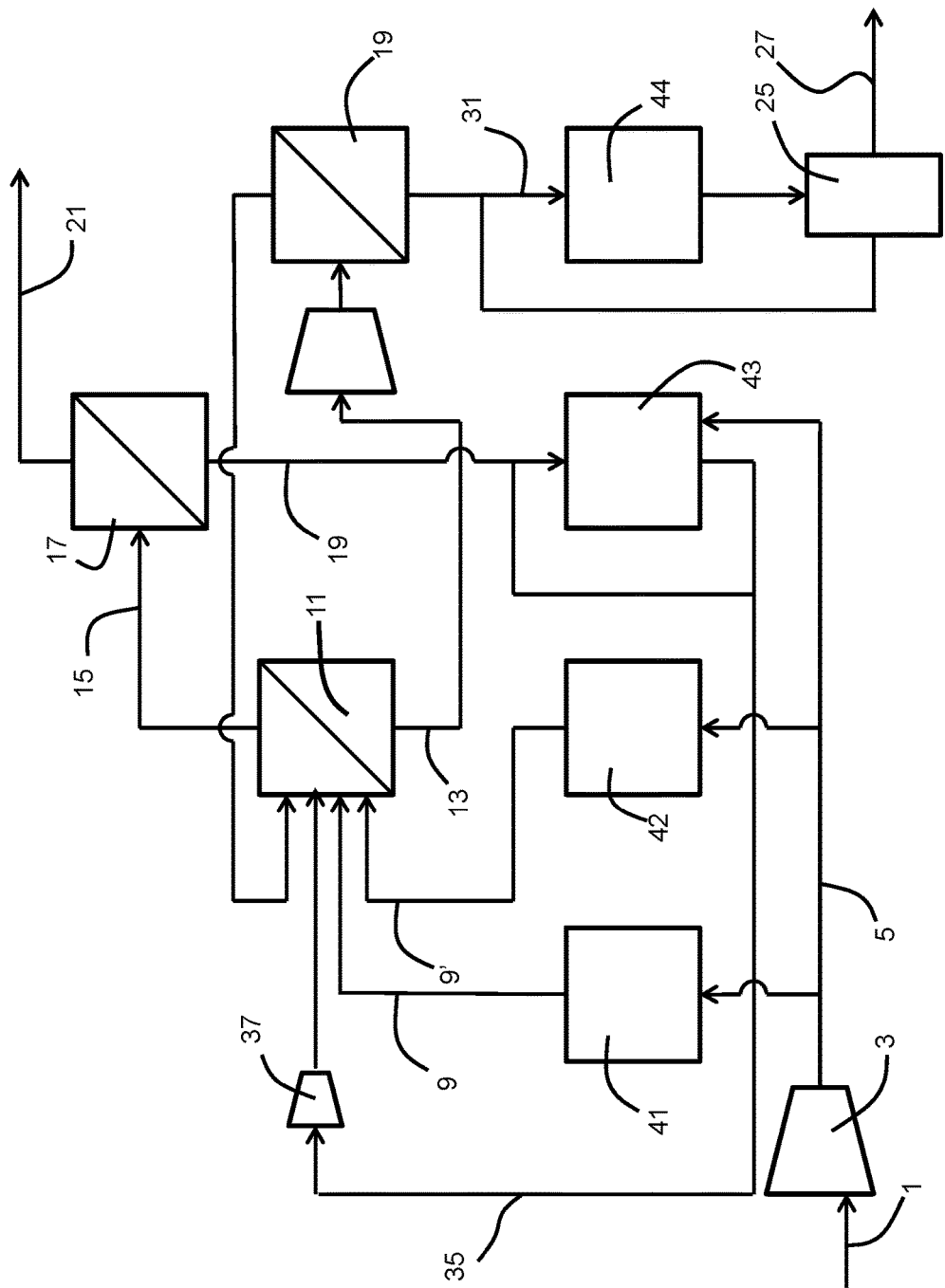
Figure 4C:
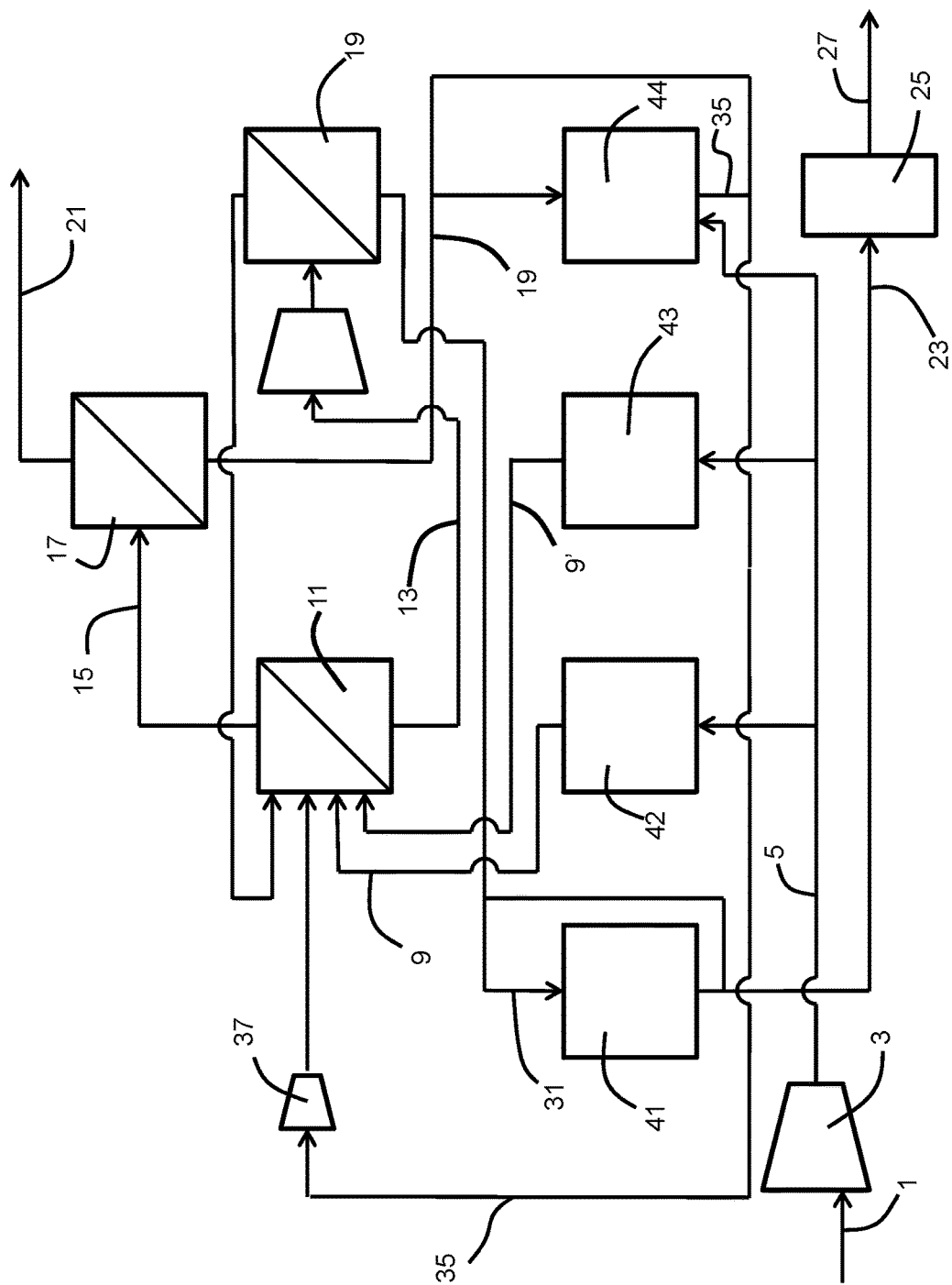
Figure 4D:
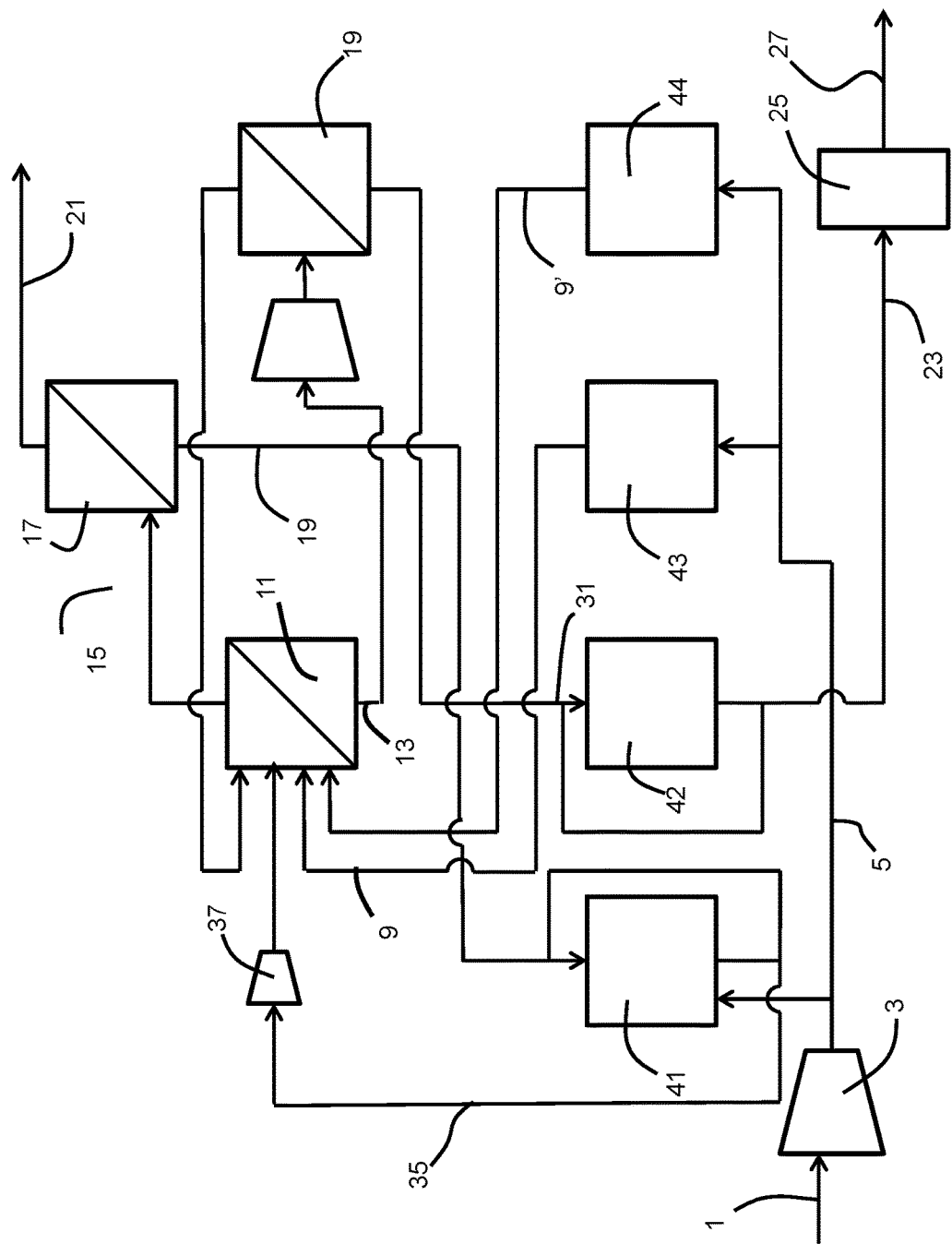

In a fourth phase of the embodiment of FIGS. 4A-D and 4A'-4D' and as best shown in FIG. 4D and FIG. 4D', the raw biogas stream 1 is fed to and compressed by the main compressor 3. The PTSA feed gas stream 5 continues to be withdrawn from the main compressor 3 and fed to the third adsorbent bed 43. In this fourth phase, however, instead of also feeding the PTSA feed gas stream 5 to the second adsorbent bed 42, it is now fed to the fourth adsorbent bed 44. Thus, the third and fourth adsorbent beds 43, 44 undergo adsorption where they selectively adsorb, from the pressurized gas of the PTSA feed gas stream 5, $H_2S$, water, and VOCs (and optionally siloxanes) over methane and $H_2S$ over $CO_2$.

The PTSA product gas 9 deficient in $H_2S$, water, and VOCs (and optionally siloxanes) and enriched in $CH_4$ and $CO_2$ in comparison to the PTSA feed gas stream 5 is withdrawn from the third and fourth adsorbent beds 43, 44 and fed to the first gas separation membrane stage 11. The first gas separation membrane stage 11, including one or more gas separation membranes selective for $CO_2$ over methane separate the PTSA product gas stream 9 into a first stage permeate gas stream 13 and a first stage retentate gas stream 15. The first stage permeate gas stream 13 is initially fed to the treatment unit 25 where it is burned or thermally oxidized to yield the vent gas 27.

The first stage retentate gas stream 15 is fed to the second gas separation membrane stage 17. The second gas separation membrane stage, including one or more gas separation membranes selective for $CO_2$ over methane separate the first stage retentate stream 15 into the second stage permeate stream 19 and the second stage retentate stream 21. The second stage retentate stream 21 is the product gas as described above.

A waste stream 23 includes depressurization gas withdrawn from the second adsorption bed 42 which is now undergoing depressurization. The waste stream 23 is fed to the treatment unit 25 where it is burned or thermally oxidized to yield the vent gas 27. After the second bed 42 is suitably depressurized, instead of being directly fed to the treatment unit 25, the first stage permeate gas stream 13 is heated at the heater 29 and fed as a regeneration gas stream 31 to the second adsorbent bed 42 which is now undergoing regeneration. Thus, the waste stream 23 now includes the gas of the regeneration stream 31 plus impurities desorbed from the second adsorbent bed 42 and is fed to the treatment unit 25 for burning or thermal oxidization to yield the vent gas 27.

The second stage permeate gas stream 19 is fed to the first adsorbent bed 41 (which is now undergoing cool down) and recycled as a recycle stream 35 to a suction inlet of the main compressor 3 where it is combined and compressed with the raw biogas stream 1 to yield the PTSA feed gas stream 5. Optionally, the recycle stream 35 may be cooled before being fed to the suction inlet of the main compressor 3.

When the first adsorbent bed 41 reaches a suitable temperature, the second stage permeate gas stream 19 is instead fed to the suction inlet of the main compressor 3 where it combined and compressed with the raw biogas stream 1 to produce the PTSA feed gas stream 5. Simultaneous with this, the PTSA feed gas stream 5 is also fed to the first adsorbent bed 41 in order to repressurize it in anticipation of undergoing adsorption in the third phase. Optionally, repressurization is conducted with PTSA product gas and/or the first or second gas separation membrane stage retentate gas streams 15, 21.

Alternatively and as shown in FIG. 4D', instead of feeding the second stage permeate gas stream 19 or the recycle stream 35 to the suction inlet of the main compressor 3, both may be fed to the suction inlet of the secondary compressor 37, compressed thereat, and subsequently fed to the first gas separation membrane stage 11. Optionally the recycle stream 35 may be cooled before being fed to the suction inlet of the secondary compressor 37.

In two particular other embodiments illustrated in FIGS. 4A"-4D" and 4A'"-4D'", there are three membrane gas separation stages 11, 17, 18 each of which includes one or more gas separation membranes selective for $CO_2$ over methane. The difference between the embodiments of FIGS. 4A-4D/4A'-4D' and the embodiments of 4A"-4D"/4A'"-4D'" is as follows. Instead of heating the first stage permeate gas stream 13 and using it as a regeneration gas stream for one of the adsorbent beds 41, 42, 43 which have undergone depressurization, additional amounts of methane are recovered from the first stage permeate gas stream 13 at the third gas separation membrane stage 18. The first permeate gas stream 13 is first compressed at a tertiary compressor 14 to a pressure at or above that of the PTSA product gas stream 9 and subsequently fed to the third gas separation membrane stage 18 where it is separated into a third permeate stream 20 and a third retentate stream 22. The third retentate stream 22 is fed, along with the PTSA product gas stream 9, to the first gas separation membrane stage 11 where some of the methane recovered at the third stage 18 may be recovered in the first retentate gas 15. In this embodiment, the third permeate stream 20 performs the same functions of the first permeate stream 13 in the embodiment of FIGS. 4A-4D and 4A'-4D'. Thus, the regeneration stream 31 is fed to the adsorbent bed 41, 42, 43 (which has undergone regeneration) so as to desorb impurities from the one or more beds being regenerated. As with the embodiments of FIGS. 4A-4D and 4A'-4D', the regeneration stream 31, now containing desorbed impurities, is fed to the treatment unit 25 for burning or thermal oxidization to yield the vent gas 27. Finally, the embodiment of FIGS. 4A'"-4D'" differs from that of FIGS. 4A"-4D" in that, instead of feeding the recycle stream 35 to the suction inlet of the main compressor 3, in the embodiment of FIGS. 4A'"-4D'" it is compressed at a secondary compressor 37 and fed to the first gas separation membrane stage 11. Optionally, stream 35 is cooled before being fed to the suction inlet of the main or secondary compressor 3, 37.

I note that, for the sake of clarity, heater 29 is not illustrated in any of FIGS. 2A-2D, 2A'-2D', 2A-2D", 2A'"-2D'", 3A-3C, 3A'-3C', 3A"-3C", 3A'"-3C'", 4A-4D, 4A'-D', 4A"-4D", or 4A'"-D'", but it should be understood as present in each of those schemes for the purpose of heating the first stage permeate stream 13 as discussed above.

Finally, I note that aspects of the invention are not limited to the use of first and/or second gas separation membrane stage retentate gas streams 15, 21 for use as the regeneration and cool down gases. Indeed, any permutation of three or more gas separation membrane stages may be used in which any one or more of the permeate streams (the entirety of a stream or only a portion of a stream) may be used as the regeneration gas and/or cool down gas.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing i.e. anything else may be additionally included and remain within the scope of "comprising." "Comprising" is defined herein as necessarily encompassing the more limited transitional terms "consisting essentially of" and "consisting of"; "comprising" may therefore be replaced by "consisting essentially of" or "consisting of" and remain within the expressly defined scope of "comprising".

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A biogas upgrading system based upon PTSA and gas separation membranes, comprising:
    a source of raw biogas comprising methane, $CO_2$, water, VOCs, and $H_2S$;
    a main compressor including a suction inlet in fluid communication with the source and receiving a stream of raw biogas from the source;
    a PTSA unit comprising two or more adsorbent beds each of which is selective for water, VOCs, and $H_2S$ over CO$_2$ and for H$_2$S over methane, the PTSA unit being in downstream fluid communication with the main compressor and receiving a stream of a PTSA feed gas therefrom, the PTSA unit being adapted and configured to adsorb water, VOCs, and H$_2$S from the PTSA feed gas and produce a PTSA product gas deficient in water, VOCs, and H$_2$S in comparison to the PTSA feed gas;

a first gas separation membrane stage comprising one or more gas separation membranes selective for CO$_2$ and O$_2$ over methane, a feed gas inlet of the first gas separation membrane stage being in downstream fluid communication with the PTSA unit, the first gas separation membrane stage being configured and adapted to separate the PTSA product gas into a first stage permeate gas stream and a first stage retentate gas stream;

a second gas separation membrane stage comprising one or more gas separation membranes selective for CO$_2$ and O$_2$ over methane, a feed gas inlet of the second gas separation membrane stage being in downstream fluid communication with the retentate outlet of the first gas separation membrane stage and receiving the first stage permeate gas stream therefrom, the second gas separation membrane stage being adapted and configured to separate the first retentate gas stream into a second permeate gas stream and a second retentate gas stream, wherein:

the PTSA unit is in fluid communication with the permeate gas outlet of the first gas separation membrane stages so as to receive a flow of the first stage permeate gas for use as a thermal regeneration gas to thermally regenerate and desorb water, VOCs, and H$_2$S that was adsorbed upon the adsorbent beds from the PTSA feed gas stream; and the PTSA unit is in fluid communication with the permeate gas outlet of the second gas separation membrane stage so as to receive a flow of the second permeate gas stream for use as a cool down stream for cooling one or more adsorbent beds after thermal regeneration thereof; and a treatment unit in downstream fluid communication with the PTSA unit so as to receive a waste gas from the PTSA comprised of the thermal regeneration gas and water, VOCs, and H$_2$S, the treatment unit being adapted and configured to either oxidize or burn the VOCs contained in the waste gas.

2. The system of claim 1, wherein the suction inlet of the main compressor is in fluid communication with the PTSA unit so as to receive the cool down gas stream from the PTSA unit and allow combination and compression with the raw biogas stream.

3. The system of claim 1, further comprising a secondary compressor including a suction inlet that is in fluid communication with the PTSA unit so as to receive the cool down gas stream from the PTSA, wherein the feed gas inlet of the first gas separation membrane stage is in downstream fluid communication with an outlet of the secondary compressor so as to receive the cool down gas stream after compression by the secondary compressor and separate a combined feed of the cool down gas stream and the PTSA product gas into the first stage permeate gas stream and a first stage retentate gas stream.

4. The system of claim 1, wherein the main compressor includes an oil cooling circuit including a heat exchanger adapted and configured to exchange heat between the first stage permeate and oil flowing in the cooling circuit so as to heat the first stage permeate to the temperature at which thermal regeneration of the adsorbent beds is to take place.

5. The system of claim 1, further comprising a H2S removal unit in flow communication between the main compressor and the PTSA unit, the H2S removal unit being adapted and configured to remove amounts of H$_2$S present in the PTSA feed gas stream prior to feeding the PTSA feed gas stream to the PTSA unit, wherein the PTSA unit is adapted and configured to remove amounts of water and VOCs from the PTSA feed gas stream and also amounts of the H$_2$S remaining in the PTSA feed gas stream after treatment by the H$_2$S removal unit.

6. The system of claim 1, further comprising a heat exchanger adapted and configured to exchange heat between hot gas from the treatment unit and the regeneration gas stream so as to heat the regeneration gas stream to the temperature above the PTSA feed gas temperature.

* * * * *